(12) United States Patent
Davis et al.

(10) Patent No.: US 6,541,605 B1
(45) Date of Patent: Apr. 1, 2003

(54) CYTOKINE-, STRESS-, AND ONCOPROTEIN-ACTIVATED HUMAN PROTEIN KINASE KINASES

(75) Inventors: Roger J. Davis, Princeton, MA (US); Joel Raingeaud, Palaiseau (FR); Benoit Derijard, Nice (FR)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/057,009

(22) Filed: Apr. 7, 1998

Related U.S. Application Data

(63) Continuation of application No. 08/530,950, filed on Sep. 19, 1995, now Pat. No. 5,736,381, which is a continuation-in-part of application No. 08/446,083, filed on May 19, 1995, now Pat. No. 5,804,427.

(51) Int. Cl.$^7$ .......................... C07K 14/00; C12Q 1/68; C12P 19/34; C07H 21/02; C07H 21/04
(52) U.S. Cl. ........................ 530/350; 435/6; 435/7.1; 435/91.1; 435/91.2; 536/22.1; 536/23.1; 536/24.3; 536/24.31; 536/24.32; 536/24.33
(58) Field of Search ................... 435/6, 91.2; 536/22.1, 536/23.1

(56) References Cited

FOREIGN PATENT DOCUMENTS

| EP | 96 90 5233 | 11/1998 |
|---|---|---|
| WO | WO 94/24159 | 10/1994 |
| WO | WO 95/28421 | 10/1995 |
| WO | PCT/US96/01078 | 5/1996 |

OTHER PUBLICATIONS

Davis, *Elsevier Science Ltd.*, TIBS 19:470–473, (1994).
Dérijard et al., *Science*, 267:682–685, (1995).
Freshney et al., *Cell*, 78:1039–1049, (1994).
Galcheva–Gargova et al., *Science*, 265:806–808, (1994).
Gupta et al., *Science*, 267:389–393, (1995).
Han et al., *J. Biol. Chem.*, 271:2886–2891, Feb. (1996).
Hillier et al., EMBL Database entry HS78336; Accession No. T66783; Apr. 8, 1995; The WashU–Merck EST Project, XP002058577 (abstract).
Lin et al., *Science*, 268:286–290, (1995).
Minden et al., *Science*, 266:1719–1723, (1994).
Raingeaud et al., *The Journal of Biological Chemistry*, 270:7420–7426, (1995).
Rouse et al., *Cell*, 78:1027–1037, (1994).
Sanchez et al., *Nature*, 372:794–798, (1994).
Seger et al., *J. Biological Chemistry*, 267:25628–25631 (1992).
Whitmarsh et al., Science, 269:403–407, (1995).
Wu et al., *Molecular and Cellular Biology*, 13:4539–4548, (1993).
Xia et al., *Science*, 270:1326–1331, (1995).
Yan et al., *Nature*, 372:798–800, (1994).
Yashar et al., *Molecular and Cellular Biology*, 13:5738–5748, (1993).

*Primary Examiner*—Jeffrey Siew
(74) *Attorney, Agent, or Firm*—Fish & Richardson P.C.

(57) ABSTRACT

Disclosed are human mitogen-activated (MAP) kinase kinase isoforms (MKKs). MKKs mediate unique signal transduction pathways that activate human MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

10 Claims, 27 Drawing Sheets

```
                                                                                          71
MKK3               MSKPP---------APNPTPPRN----------LDSRTFITIG------DRNFEVEADD
MKK4      MQGKRKALKLNFAN..FKSTARFTLN....GVQ.PHIERLRTHSIE.SGKLK.SP-----EQHWDFT.E.
MEK1      MPKKKP--TPIQLN.A-PDGSAVNGTSSAETNLEALQKKLEELE..EQQRKRLEAFLTQKQKVG.LKD..
MEK2      MLARRKPVLPALTIN.TIAEGPSPTSEGASEANLVDLQKKLEELE..EQQKKRLEAFLTQKAKVG.LKD..
PBS2      <GTTPRTGNSNNS-NSGSSGGGGLFANFSKYVDIKSGSLNFAGKLSL.SKG.DFSN-----GSSSRITL.E
Consensus 72       I                   II           III           IV        142
MKK3      LVTISELGRGAYGVVEKVRHAQSGTIMAVKRIRATVNSQEQKRLLMDLDINMRTVDCFYTVTFYGALFREG
MKK4      .KDLG.I......S.N.MV.KP..Q........S..DEK...Q......VV..SS..P.I.Q.........
MEK1      FEK.....A.NG...F.VS.KP..LV..R.L.HLEIKPAIRNQIIRE.QV-LHECNSP.I.G....FYSD.
MEK2      FER.....A.NG...T.VQ.RP..L...R.L.HLEIKPAIRNQIIRE.QV-LHECNSP.I.G....FYSD.
PBS2      .EFLD...H.N..N.S.VL.KPTNV...T.EV.LELDEAKFRQI..E.EV-LHKCNSP.I.D....F.I..
Consensus       E G   G VK H      MA K            L          Y V FYGA     G 143      V                                            VI         213
MKK3      DVWICMELMD-TSLDKFYR---KVLDKNMTIPEDILGEIAVSIVRALEHLHSKLSVIHRDVKPSNVL-INK
MKK4      .C........S--..F....KYVYS...D--V...E...K.TLAT.K..N..KEN.KI....I....I.-LDR
MEK1      EIS....H..GG...Q-------..K.AGR...Q...KVSIAVIKG.TY.RE.HKIM........I.-V.S
MEK2      EIS....H..GG...Q-------..KEAKR...E...KVSIAVL.G.AY.RE.HQIM........I.-V.S
PBS2      A.YM...Y..GG....IYDESSEIGG----.D.PQ.AF..NAVIHG.KE.KEQHNI.......T.I.CSAN
Consensus     CME M  S D             I E L          L  L       HRD KP N L 214      VII          *   *    VIII          IX                  284
MKK3      EGHVKMCDFGISGYLVDSVAKTMDAGCKPYMAPERINP-ELNQKGYNVKSDVWSLGITMIEMAILRFPY--
MKK4      S.NI.L........Q....I...R....R.....D-SASRQ..D.R.........LY.L.TG....--
MEK1      R.EI.L.....V..Q.I...M.NSF-V.TRS...S....LQGTH-----.S.Q...I...M.LSLV...VG.Y.IPP
MEK2      R.EI.L.....V..Q.I...M.NSF-V.TRS.......LQGTH-----.S.Q...I...M.LSLV.L.VG.Y.IPP
PBS2      Q.T..L.....V..N..A.L.....NI..QS........KSLNPDRAT.T.Q...I.....LSIL...LG.Y..PP
Consensus    G  K CDFG SG L  S A       G   YM PER        Y V SD WS G    EA  R P 285                                                  X           355
MKK3      ESWG---------------------------------TPFQQLKQVVEEPSPQLPAD---R
MKK4      PK.N---------------------------------SV.D..T...KGDP...SNSEERE
MEK1      PDAKELELMFGCQV----EGDAAETPPRPRTPGRPLSSYGMDSRPPMAI.EL.DYI.N..P.K..SGV---
MEK2      PDAKELEAIFGRPVVDGEEGEPHSISPRPRPPGRPVSGHGMDSRPAMAI.EL.DYI.N..P.K..NGV---
PBS2      .TYD--------------------------------------NI.S..SAI.DG.P.R..S.---K
Consensus                                                       F  L  V  P L 356                   XI                                         426
MKK3      FSPEFVDFTAQCLRKNPAERMSYLELMEHPFFTLHKTKKTDIAAFVK-------KILGEDS
MKK4      ...S.IN.VNL..T.DESK.PK.K...LK...ILMYEERAVEV.CY.C-------...DQMPATPSSPMYVD
MEK1      ..L..Q..VNK..I......ADLKQ..V.A.IKRSDAEEV.F.GWLCSTIGLNQPSTPTHAAGV
MEK2      .T.D.QE.VNK..I......ADLKM.TN.T.IKRSEVEEV.F.GWLCKTLRLNQPGTPTRTA
PBS2      ..SDAQD.VSL..Q.I.ER.PT.AA.T...PWLVKYRNQDVHMSEYITERLERRN...R.RGENGLSKNVP>
Consensus F       F    CL K    R        L   H
```

FIG. 1

```
       5         10        15        20        25        30        35        40        45        50        55        60
       *                             *                             *                             *
TGGCTGGCAA TGGCCTTGCT GACCTCGAGC CGGGCCCACG TGGGGACCTT TGGAGCACAG
ACCGACCGTT ACCGGAACGA CTGGAGCTCG GCCCGGGTGC ACCCCTGGAA ACCTCGTGTC 65        70        75        80        85        90        95       100       105       110       115       120
       *                             *                             *                             *
CCTACGATCC TGGTGCAAGG CCGGTGGATG CAGAGGCCAG TCCATATACC ACCCAGGCCT
GGATGCTAGG ACCACGTTCC GGCCACCTAC GTCTCCGGTC AGGTATATGG TGGGTCCGGA 125       130       135       140       145       150       155       160       165       170       175       180
       *                             *                             *                             *
GCGAGGAGCG TGGTCCCCAC CCATCCAGCC CATATGTGCA AGTGCCCTTG ACAGAGAGGC
CGCTCCTCGC ACCAGGGGTG GGTAGGTCGG GTATACACGT TCACGGGAAC TGTCTCTCCG 185       190       195       200       205       210       215       220       225       230       235       240
       *                             *                             *                             *
TGGTCATATC CATGGTGACC ATTTATGGGC CACAACAGGT CCCCATCTGC GCAGTGAACC
ACCAGTATAG GTACCACTGG TAAATACCCG GTGTTGTCCA GGGGTAGACG CGTCACTTGG 245       250       255       260       265       270       275       280       285       290       295       300
       *                             *                             *                             *
CTGTGCTGAG CACCTTGCAG ACGTGATCTT GCTTCGTCCT GCAGCACTGT GCGGGGCAGG
GACACGACTC GTGGAACGTC TGCACTAGAA CGAAGCAGGA CGTCGTGACA CGCCCCGTCC 305       310       315       320       325       330       335       340       345       350       355
       *                             *                             *                             *
AAAATCCAAG AGGAAGAAGG ATCTACGGAT ATCCTGC ATG TCC AAG CCA CCC GCA
TTTTAGGTTC TCCTTCTTCC TAGATGCCTA TAGGACG TAC AGG TTC GGT GGG CGT
                                          Met Ser Lys Pro Pro Ala>

360       365       370       375       380       385       390       395       400
             *                   *                   *                   *
CCC AAC CCC ACA CCC CCC CGG AAC CTG GAC TCC CGG ACC TTC ATC ACC
GGG TTG GGG TGT GGG GGG GCC TTG GAC CTG AGG GCC TGG AAG TAG TGG
Pro Asn Pro Thr Pro Pro Arg Asn Leu Asp Ser Arg Thr Phe Ile Thr>

405       410       415       420       425       430       435       440       445       450
           *                   *                   *                   *                   *
ATT GGA GAC AGA AAC TTT GAG GTG GAG GCT GAT GAC TTG GTG ACC ATC
TAA CCT CTG TCT TTG AAA CTC CAC CTC CGA CTA CTG AAC CAC TGG TAG
Ile Gly Asp Arg Asn Phe Glu Val Glu Ala Asp Asp Leu Val Thr Ile>

455       460       465       470       475       480       485       490       495
                  *                   *                   *                   *
TCA GAA CTG GGC CGT GGA GCC TAT GGG GTG GTA GAG AAG GTG CGG CAC
AGT CTT GAC CCG GCA CCT CGG ATA CCC CAC CAT CTC TTC CAC GCC GTG
Ser Glu Leu Gly Arg Gly Ala Tyr Gly Val Val Glu Lys Val Arg His>

500       505       510       515       520       525       530       535       540       545
 *                   *                   *                   *                   *
GCC CAG AGC GGC ACC ATC ATG GCC GTG AAG CGG ATC CGG GCC ACC GTG
CGG GTC TCG CCG TGG TAG TAC CGG CAC TTC GCC TAG GCC CGG TGG CAC
Ala Gln Ser Gly Thr Ile Met Ala Val Lys Arg Ile Arg Ala Thr Val>

550       555       560       565       570       575       580       585       590       595
 *                   *                   *                   *                   *
AAC TCA CAG GAG CAG AAG CGG CTG CTC ATG GAC CTG GAC ATC AAC ATG
TTG AGT GTC CTC GTC TTC GCC GAC GAG TAC CTG GAC CTG TAG TTG TAC
Asn Ser Gln Glu Gln Lys Arg Leu Leu Met Asp Leu Asp Ile Asn Met>
```

FIG. 4A

```
      600       605       610       615       620       625       630       635       640
       *                   *                   *                   *                   *
      CGC   ACG   GTC   GAC   TGT   TTC   TAC   ACT   GTC   ACC   TTC   TAC   GGG   GCA   CTA   TTC
      GCG   TGC   CAG   CTG   ACA   AAG   ATG   TGA   CAG   TGG   AAG   ATG   CCC   CGT   GAT   AAG
      Arg   Thr   Val   Asp   Cys   Phe   Tyr   Thr   Val   Thr   Phe   Tyr   Gly   Ala   Leu   Phe>

645       650       655       660       665       670       675       680       685       690
                 *                   *                   *                   *                   *
      AGA   GAG   GGA   GAC   GTG   TGG   ATC   TGC   ATG   GAG   CTC   ATG   GAC   ACA   TCC   TTG
      TCT   CTC   CCT   CTG   CAC   ACC   TAG   ACG   TAC   CTC   GAG   TAC   CTG   TGT   AGG   AAC
      Arg   Glu   Gly   Asp   Val   Trp   Ile   Cys   Met   Glu   Leu   Met   Asp   Thr   Ser   Leu>

695       700       705       710       715       720       725       730       735
                     *                   *                   *                   *
          GAC   AAG   TTC   TAC   CGG   AAG   GTG   CTG   GAT   AAA   AAC   ATG   ACA   ATT   CCA   GAG
          CTG   TTC   AAG   ATG   GCC   TTC   CAC   GAC   CTA   TTT   TTG   TAC   TGT   TAA   GGT   CTC
          Asp   Lys   Phe   Tyr   Arg   Lys   Val   Leu   Asp   Lys   Asn   Met   Thr   Ile   Pro   Glu>

740       745       750       755       760       765       770       775       780       785
       *                   *                   *                   *                   *
      GAC   ATC   CTT   GGG   GAG   ATT   GCT   GTG   TCT   ATC   GTG   CGG   GCC   CTG   GAG   CAT
      CTG   TAG   GAA   CCC   CTC   TAA   CGA   CAC   AGA   TAG   CAC   GCC   CGG   GAC   CTC   GTA
      Asp   Ile   Leu   Gly   Glu   Ile   Ala   Val   Ser   Ile   Val   Arg   Ala   Leu   Glu   His>

790       795       800       805       810       815       820       825       830       835
       *                   *                   *                   *                   *
      CTG   CAC   AGC   AAG   CTG   TCG   GTG   ATC   CAC   AGA   GAT   GTG   AAG   CCC   TCC   AAT
      GAC   GTG   TCG   TTC   GAC   AGC   CAC   TAG   GTG   TCT   CTA   CAC   TTC   GGG   AGG   TTA
      Leu   His   Ser   Lys   Leu   Ser   Val   Ile   His   Arg   Asp   Val   Lys   Pro   Ser   Asn>

840       845       850       855       860       865       870       875       880
                     *                   *                   *                   *                   *
          GTC   CTT   ATC   AAC   AAG   GAG   GGC   CAT   GTG   AAG   ATG   TGT   GAC   TTT   GGC   ATC
          CAG   GAA   TAG   TTG   TTC   CTC   CCG   GTA   CAC   TTC   TAC   ACA   CTG   AAA   CCG   TAG
          Val   Leu   Ile   Asn   Lys   Glu   Gly   His   Val   Lys   Met   Cys   Asp   Phe   Gly   Ile>

885       890       895       900       905       910       915       920       925       930
                 *                   *                   *                   *                   *
      AGT   GGC   TAC   TTG   GTG   GAC   TCT   GTG   GCC   AAG   ACG   ATG   GAT   GCC   GGC   TGC
      TCA   CCG   ATG   AAC   CAC   CTG   AGA   CAC   CGG   TTC   TGC   TAC   CTA   CGG   CCG   ACG
      Ser   Gly   Tyr   Leu   Val   Asp   Ser   Val   Ala   Lys   Thr   Met   Asp   Ala   Gly   Cys>

935       940       945       950       955       960       965       970       975
                     *                   *                   *                   *
          AAG   CCC   TAC   ATG   GCC   CCT   GAG   AGG   ATC   AAC   CCA   GAG   CTG   AAC   CAG   AAG
          TTC   GGG   ATG   TAC   CGG   GGA   CTC   TCC   TAG   TTG   GGT   CTC   GAC   TTG   GTC   TTC
          Lys   Pro   Tyr   Met   Ala   Pro   Glu   Arg   Ile   Asn   Pro   Glu   Leu   Asn   Gln   Lys>

980       985       990       995       1000      1005      1010      1015      1020      1025
       *                   *                   *                   *                   *
      GGC   TAC   AAT   GTC   AAG   TCC   GAC   GTC   TGG   AGC   CTG   GGC   ATC   ACC   ATG   ATT
      CCG   ATG   TTA   CAG   TTC   AGG   CTG   CAG   ACC   TCG   GAC   CCG   TAG   TGG   TAC   TAA
      Gly   Tyr   Asn   Val   Lys   Ser   Asp   Val   Trp   Ser   Leu   Gly   Ile   Thr   Met   Ile>

1030      1035      1040      1045      1050      1055      1060      1065      1070      1075
                 *                   *                   *                   *                   *
      GAG   ATG   GCC   ATC   CTG   CGG   TTC   CCT   TAC   GAG   TCC   TGG   GGG   ACC   CCG   TTC
      CTC   TAC   CGG   TAG   GAC   GCC   AAG   GGA   ATG   CTC   AGG   ACC   CCC   TGG   GGC   AAG
      Glu   Met   Ala   Ile   Leu   Arg   Phe   Pro   Tyr   Glu   Ser   Trp   Gly   Thr   Pro   Phe>

```
           *         *         *         *         *
        CAG CAG CTG AAG CAG GTG GTG GAG GAG CCG TCC CCC CAG CTC CCA GCC
        GTC GTC GAC TTC GTC CAC CAC CTC CTC GGC AGG GGG GTC GAG GGT CGG
        Gln Gln Leu Lys Gln Val Val Glu Glu Pro Ser Pro Gln Leu Pro Ala>

1125  1130  1135  1140  1145  1150  1155  1160  1165  1170
           *         *         *         *         *
        GAC CGT TTC TCC CCC GAG TTT GTG GAC TTC ACT GCT CAG TGC CTG AGG
        CTG GCA AAG AGG GGG CTC AAA CAC CTG AAG TGA CGA GTC ACG GAC TCC
        Asp Arg Phe Ser Pro Glu Phe Val Asp Phe Thr Ala Gln Cys Leu Arg>

1175  1180  1185  1190  1195  1200  1205  1210  1215
           *         *         *         *
        AAG AAC CCC GCA GAG CGT ATG AGC TAC CTG GAG CTG ATG GAG CAC CCC
        TTC TTG GGG CGT CTC GCA TAC TCG ATG GAC CTC GAC TAC CTC GTG GGG
        Lys Asn Pro Ala Glu Arg Met Ser Tyr Leu Glu Leu Met Glu His Pro>

1220 1225  1230  1235  1240  1245  1250  1255  1260  1265
        *         *         *         *         *
        TTC TTC ACC TTG CAC AAA ACC AAG AAG ACG GAC ATT GCT GCC TTC GTG
        AAG AAG TGG AAC GTG TTT TGG TTC TTC TGC CTG TAA CGA CGG AAG CAC
        Phe Phe Thr Leu His Lys Thr Lys Lys Thr Asp Ile Ala Ala Phe Val>

1270  1275  1280  1285  1290  1295 1300  1305 1310  1315 1320
           *         *         *         *         *
        AAG AAG ATC CTG GGA GAA GAC TCA TAGGGGCTG GGCCTCGGAC CCCACTCCGG
        TTC TTC TAG GAC CCT CTT CTG AGT ATCCCCGAC CCGGAGCCTG GGGTGAGGCC
        Lys Lys Ile Leu Gly Glu Asp Ser>  (SEQ ID NO:2)

1325 1330  1335 1340  1345 1350  1355 1360  1365 1370  1375 1380
           *         *         *         *         *         *
        CCCTCCAGAG CCCCACAGCC CCATCTGCGG GGGCAGTGCT CACCCACACC ATAAGCTACT
        GGGAGGTCTC GGGGTGTCGG GGTAGACGCC CCCGTCACGA GTGGGTGTGG TATTCGATGA 1385 1390  1395 1400  1405 1410  1415 1420  1425 1430  1435 1440
           *         *         *         *         *         *
        GCCATCCTGG CCCAGGGCAT CTGGGAGGAA CCGAGGGGGC TGCTCCCACC TGGCTCTGTG
        CGGTAGGACC GGGTCCCGTA GACCCTCCTT GGCTCCCCCG ACGAGGGTGG ACCGAGACAC 1445 1450  1455 1460  1465 1470  1475 1480  1485 1490  1495 1500
           *         *         *         *         *         *
        GCGAGCCATT TGTCCCAAGT GCCAAAGAAG CAGACCATTG GGCTCCCAG  CCAGGCCCTT
        CGCTCGGTAA ACAGGGTTCA CGGTTTCTTC GTCTGGTAAC CCGAGGGTC  GGTCCGGGAA 1505 1510  1515 1520  1525 1530  1535 1540  1545 1550  1555 1560
           *         *         *         *         *         *
        GTCGGCCCCA CCAGTGCCTC TCCCTGCTGC TCCTAGGACC CGTCTCCAGC TGCTGAGATC
        CAGCCGGGGT GGTCACGGAG AGGGACGACG AGGATCCTGG GCAGAGGTCG ACGACTCTAG 1565 1570  1575 1580  1585 1590  1595 1600  1605 1610  1615 1620
           *         *         *         *         *         *
        CTGGACTGAG GGGGCCTGGA TGCCCCCTGT GGATGCTGCT GCCCCTGCAC AGCAGGCTGC
        GACCTGACTC CCCCGGACCT ACGGGGGACA CCTACGACGA CGGGGACGTG TCGTCCGACG 1625 1630  1635 1640  1645 1650  1655 1660  1665 1670  1675 1680
           *         *         *         *         *         *
        CAGTGCCTGG GTGGATGGGC CACCGCCTTG CCCAGCCTGG ATGCCATCCA AGTTGTATAT
        GTCACGGACC CACCTACCCG GTGGCGGAAC GGGTCGGACC TACGGTAGGT TCAACATATA 1685 1690  1695 1700  1705 1710  1715 1720  1725 1730  1735 1740
           *         *         *         *         *         *
        TTTTTTAATC TCTCGACTGA ATGGACTTTG CACACTTTGG CCCAGGGTGG CCACACCTCT
```

FIG. 4C

```
AAAAAATTAG AGAGCTGACT TACCTGAAAC GTGTGAAACC GGGTCCCACC GGTGTGGAGA 1745 1750  1755 1760  1765 1770  1775 1780  1785 1790  1795 1800
     *          *          *          *          *          *
ATCCCGGCTT TGGTGCGGGG TACACAAGAG GGGATGAGTT GTGTGAATAC CCCAAGACTC
TAGGGCCGAA ACCACGCCCC ATGTGTTCTC CCCTACTCAA CACACTTATG GGGTTCTGAG 1805 1810  1815 1820  1825 1830  1835 1840  1845 1850  1855 1860
     *          *          *          *          *          *
CCATGAGGGA GATGCCATGA GCCGCCCAAG GCCTTCCCCT GGCACTGGCA AACAGGGCCT
GGTACTCCCT CTACGGTACT CGGCGGGTTC CGGAAGGGGA CCGTGACCGT TTGTCCCGGA 1865 1870  1875 1880  1885 1890  1895 1900  1905 1910  1915 1920
     *          *          *          *          *          *
CTGCGGAGCA CACTGGCTCA CCCAGTCCTG CCCGCCACCG TTATCGGTGT CATTCACCTT
GACGCCTCGT GTGACCGAGT GGGTCAGGAC GGGCGGTGGC AATAGCCACA GTAAGTGGAA 1925 1930  1935 1940  1945 1950  1955 1960  1965 1970  1975 1980
     *          *          *          *          *          *
TCGTGTTTTT TTTAATTTAT CCTCTGTTGA TTTTTTCTTT TGCTTTATGG GTTTGGCTTG
AGCACAAAAA AAATTAAATA GGAGACAACT AAAAAAGAAA ACGAAATACC CAAACCGAAC 1985 1990  1995 2000  2005 2010  2015 2020  2025 2030
     *          *          *          *          *
TTTTTCTTGC ATGGTTTGGA GCTGATCGCT TCTCCCCCAC CCCCTAGGGG   (SEQ ID NO: 1)
AAAAAGAACG TACCAAACCT CGACTAGCGA AGAGGGGGTG GGGGATCCCC
```

FIG. 4D

```
              5         10        15        20        25        30        35        40        45        50        55        60
              *                   *                   *                   *                   *                   *
          T'AGCTGCAGC ACAGCCTTCC CTAACGTTGC AACTGGGGGA AAAATCACTT TCCAGTCTGT
           ATCGACGTCG TGTCGGAAGG GATTGCAACG TTGACCCCCT TTTTAGTGAA AGGTCAGACA 65        70        75        80        85        90        95       100       105       110       115       120
              *                   *                   *                   *                   *                   *
          TTTGCAAGGT GTGCATTTCC ATCTTGATTC CCTGAAAGTC CATCTGCTGC ATCGGTCAAG
          AAACGTTCCA CACGTAAAGG TAGAACTAAG GGACTTTCAG GTAGACGACG TAGCCAGTTC 125       130       135       140       145       150       155       160       165       170       175       180
              *                   *                   *                   *                   *                   *
          AGAAACTCCA CTTGCATGAA GATTGCACGC CTGCAGCTTG CATCTTTGTT GCAAAACTAG
          TCTTTGAGGT GAACGTACTT CTAACGTGCG GACGTCGAAC GTAGAAACAA CGTTTTGATC 185       190       195       200       205       210       215       220       225       230       235       240
              *                   *                   *                   *                   *                   *
          CTACAGAAGA GAAGCAAGGC AAAGTCTTTT GTGCTCCCCT CCCCCATCAA AGGAAAGGGG
          GATGTCTTCT CTTCGTTCCG TTTCAGAAAA CACGAGGGGA GGGGGTAGTT TCCTTTCCCC 245       250       255       260       265       270       275       280       285
              *                   *                   *                   *
          AAA ATG TCT CAG TCG AAA GGC AAG AAG CGA AAC CCT GGC CTT AAA ATT
          TTT TAC AGA GTC AGC TTT CCG TTC TTC GCT TTG GGA CCG GAA TTT TAA
              Met Ser Gln Ser Lys Gly Lys Lys Arg Asn Pro Gly Leu Lys Ile>

290       295       300       305       310       315       320       325       330       335
             *                   *                   *                   *                   *
          CCA AAA GAA GCA TTT GAA CAA CCT CAG ACC AGT TCC ACA CCA CCT AGA
          GGT TTT CTT CGT AAA CTT GTT GGA GTC TGG TCA AGG TGT GGT GGA TCT
          Pro Lys Glu Ala Phe Glu Gln Pro Gln Thr Ser Ser Thr Pro Pro Arg>

340       345       350       355       360       365       370       375       380
             *                   *                   *                   *                   *
          GAT TTA GAC TCC AAG GCT TGC ATT TCT ATT GGA AAT CAG AAC TTT GAG
          CTA AAT CTG AGG TTC CGA ACG TAA AGA TAA CCT TTA GTC TTG AAA CTC
          Asp Leu Asp Ser Lys Ala Cys Ile Ser Ile Gly Asn Gln Asn Phe Glu>

385       390       395       400       405       410       415       420       425       430
             *                   *                   *                   *                   *
          GTG AAG GCA GAT GAC CTG GAG CCT ATA ATG GAA CTG GGA CGA GGT GCG
          CAC TTC CGT CTA CTG GAC CTC GGA TAT TAC CTT GAC CCT GCT CCA CGC
          Val Lys Ala Asp Asp Leu Glu Pro Ile Met Glu Leu Gly Arg Gly Ala>

435       440       445       450       455       460       465       470       475       480
             *                   *                   *                   *                   *
          TAC GGG GTG GTG GAG AAG ATG CGG CAC GTG CCC AGC GGG CAG ATC ATG
          ATG CCC CAC CAC CTC TTC TAC GCC GTG CAC GGG TCG CCC GTC TAG TAC
          Tyr Gly Val Val Glu Lys Met Arg His Val Pro Ser Gly Gln Ile Met>

485       490       495       500       505       510       515       520       525
             *                   *                   *                   *
          GCA GTG AAG CGG ATC CGA GCC ACA GTA AAT AGC CAG GAA CAG AAA CGG
          CGT CAC TTC GCC TAG GCT CGG TGT CAT TTA TCG GTC CTT GTC TTT GCC
          Ala Val Lys Arg Ile Arg Ala Thr Val Asn Ser Gln Glu Gln Lys Arg>

530       535       540       545       550       555       560       565       570       575
             *                   *                   *                   *                   *
          CTA CTG ATG GAT TTG GAT ATT TCC ATG AGG ACG GTG GAC TGT CCA TTC
          GAT GAC TAC CTA AAC CTA TAA AGG TAC TCC TGC CAC CTG ACA GGT AAG
```

FIG. 5A

```
                Leu Leu Met Asp Leu Asp Ile Ser Met Arg Thr Val Asp Cys Pro Phe>

580     585     590     595     600     605     610     615     620
                *               *               *               *               *
       ACT GTC ACC TTT TAT GGC GCA CTG TTT CGG GAG GGT GAT GTG TGG ATC
       TGA CAG TGG AAA ATA CCG CGT GAC AAA GCC CTC CCA CTA CAC ACC TAG
       Thr Val Thr Phe Tyr Gly Ala Leu Phe Arg Glu Gly Asp Val Trp Ile>

625     630     635     640     645     650     655     660     665     670
   *               *               *               *               *
 TGC ATG GAG CTC ATG GAT ACA TCA CTA GAT AAA TTC TAC AAA CAA GTT
 ACG TAC CTC GAG TAC CTA TGT AGT GAT CTA TTT AAG ATG TTT GTT CAA
 Cys Met Glu Leu Met Asp Thr Ser Leu Asp Lys Phe Tyr Lys Gln Val>

675     680     685     690     695     700     705     710     715     720
                *               *               *               *               *
       ATT GAT AAA GGC CAG ACA ATT CCA GAG GAC ATC TTA GGG AAA ATA GCA
       TAA CTA TTT CCG GTC TGT TAA GGT CTC CTG TAG AAT CCC TTT TAT CGT
       Ile Asp Lys Gly Gln Thr Ile Pro Glu Asp Ile Leu Gly Lys Ile Ala>

725     730     735     740     745     750     755     760     765
                    *               *               *               *
          GTT TCT ATT GTA AAA GCA TTA GAA CAT TTA CAT AGT AAG CTG TCT GTC
          CAA AGA TAA CAT TTT CGT AAT CTT GTA AAT GTA TCA TTC GAC AGA CAG
          Val Ser Ile Val Lys Ala Leu Glu His Leu His Ser Lys Leu Ser Val>

770     775     780     785     790     795     800     805     810     815
   *               *               *               *               *
 ATT CAC AGA GAC GTC AAG CCT TCT AAT GTA CTC ATC AAT GCT CTC GGT
 TAA GTG TCT CTG CAG TTC GGA AGA TTA CAT GAG TAG TTA CGA GAG CCA
 Ile His Arg Asp Val Lys Pro Ser Asn Val Leu Ile Asn Ala Leu Gly>

820     825     830     835     840     845     850     855     860
                *               *               *               *               *
       CAA GTG AAG ATG TGC GAT TTT GGA ATC AGT GGC TAC TTG GTG GAC TCT
       GTT CAC TTC TAC ACG CTA AAA CCT TAG TCA CCG ATG AAC CAC CTG AGA
       Gln Val Lys Met Cys Asp Phe Gly Ile Ser Gly Tyr Leu Val Asp Ser>

865     870     875     880     885     890     895     900     905     910
   *               *               *               *               *
 GTT GCT AAA ACA ATT GAT GCA GGT TGC AAA CCA TAC ATG GCC CCT GAA
 CAA CGA TTT TGT TAA CTA CGT CCA ACG TTT GGT ATG TAC CGG GGA CTT
 Val Ala Lys Thr Ile Asp Ala Gly Cys Lys Pro Tyr Met Ala Pro Glu>

915     920     925     930     935     940     945     950     955     960
                *               *               *               *               *
       AGA ATA AAC CCA GAG CTC AAC CAG AAG GGA TAC AGT GTG AAG TCT GAC
       TCT TAT TTG GGT CTC GAG TTG GTC TTC CCT ATG TCA CAC TTC AGA CTG
       Arg Ile Asn Pro Glu Leu Asn Gln Lys Gly Tyr Ser Val Lys Ser Asp>

965     970     975     980     985     990     995    1000    1005
                    *               *               *               *
          ATT TGG AGT CTG GGC ATC ACG ATG ATT GAG TTG GCC ATC CTT CGA TTT
          TAA ACC TCA GAC CCG TAG TGC TAC TAA CTC AAC CGG TAG GAA GCT AAA
          Ile Trp Ser Leu Gly Ile Thr Met Ile Glu Leu Ala Ile Leu Arg Phe>

1010    1015    1020    1025    1030    1035    1040    1045    1050    1055
   *               *               *               *               *
 CCC TAT GAT TCA TGG GGA ACT CCA TTT CAG CAG CTC AAA CAG GTG GTA
 GGG ATA CTA AGT ACC CCT TGA GGT AAA GTC GTC GAG TTT GTC CAC CAT
 Pro Tyr Asp Ser Trp Gly Thr Pro Phe Gln Gln Leu Lys Gln Val Val>
```

FIG. 5B

```
      1060      1065      1070      1075      1080      1085      1090      1095      1100
        *                   *                   *                   *                   *
      GAG GAG   CCA TCG   CCA CAA   CTC CCA   GCA GAC   AAG TTC   TCT GCA   GAG TTT
      CTC CTC   GGT AGC   GGT GTT   GAG GGT   CGT CTG   TTC AAG   AGA CGT   CTC AAA
      Glu Glu   Pro Ser   Pro Gln   Leu Pro   Ala Asp   Lys Phe   Ser Ala   Glu Phe>

1105      1110      1115      1120      1125      1130      1135      1140      1145      1150
    *                   *                   *                   *                   *
  GTT GAC   TTT ACC   TCA CAG   TGC TTA   AAG AAG   AAT TCC   AAA GAA   CGG CCT
  CAA CTG   AAA TGG   AGT GTC   ACG AAT   TTC TTC   TTA AGG   TTT CTT   GCC GGA
  Val Asp   Phe Thr   Ser Gln   Cys Leu   Lys Lys   Asn Ser   Lys Glu   Arg Pro>

1155      1160      1165      1170       1175      1180      1185      1190      1195      1200
    *                   *                    *                   *                   *
  ACA TAC   CCA GAG   CTA ATG   CAA CAT   CCA TTT   TTC ACC   CTA CAT   GAA TCC
  TGT ATG   GGT CTC   GAT TAC   GTT GTA   GGT AAA   AAG TGG   GAT GTA   CTT AGG
  Thr Tyr   Pro Glu   Leu Met   Gln His   Pro Phe   Phe Thr   Leu His   Glu Ser>

1205      1210      1215      1220      1225      1230      1235      1240      1245      1250
         *                   *                   *                   *                   *
       AAA GGA   ACA GAT   GTG GCA   TCT TTT   GTA AAA   CTG ATT   CTT GGA   GAC TAAAA
       TTT CCT   TGT CTA   CAC CGT   AGA AAA   CAT TTT   GAC TAA   GAA CCT   CTG ATTTT
       Lys Gly   Thr Asp   Val Ala   Ser Phe   Val Lys   Leu Ile   Leu Gly   Asp> (SEQ ID NO: 4)

1255 1260   1265 1270   1275 1280   1285 1290   1295 1300   1305 1310
       *            *            *            *            *            *
    AGCAGTGGAC   TTAATCGGTT   GACCCTACTG   TGGATTGGTG   GGTTTCGGGG   TGAAGCAAGT
    TCGTCACCTG   AATTAGCCAA   CTGGGATGAC   ACCTAACCAC   CCAAAGCCCC   ACTTCGTTCA 1315 1320   1325 1330   1335 1340   1345 1350   1355 1360   1365 1370
       *            *            *            *            *            *
    TCACTACAGC   ATCAATAGAA   AGTCATCTTT   GAGATAATTT   AACCCTGCCT   CTCAGAGGGT
    AGTGATGTCG   TAGTTATCTT   TCAGTAGAAA   CTCTATTAAA   TTGGGACGGA   GAGTCTCCCA 1375 1380   1385 1390   1395 1400   1405 1410   1415 1420   1425 1430
       *            *            *            *            *            *
    TTTCTCTCCC   AATTTTCTTT   TTACTCCCCC   TCTTAAGGGG   GCCTTGGAAT   CTATAGTATA
    AAAGAGAGGG   TTAAAAGAAA   AATGAGGGGG   AGAATTCCCC   CGGAACCTTA   GATATCATAT 1435 1440   1445 1450   1455 1460   1465 1470   1475 1480   1485 1490
       *            *            *            *            *            *
    GAATGAACTG   TCTAGATGGA   TGAATTATGA   TAAAGGCTTA   GGACTTCAAA   AGGTGATTAA
    CTTACTTGAC   AGATCTACCT   ACTTAATACT   ATTTCCGAAT   CCTGAAGTTT   TCACTAATT 1495 1500   1505 1510   1515 1520   1525 1530   1535 1540   1545 1550
       *            *            *            *            *            *
    ATATTTAATG   ATGTGTCATA   TGAGTCCTCA   AAAAAAAAAA   AAAAAAAAAA   AAAAAAAAAA
    TATAAATTAC   TACACAGTAT   ACTCAGGAGT   TTTTTTTTTT   TTTTTTTTTT   TTTTTTTTTT 1555 1560   1565 1570   1575 1580   1585 1590   1595 1600
       *            *            *            *            *
    AAAAAAAAAA   AAAAAAAAAA   AAAAAAAAAA   AAAAAAAAAA   AAAAAAAAAA   AA (SEQ ID NO: 3)
    TTTTTTTTTT   TTTTTTTTTT   TTTTTTTTTT   TTTTTTTTTT   TTTTTTTTTT   TT
```

FIG. 5C

```
            5          10         15         20         25         30         35         40         45         50         55
                        *                     *                     *                     *                     *
           CTAGGGTCCC CGGCGCCAGG CCACCCGGCC GTCAGCAGC ATG CAG GGT AAA CGC AAA
           GATCCCAGGG GCCGCGGTCC GGTGGGCCGG CAGTCGTCG TAC GTC CCA TTT GCG TTT
                                                      Met Gln Gly Lys Arg Lys>

60         65         70         75         80         85         90         95         100        105
            *                     *                     *                     *                     *
           GCA CTG AAG TTG AAT TTT GCA AAT CCA CCT TTC AAA TCT ACA GCA AGG
           CGT GAC TTC AAC TTA AAA CGT TTA GGT GGA AAG TTT AGA TGT CGT TCC
           Ala Leu Lys Leu Asn Phe Ala Asn Pro Pro Phe Lys Ser Thr Ala Arg>

110        115        120        125        130        135        140        145        150
                                  *                     *                     *                     *                     *
           TTT ACT CTG AAT CCC AAT CCT ACA GGA GTT CAA AAC CCA CAC ATA GAG
           AAA TGA GAC TTA GGG TTA GGA TGT CCT CAA GTT TTG GGT GTG TAT CTC
           Phe Thr Leu Asn Pro Asn Pro Thr Gly Val Gln Asn Pro His Ile Glu>

155        160        165        170        175        180        185        190        195        200
                        *                     *                     *                     *                     *
           AGA CTG AGA ACA CAC AGC ATT GAG TCA TCA GGA AAA CTG AAG ATC TCC
           TCT GAC TCT TGT GTG TCG TAA CTC AGT AGT CCT TTT GAC TTC TAG AGG
           Arg Leu Arg Thr His Ser Ile Glu Ser Ser Gly Lys Leu Lys Ile Ser>

205        210        215        220        225        230        235        240        245
                                  *                     *                     *                     *
           CCT GAA CAA CAC TGG GAT TTC ACT GCA GAG GAC TTG AAA GAC CTT GGA
           GGA CTT GTT GTG ACC CTA AAG TGA CGT CTC CTG AAC TTT CTG GAA CCT
           Pro Glu Gln His Trp Asp Phe Thr Ala Glu Asp Leu Lys Asp Leu Gly>

250        255        260        265        270        275        280        285        290        295
             *                     *                     *                     *                     *
           GAA ATT GGA CGA GGA GCT TAT GGT TCT GTC AAC AAA ATG GTC CAC AAA
           CTT TAA CCT GCT CCT CGA ATA CCA AGA CAG TTG TTT TAC CAG GTG TTT
           Glu Ile Gly Arg Gly Ala Tyr Gly Ser Val Asn Lys Met Val His Lys>

300        305        310        315        320        325        330        335        340        345
                                  *                     *                     *                     *                     *
           CCA AGT GGG CAA ATA ATG GCA GTT AAA AGA ATT CGG TCA ACA GTG GAT
           GGT TCA CCC GTT TAT TAC CGT CAA TTT TCT TAA GCC AGT TGT CAC CTA
           Pro Ser Gly Gln Ile Met Ala Val Lys Arg Ile Arg Ser Thr Val Asp>

350        355        360        365        370        375        380        385        390
                                  *                     *                     *                     *
           GAA AAA GAA CAA AAA CAA CTT CTT ATG GAT TTG GAT GTA GTA ATG CGG
           CTT TTT CTT GTT TTT GTT GAA GAA TAC CTA AAC CTA CAT CAT TAC GCC
           Glu Lys Glu Gln Lys Gln Leu Leu Met Asp Leu Asp Val Val Met Arg>

395        400        405        410        415        420        425        430        435        440
                        *                     *                     *                     *                     *
           AGT AGT GAT TGC CCA TAC ATT GTT CAG TTT TAT GGT GCA CTC TTC AGA
           TCA TCA CTA ACG GGT ATG TAA CAA GTC AAA ATA CCA CGT GAG AAG TCT
           Ser Ser Asp Cys Pro Tyr Ile Val Gln Phe Tyr Gly Ala Leu Phe Arg>

445        450        455        460        465        470        475        480        485
                                  *                     *                     *                     *
           GAG GGT GAC TGT TGG ATC TGT ATG GAA CTC ATG TCT ACC TCG TTT GAT
           CTC CCA CTG ACA ACC TAG ACA TAC CTT GAG TAC AGA TGG AGC AAA CTA
           Glu Gly Asp Cys Trp Ile Cys Met Glu Leu Met Ser Thr Ser Phe Asp>
```

FIG. 6A

```
      490     495     500     505     510     515     520     525     530     535
       *               *               *               *               *
      AAG TTT TAC AAA TAT GTA TAT AGT GTA TTA GAT GAT GTT ATT CCA GAA
      TTC AAA ATG TTT ATA CAT ATA TCA CAT AAT CTA CTA CAA TAA GGT CTT
      Lys Phe Tyr Lys Tyr Val Tyr Ser Val Leu Asp Asp Val Ile Pro Glu>

540     545     550     555     560     565     570     575     580     585
       *               *               *               *               *
      GAA ATT TTA GGC AAA ATC ACT TTA GCA ACT GTG AAA GCA CTA AAC CAC
      CTT TAA AAT CCG TTT TAG TGA AAT CGT TGA CAC TTT CGT GAT TTG GTG
      Glu Ile Leu Gly Lys Ile Thr Leu Ala Thr Val Lys Ala Leu Asn His>

590     595     600     605     610     615     620     625     630
           *               *               *               *               *
      TTA AAA GAA AAC TTG AAA ATT ATT CAC AGA GAT ATC AAA CCT TCC AAT
      AAT TTT CTT TTG AAC TTT TAA TAA GTG TCT CTA TAG TTT GGA AGG TTA
      Leu Lys Glu Asn Leu Lys Ile Ile His Arg Asp Ile Lys Pro Ser Asn>

635     640     645     650     655     660     665     670     675     680
                       *               *               *               *       *
      ATT CTT CTG GAC AGA AGT GGA AAT ATT AAG CTC TGT GAC TTC GGC ATC
      TAA GAA GAC CTG TCT TCA CCT TTA TAA TTC GAG ACA CTG AAG CCG TAG
      Ile Leu Leu Asp Arg Ser Gly Asn Ile Lys Leu Cys Asp Phe Gly Ile>

685     690     695     700     705     710     715     720     725
                           *               *               *               *
      AGT GGA CAG CTT GTG GAC TCT ATT GCC AAG ACA AGA GAT GCT GGC TGT
      TCA CCT GTC GAA CAC CTG AGA TAA CGG TTC TGT TCT CTA CGA CCG ACA
      Ser Gly Gln Leu Val Asp Ser Ile Ala Lys Thr Arg Asp Ala Gly Cys>

730     735     740     745     750     755     760     765     770     775
       *               *               *               *       *
      AGG CCA TAC ATG GCA CCT GAA AGA ATA GAC CCA AGC GCA TCA CGA CAA
      TCC GGT ATG TAC CGT GGA CTT TCT TAT CTG GGT TCG CGT AGT GCT GTT
      Arg Pro Tyr Met Ala Pro Glu Arg Ile Asp Pro Ser Ala Ser Arg Gln>

780     785     790     795     800     805     810     815     820     825
           *               *               *               *               *
      GGA TAT GAT GTC CGC TCT GAT GTC TGG AGT TTG GGA ATC ACA TTG TAT
      CCT ATA CTA CAG GCG AGA CTA CAG ACC TCA AAC CCT TAG TGT AAC ATA
      Gly Tyr Asp Val Arg Ser Asp Val Trp Ser Leu Gly Ile Thr Leu Tyr>

830     835     840     845     850     855     860     865     870
           *               *               *               *
      GAG TTG GCC ACA GGC CGA TTT CCT TAT CCA AAG TGG AAT AGT GTA TTT
      CTC AAC CGG TGT CCG GCT AAA GGA ATA GGT TTC ACC TTA TCA CAT AAA
      Glu Leu Ala Thr Gly Arg Phe Pro Tyr Pro Lys Trp Asn Ser Val Phe>

875     880     885     890     895     900     905     910     915     920
                       *               *               *               *       *
      GAT CAA CTA ACA CAA GTC GTG AAA GGA GAT CCT CCG CAG CTG AGT AAT
      CTA GTT GAT TGT GTT CAG CAC TTT CCT CTA GGA GGC GTC GAC TCA TTA
      Asp Gln Leu Thr Gln Val Val Lys Gly Asp Pro Pro Gln Leu Ser Asn>

925     930     935     940     945     950     955     960     965
                           *               *               *               *
      TCT GAG GAA AGG GAA TTC TCC CCG AGT TTC ATC AAC TTT GTC AAC TTG
      AGA CTC CTT TCC CTT AAG AGG GGC TCA AAG TAG TTG AAA CAG TTG AAC
      Ser Glu Glu Arg Glu Phe Ser Pro Ser Phe Ile Asn Phe Val Asn Leu>

```
TGC CTT ACG AAG GAT GAA TCC AAA AGG CCA AAG TAT AAA GAG CTT CTG
ACG GAA TGC TTC CTA CTT AGG TTT TCC GGT TTC ATA TTT CTC GAA GAC
Cys Leu Thr Lys Asp Glu Ser Lys Arg Pro Lys Tyr Lys Glu Leu Leu>

1020      1025      1030      1035      1040      1045      1050      1055      1060      1065
   *                   *                    *                    *                    *
AAA CAT CCC TTT ATT TTG ATG TAT GAA GAA CGT GCC GTT GAG GTC GCA
TTT GTA GGG AAA TAA AAC TAC ATA CTT CTT GCA CGG CAA CTC CAG CGT
Lys His Pro Phe Ile Leu Met Tyr Glu Glu Arg Ala Val Glu Val Ala>

1070      1075      1080      1085      1090 1095      1100      1105      1110
         *                    *                    *                    *                    *
TGC TAT GTT TGT AAA ATC CTG GAT CAA ATG CCA GCT ACT CCC AGC TCT
ACG ATA CAA ACA TTT TAG GAC CTA GTT TAC GGT CGA TGA GGG TCG AGA
Cys Tyr Val Cys Lys Ile Leu Asp Gln Met Pro Ala Thr Pro Ser Ser>

1115      1120      1125      1130      1135 1140      1145 1150      1155 1160      1165 1170
   *                   *                    *                    *                    *
CCC ATG TAT GTC GAT TG ATATCGYTGC TACATCAGAC TCTAGAAAAA AGGGCTGAGA
GGG TAC ATA CAG CTA AC TATAGCRACG ATGTAGTCTG AGATCTTTTT TCCCGACTCT
Pro Met Tyr Val Asp>  (SEQ ID NO:6)

1175 1180 1185 1190 1195 1200 1205 1210 1215 1220 1225 1230
   *         *         *         *         *         *
GGAAGCAAGA CGTAAAGAAT TTTCATCCCG TATCACAGTG TTTTTATTGC TCGCCCAGAC
CCTTCGTTCT GCATTTCTTA AAAGTAGGGC ATAGTGTCAC AAAAATAACG AGCGGGTCTG 1235 1240 1245 1250 1255 1260 1265 1270 1275 1280 1285 1290
   *         *         *         *         *         *
ACCATGTGCA ATAAGATTGG TGTTCGTTTC CATCATGTCT GTATACTCCT GTCACCTAGA
TGGTACACGT TATTCTAACC ACAAGCAAAG GTAGTACAGA CATATGAGGA CAGTGGATCT 1295 1300 1305 1310 1315 1320 1325 1330 1335 1340 1345 1350
   *         *         *         *         *         *
ACGTGCATCC TTGTAATACC TGATTGATCA CACAGTGTTA GTGCTGGTCA GAGAGACCTC
TGCACGTAGG AACATTATGG ACTAACTAGT GTGTCACAAT CACGACCAGT CTCTCTGGAG 1355 1360 1365 1370 1375 1380 1385 1390 1395 1400 1405 1410
   *         *         *         *         *         *
ATCCTGCTCT TTTGTGATGA ACATATTCAT GAAATGTGGA AGTCAGTACG ATCAAGTTGT
TAGGACGAGA AAACACTACT TGTATAAGTA CTTTACACCT TCAGTCATGC TAGTTCAACA 1415 1420 1425 1430 1435 1440 1445 1450 1455 1460 1465 1470
   *         *         *         *         *         *
TGACTGTGAT TAGATCACAT CTTAAATTCA TTTCTAGACT CAAAACCTGG AGATGCAGCT
ACTGACACTA ATCTAGTGTA GAATTTAAGT AAAGATCTGA GTTTTGGACC TCTACGTCGA 1475 1480 1485 1490 1495 1500 1505 1510 1515 1520 1525 1530
   *         *         *         *         *         *
ACTGGAATGG TGTTTTGTCA GACTTCCAAA TCCTGGAAGG ACACAGTGAT GAATGTACTA
TGACCTTACC ACAAAACAGT CTGAAGGTTT AGGACCTTCC TGTGTCACTA CTTACATGAT 1535 1540 1545 1550 1555 1560 1565 1570 1575 1580 1585 1590
   *         *         *         *         *         *
TATCTGAACA TAGAAACTCG GGCTTGAGTG AGAAGAGCTT GCACAGCCAA CGAGACACAT
ATAGACTTGT ATCTTTGAGC CCGAACTCAC TCTTCTCGAA CGTGTCGGTT GCTCTGTGTA 1595 1600 1605 1610 1615 1620 1625 1630 1635 1640 1645 1650
   *         *         *         *         *         *
TGCCTTCTGG AGCTGGGAGA CAAAGGAGGA ATTTACTTTC TTCACCAAGT GCAATAGATT
ACGGAAGACC TCGACCCTCT GTTTCCTCCT TAAATGAAAG AAGTGGTTCA CGTTATCTAA
```

FIG. 6C

```
     1655 1660   1665 1670   1675 1680   1685 1690   1695 1700   1705 1710
        *           *           *           *           *           *
     ACTGATGTGA  TATTCTGTTG  CTTTACAGTT  ACAGTTGATG  TTTGGGGATC  GATGTGCTCA
     TGACTACACT  ATAAGACAAC  GAAATGTCAA  TGTCAACTAC  AAACCCCTAG  CTACACGAGT 1715 1720   1725 1730   1735 1740   1745 1750   1755 1760   1765 1770
        *           *           *           *           *           *
     GCCAAATTTC  CTGTTTGAAA  TATCATGTTA  AATTAGAATG  AATTTATCTT  TACCAAAAAC
     CGGTTTAAAG  GACAAACTTT  ATAGTACAAT  TTAATCTTAC  TTAAATAGAA  ATGGTTTTTG 1775 1780   1785 1790   1795 1800   1805 1810   1815 1820   1825 1830
        *           *           *           *           *           *
     CATGTTGCGT  TCAAAGAGGT  GAACATTAAA  ATATAGAGAC  AGGACAGAAT  GTGTTCTTTT
     GTACAACGCA  AGTTTCTCCA  CTTGTAATTT  TATATCTCTG  TCCTGTCTTA  CACAAGAAAA 1835 1840   1845 1850   1855 1860   1865 1870   1875 1880   1885 1890
        *           *           *           *           *           *
     CTCCTCTACC  AGTCCTATTT  TTCAATGGGA  AGACTCAGGA  GTCTGCCACT  TGTCAAAGAA
     GAGGAGATGG  TCAGGATAAA  AAGTTACCCT  TCTGAGTCCT  CAGACGGTGA  ACAGTTTCTT 1895 1900   1905 1910   1915 1920   1925 1930   1935 1940   1945 1950
        *           *           *           *           *           *
     GGTGCTGATC  CTAAGAATTT  TTCATTCTCA  GAATTCGGTG  TGCTGCCAAC  TTGATGTTCC
     CCACGACTAG  GATTCTTAAA  AAGTAAGAGT  CTTAAGCCAC  ACGACGGTTG  AACTACAAGG 1955 1960   1965 1970   1975 1980   1985 1990   1995 2000   2005 2010
        *           *           *           *           *           *
     ACCTGCCACA  AACCACCAGG  ACTGAAAGAA  GAAAACAGTA  CAGAAGGCAA  AGTTTACAGA
     TGGACGGTGT  TTGGTGGTCC  TGACTTTCTT  CTTTTGTCAT  GTCTTCCGTT  TCAAATGTCT 2015 2020   2025 2030   2035 2040   2045 2050   2055 2060   2065 2070
        *           *           *           *           *           *
     TGTTTTTAAT  TCTAGTATTT  TATCTGGAAC  AACTTGTAGC  AGCTATATAT  TTCCCCTTGG
     ACAAAAATTA  AGATCATAAA  ATAGACCTTG  TTGAACATCG  TCGATATATA  AAGGGGAACC 2075 2080   2085 2090   2095 2100   2105 2110   2115 2120   2125 2130
        *           *           *           *           *           *
     TCCCAAGCCT  GATACTTTAG  CCATCATAAC  TCACTAACAG  GGAGAAGTAG  CTAGTAGCAA
     AGGGTTCGGA  CTATGAAATC  GGTAGTATTG  AGTGATTGTC  CCTCTTCATC  GATCATCGTT 2135 2140   2145 2150   2155 2160   2165 2170   2175 2180   2185 2190
        *           *           *           *           *           *
     TGTGCCTTGA  TTGATTAGAT  AAAGATTTCT  AGTAGGCAGC  AAAAGACCAA  ATCTCAGTTG
     ACACGGAACT  AACTAATCTA  TTTCTAAAGA  TCATCCGTCG  TTTTCTGGTT  TAGAGTCAAC 2195 2200   2205 2210   2215 2220   2225 2230   2235 2240   2245 2250
        *           *           *           *           *           *
     TTTGCTTCTT  GCCATCACTG  GTCCAGGTCT  TCAGTTTCCG  AATCTCTTTC  CCTTCCCCTG
     AAACGAAGAA  CGGTAGTGAC  CAGGTCCAGA  AGTCAAAGGC  TTAGAGAAAG  GGAAGGGGAC 2255 2260   2265 2270   2275 2280   2285 2290   2295 2300   2305 2310
        *           *           *           *           *           *
     TGGTCTATTG  TCGCTATGTG  ACTTGCGCTT  AATCCAATAT  TTTGCCTTTT  TTCTATATCA
     ACCAGATAAC  AGCGATACAC  TGAACGCGAA  TTAGGTTATA  AAACGGAAAA  AAGATATAGT 2315 2320   2325 2330   2335 2340   2345 2350   2355 2360   2365 2370
        *           *           *           *           *           *
     AAAAACCTTT  ACAGTTAGCA  GGGATGTTCC  TTACCGAGGA  TTTTTAACCC  CCAATCTCTC
     TTTTTGGAAA  TGTCAATCGT  CCCTACAAGG  AATGGCTCCT  AAAAATTGGG  GGTTAGAGAG 2375 2380   2385 2390   2395 2400   2405 2410   2415 2420   2425 2430
        *           *           *           *           *           *
```

FIG. 6D

```
ATAATCGCTA GTGTTTAAAA GGCTAAGAAT AGTGGGGCCC AACCGATGTG GTAGGTGATA
TATTAGCGAT CACAAATTTT CCGATTCTTA TCACCCCGGG TTGGCTACAC CATCCACTAT
    2435 2440  2445 2450  2455 2460  2465 2470  2475 2480  2485 2490
              *          *          *          *          *          *
AAGAGGCATC TTTTCTAGAG ACACATTGGA CCAGATGAGG ATCCGAAACG GCAGCCTTTA
TTCTCCGTAG AAAAGATCTC TGTGTAACCT GGTCTACTCC TAGGCTTTGC CGTCGGAAAT
    2495 2500  2505 2510  2515 2520  2525 2530  2535 2540  2545 2550
              *          *          *          *          *          *
CGTTCATCAC CTGCTAGAAC CTCTCGTAGT CCATCACCAT TTCTTGGCAT TGGAATTCTA
GCAAGTAGTG GACGATCTTG GAGAGCATCA GGTAGTGGTA AAGAACCGTA ACCTTAAGAT
    2555 2560  2565 2570  2575 2580  2585 2590  2595 2600  2605 2610
              *          *          *          *          *          *
CTGGAAAAAA ATACAAAAAG CAAAACAAAA CCCTCAGCAC TGTTACAAGA GGCCATTTAA
GACCTTTTTT TATGTTTTTC GTTTTGTTTT GGGAGTCGTG ACAATGTTCT CCGGTAAATT
    2615 2620  2625 2630  2635 2640  2645 2650  2655 2660  2665 2670
              *          *          *          *          *          *
GTATCTTGTG CTTCTTCACT TACCCATTAG CCAGGTTCTC ATTAGGTTTT GCTTGGGCCT
CATAGAACAC GAAGAAGTGA ATGGGTAATC GGTCCAAGAG TAATCCAAAA CGAACCCGGA
    2675 2680  2685 2690  2695 2700  2705 2710  2715 2720  2725 2730
              *          *          *          *          *          *
CCCTGGCACT GAACCTTAGG CTTTGTATGA CAGTGAAGCA GCACTGTGAG TGGTTCAAGC
GGGACCGTGA CTTGGAATCC GAAACATACT GTCACTTCGT CGTGACACTC ACCAAGTTCG
    2735 2740  2745 2750  2755 2760  2765 2770  2775 2780  2785 2790
              *          *          *          *          *          *
ACACTGGAAT ATAAAACAGT CATGGCCTGA GATGCAGGTG ATGCCATTAC AGAACCAAAT
TGTGACCTTA TATTTTGTCA GTACCGGACT CTACGTCCAC TACGGTAATG TCTTGGTTTA
    2795 2800  2805 2810  2815 2820  2825 2830  2835 2840  2845 2850
              *          *          *          *          *          *
CGTGGCACGT ATTGCTGTGT CTCCTCTCAG AGTGACAGTC ATAAATACTG TCAAACAATA
GCACCGTGCA TAACGACACA GAGGAGAGTC TCACTGTCAG TATTTATGAC AGTTTGTTAT
    2855 2860  2865 2870  2875 2880  2885 2890  2895 2900  2905 2910
              *          *          *          *          *          *
AAGGGAGAAT GGTGCTGTTT AAAGTCACAT CCCTGTAAAT TGCAGAATTC AAAAGTGATT
TTCCCTCTTA CCACGACAAA TTTCAGTGTA GGGACATTTA ACGTCTTAAG TTTTCACTAA
    2915 2920  2925 2930  2935 2940  2945 2950  2955 2960  2965 2970
              *          *          *          *          *          *
ATCTCTTTGA TCTACTTGCC TCATTTCCCT ATCTTCTCCC CCACGGTATC CTAAACTTTA
TAGAGAAACT AGATGAACGG AGTAAAGGGA TAGAAGAGGG GGTGCCATAG GATTTGAAAT
    2975 2980  2985 2990  2995 3000  3005 3010  3015 3020  3025 3030
              *          *          *          *          *          *
GACTTCCCAC TGTTCTGAAA GGAGACATTG CTCTATGTCT GCCTTCGACC ACAGCAAGCC
CTGAAGGGTG ACAAGACTTT CCTCTGTAAC GAGATACAGA CGGAAGCTGG TGTCGTTCGG
    3035 3040  3045 3050  3055 3060  3065 3070  3075 3080  3085 3090
              *          *          *          *          *          *
ATCATCCTCC ATTGCTCCCG GGGACTCAAG AGGAATCTGT TTCTCTGCTG TCAACTTCCC
TAGTAGGAGG TAACGAGGGC CCCTGAGTTC TCCTTAGACA AAGAGACGAC AGTTGAAGGG
    3095 3100  3105 3110  3115 3120  3125 3130  3135 3140  3145 3150
              *          *          *          *          *          *
ATCTGGCTCA GCATAGGGTC ACTTTGCCAT TATGCAAATG GAGATAAAAG CAATTCTGGC
TAGACCGAGT CGTATCCCAG TGAAACGGTA ATACGTTTAC CTCTATTTTC GTTAAGACCG
```

FIG. 6E

```
3155 3160   3165 3170  -3175 3180   3185 3190   3195 3200   3205 3210
     *           *           *           *           *           *
TGTCCAGGAG  CTAATCTGAC  CGTTCTATTG  TGTGGATGAC  CACATAAGAA  GGCAATTTTA
ACAGGTCCTC  GATTAGACTG  GCAAGATAAC  ACACCTACTG  GTGTATTCTT  CCGTTAAAAT 3215 3220   3225 3230   3235 3240   3245 3250   3255 3260   3265 3270
     *           *           *           *           *           *
GTGTATTAAT  CATAGATTAT  TATAAACTAT  AAACTTAAGG  GCAAGGAGTT  TATTACAATG
CACATAATTA  GTATCTAATA  ATATTTGATA  TTTGAATTCC  CGTTCCTCAA  ATAATGTTAC 3275 3280   3285 3290   3295 3300   3305 3310   3315 3320   3325 3330
     *           *           *           *           *           *
TATCTTTATT  AAAACAAAAG  GGTGTATAGT  GTTCACAAAC  TGTGAAAATA  GTGTAAGAAC
ATAGAAATAA  TTTTGTTTTC  CCACATATCA  CAAGTGTTTG  ACACTTTTAT  CACATTCTTG 3335 3340   3345 3350   3355 3360   3365 3370   3375 3380   3385 3390
     *           *           *           *           *           *
TGTACATTGT  GAGCTCTGGT  TATTTTTCTC  TTGTACCATA  GAAAAATGTA  TAAAAATTAT
ACATGTAACA  CTCGAGACCA  ATAAAAGAG   AACATGGTAT  CTTTTTACAT  ATTTTTAATA 3395 3400   3405 3410   3415 3420   3425 3430   3435 3440   3445 3450
     *           *           *           *           *           *
CAAAAAGCTA  ATGTGCAGGG  ATATTGCCTT  ATTTGTCTGT  AAAAAATGGA  GCTCAGTAAC
GTTTTTCGAT  TACACGTCCC  TATAACGGAA  TAAACAGACA  TTTTTTACCT  CGAGTCATTG 3455 3460   3465 3470   3475 3480   3485 3490   3495
     *           *           *           *           *
ATAACTGCTT  CTTGGAGCTT  TGGAATATTT  TATCCTGTAT  TCTTGTTT      (SEQ ID NO: 5)
TATTGACGAA  GAACCTCGAA  ACCTTATAAA  ATAGGACATA  AGAACAAA
```

FIG. 6F

```
              5        10        15        20        25        30        35        40        45        50
                        *                   *                   *                   *                   *
          CAACA ATG GCG GCT CCG AGC CCG AGC GGT GGC GGC GGC AGC GGC ACC CCC
          GTTGT TAC CGC CGA GGC TCG GGC TCG CCA CCG CCG CCG TCG CCG TGG GGG
                Met Ala Ala Pro Ser Pro Ser Gly Gly Gly Gly Ser Gly Thr Pro>

55        60        65        70        75        80        85        90        95
             *                   *                   *                   *
          GGC CCC GTA GGG TCC CCG GCG CCA GGC CAC CCG GCC GTC AGC AGC ATG
          CCG GGG CAT CCC AGG GGC CGC GGT CCG GTG GGC CGG CAG TCG TCG TAC
          Gly Pro Val Gly Ser Pro Ala Pro Gly His Pro Ala Val Ser Ser Met>

100       105       110       115       120       125       130       135       140       145
           *                   *                   *                   *                   *
          CAG GGT AAA CGC AAA GCA CTG AAG TTG AAT TTT GCA AAT CCA CCT TTC
          GTC CCA TTT GCG TTT CGT GAC TTC AAC TTA AAA CGT TTA GGT GGA AAG
          Gln Gly Lys Arg Lys Ala Leu Lys Leu Asn Phe Ala Asn Pro Pro Phe>

150       155       160       165       170       175       180       185       190
               *                   *                   *                   *                   *
          AAA TCT ACA GCA AGG TTT ACT CTG AAT CCC AAT CCT ACA GGA GTT CAA
          TTT AGA TGT CGT TCC AAA TGA GAC TTA GGG TTA GGA TGT CCT CAA GTT
          Lys Ser Thr Ala Arg Phe Thr Leu Asn Pro Asn Pro Thr Gly Val Gln>

195       200       205       210       215       220       225       230       235       240
                      *                   *                   *                   *                   *
          AAC CCA CAC ATA GAG AGA CTG AGA ACA CAC AGC ATT GAG TCA TCA GGA
          TTG GGT GTG TAT CTC TCT GAC TCT TGT GTG TCG TAA CTC AGT AGT CCT
          Asn Pro His Ile Glu Arg Leu Arg Thr His Ser Ile Glu Ser Ser Gly>

245       250       255       260       265       270       275       280       285       290
             *                   *                   *                   *                   *
          AAA CTG AAG ATC TCC CCT GAA CAA CAC TGG GAT TTC ACT GCA GAG GAC
          TTT GAC TTC TAG AGG GGA CTT GTT GTG ACC CTA AAG TGA CGT CTC CTG
          Lys Leu Lys Ile Ser Pro Glu Gln His Trp Asp Phe Thr Ala Glu Asp>

295       300       305       310       315       320       325       330       335
                   *                   *                   *                   *
          TTG AAA GAC CTT GGA GAA ATT GGA CGA GGA GCT TAT GGT TCT GTC AAC
          AAC TTT CTG GAA CCT CTT TAA CCT GCT CCT CGA ATA CCA AGA CAG TTG
          Leu Lys Asp Leu Gly Glu Ile Gly Arg Gly Ala Tyr Gly Ser Val Asn>

340       345       350       355       360       365       370       375       380       385
                      *                   *                   *                   *                   *
          AAA ATG GTC CAC AAA CCA AGT GGG CAA ATA ATG GCA GTT AAA AGA ATT
          TTT TAC CAG GTG TTT GGT TCA CCC GTT TAT TAC CGT CAA TTT TCT TAA
          Lys Met Val His Lys Pro Ser Gly Gln Ile Met Ala Val Lys Arg Ile>

390       395       400       405       410       415       420       425       430
             *                   *                   *                   *                   *
          CGG TCA ACA GTG GAT GAA AAA GAA CAA AAA CAA CTT CTT ATG GAT TTG
          GCC AGT TGT CAC CTA CTT TTT CTT GTT TTT GTT GAA GAA TAC CTA AAC
          Arg Ser Thr Val Asp Glu Lys Glu Gln Lys Gln Leu Leu Met Asp Leu>

435       440       445       450       455       460       465       470       475       480
                      *                   *                   *                   *                   *
          GAT GTA GTA ATG CGG AGT AGT GAT TGC CCA TAC ATT GTT CAG TTT TAT
          CTA CAT CAT TAC GCC TCA TCA CTA ACG GGT ATG TAA CAA GTC AAA ATA
          Asp Val Val Met Arg Ser Ser Asp Cys Pro Tyr Ile Val Gln Phe Tyr>
```

FIG. 7A

```
     485       490       495       500       505       510       515       520       525       530
                *                             *                   *                   *           *
     GGT GCA   CTC TTC   AGA GAG   GGT GAC   TGT TGG   ATC TGT   ATG GAA   CTC ATG
     CCA CGT   GAG AAG   TCT CTC   CCA CTG   ACA ACC   TAG ACA   TAC CTT   GAG TAC
     Gly Ala   Leu Phe   Arg Glu   Gly Asp   Cys Trp   Ile Cys   Met Glu   Leu Met>

535       540       545       550       555       560       565       570       575
                      *                   *                   *                   *
           TCT ACC   TCG TTT   GAT AAG   TTT TAC   AAA TAT   GTA TAT   AGT GTA   TTA GAT
           AGA TGG   AGC AAA   CTA TTC   AAA ATG   TTT ATA   CAT ATA   TCA CAT   AAT CTA
           Ser Thr   Ser Phe   Asp Lys   Phe Tyr   Lys Tyr   Val Tyr   Ser Val   Leu Asp>

580       585       590       595       600       605       610       615       620       625
       *                   *                   *                   *                   *
     GAT GTT   ATT CCA   GAA GAA   ATT TTA   GGC AAA   ATC ACT   TTA GCA   ACT GTG
     CTA CAA   TAA GGT   CTT CTT   TAA AAT   CCG TTT   TAG TGA   AAT CGT   TGA CAC
     Asp Val   Ile Pro   Glu Glu   Ile Leu   Gly Lys   Ile Thr   Leu Ala   Thr Val>

630       635       640       645       650       655       660       665       670
                      *                   *                   *                   *           *
           AAA GCA   CTA AAC   CAC TTA   AAA GAA   AAC TTG   AAA ATT   ATT CAC   AGA GAT
           TTT CGT   GAT TTG   GTG AAT   TTT CTT   TTG AAC   TTT TAA   TAA GTG   TCT CTA
           Lys Ala   Leu Asn   His Leu   Lys Glu   Asn Leu   Lys Ile   Ile His   Arg Asp>

675       680       685       690       695       700       705       710       715       720
       *                   *                   *                   *                             *
     ATC AAA   CCT TCC   AAT ATT   CTT CTG   GAC AGA   AGT GGA   AAT ATT   AAG CTC
     TAG TTT   GGA AGG   TTA TAA   GAA GAC   CTG TCT   TCA CCT   TTA TAA   TTC GAG
     Ile Lys   Pro Ser   Asn Ile   Leu Leu   Asp Arg   Ser Gly   Asn Ile   Lys Leu>

725       730       735       740       745       750       755       760       765       770
                      *                   *                   *                   *                   *
           TGT GAC   TTC GGC   ATC AGT   GGA CAG   CTT GTG   GAC TCT   ATT GCC   AAG ACA
           ACA CTG   AAG CCG   TAG TCA   CCT GTC   GAA CAC   CTG AGA   TAA CGG   TTC TGT
           Cys Asp   Phe Gly   Ile Ser   Gly Gln   Leu Val   Asp Ser   Ile Ala   Lys Thr>

775       780       785       790       795       800       805       810       815
                            *                   *                   *                   *
           AGA GAT   GCT GGC   TGT AGG   CCA TAC   ATG GCA   CCT GAA   AGA ATA   GAC CCA
           TCT CTA   CGA CCG   ACA TCC   GGT ATG   TAC CGT   GGA CTT   TCT TAT   CTG GGT
           Arg Asp   Ala Gly   Cys Arg   Pro Tyr   Met Ala   Pro Glu   Arg Ile   Asp Pro>

820       825       830       835       840       845       850       855       860       865
       *                   *                   *                   *                   *
     AGC GCA   TCA CGA   CAA GGA   TAT GAT   GTC CGC   TCT GAT   GTC TGG   AGT TTG
     TCG CGT   AGT GCT   GTT CCT   ATA CTA   CAG GCG   AGA CTA   CAG ACC   TCA AAC
     Ser Ala   Ser Arg   Gln Gly   Tyr Asp   Val Arg   Ser Asp   Val Trp   Ser Leu>

870       875       880       885       890       895       900       905       910
                      *                   *                   *                   *
           GGG ATC   ACA TTG   TAT GAG   TTG GCC   ACA GGC   CGA TTT   CCT TAT   CCA AAG
           CCC TAG   TGT AAC   ATA CTC   AAC CGG   TGT CCG   GCT AAA   GGA ATA   GGT TTC
           Gly Ile   Thr Leu   Tyr Glu   Leu Ala   Thr Gly   Arg Phe   Pro Tyr   Pro Lys>

915       920       925       930       935       940       945       950       955       960
       *                   *                   *                   *                             *
     TGG AAT   AGT GTA   TTT GAT   CAA CTA   ACA CAA   GTC GTG   AAA GGA   GAT CCT
     ACC TTA   TCA CAT   AAA CTA   GTT GAT   TGT GTT   CAG CAC   TTT CCT   CTA GGA
     Trp Asn   Ser Val   Phe Asp   Gln Leu   Thr Gln   Val Val   Lys Gly   Asp Pro>

```
CCG CAG CTG AGT AAT TCT GAG GAA AGG GAA TTC TCC CCG AGT TTC ATC
GGC GTC GAC TCA TTA AGA CTC CTT TCC CTT AAG AGG GGC TCA AAG TAG
Pro Gln Leu Ser Asn Ser Glu Glu Arg Glu Phe Ser Pro Ser Phe Ile>

1015   1020 1025     1030     1035 1040     1045     1050 1055
                   *                  *                  *
     AAC TTT GTC AAC TTG TGC CTT ACG AAG GAT GAA TCC AAA AGG CCA AAG
     TTG AAA CAG TTG AAC ACG GAA TGC TTC CTA CTT AGG TTT TCC GGT TTC
     Asn Phe Val Asn Leu Cys Leu Thr Lys Asp Glu Ser Lys Arg Pro Lys>

1060   1065 1070     1075     1080 1085     1090     1095 1100     1105
  *           *                 *                  *                  *
     TAT AAA GAG CTT CTG AAA CAT CCC TTT ATT TTG ATG TAT GAA GAA CGT
     ATA TTT CTC GAA GAC TTT GTA GGG AAA TAA AAC TAC ATA CTT CTT GCA
     Tyr Lys Glu Leu Leu Lys His Pro Phe Ile Leu Met Tyr Glu Glu Arg>

1110 1115     1120     1125 1130     1135     1140 1145     1150
       *             *                *                  *            *
     GCC GTT GAG GTC GCA TGC TAT GTT TGT AAA ATC CTG GAT CAA ATG CCA
     CGG CAA CTC CAG CGT ACG ATA CAA ACA TTT TAG GAC CTA GTT TAC GGT
     Ala Val Glu Val Ala Cys Tyr Val Cys Lys Ile Leu Asp Gln Met Pro>

1155   1160     1165     1170 1175     1180     1185 1190   1195 1200
    *                *                *                  *            *
     GCT ACT CCC AGC TCT CCC ATG TAT GTC GAT TGATAT CGYTGCTACA
     CGA TGA GGG TCG AGA GGG TAC ATA CAG CTA ACTATA GCRACGATGT
     Ala Thr Pro Ser Ser Pro Met Tyr Val Asp> (SEQ ID NO:8)

1205 1210  1215 1220  1225 1230  1235 1240  1245 1250  1255 1260
            *           *           *           *           *           *
     TCAGACTCTA GAAAAAAGGG CTGAGAGGAA GCAAGACGTA AAGAATTTTC ATCCCGTATC
     AGTCTGAGAT CTTTTTTCCC GACTCTCCTT CGTTCTGCAT TTCTTAAAAG TAGGGCATAG 1265 1270  1275 1280  1285 1290  1295 1300  1305 1310  1315 1320
            *           *           *           *           *           *
     ACAGTGTTTT TATTGCTCGC CCAGACACCA TGTGCAATAA GATTGGTGTT CGTTTCCATC
     TGTCACAAAA ATAACGAGCG GGTCTGTGGT ACACGTTATT CTAACCACAA GCAAAGGTAG 1325 1330  1335 1340  1345 1350  1355 1360  1365 1370  1375 1380
            *           *           *           *           *           *
     ATGTCTGTAT ACTCCTGTCA CCTAGAACGT GCATCCTTGT AATACCTGAT TGATCACACA
     TACAGACATA TGAGGACAGT GGATCTTGCA CGTAGGAACA TTATGGACTA ACTAGTGTGT 1385 1390  1395 1400  1405 1410  1415 1420  1425 1430  1435 1440
            *           *           *           *           *           *
     GTGTTAGTGC TGGTCAGAGA GACCTCATCC TGCTCTTTTG TGATGAACAT ATTCATGAAA
     CACAATCACG ACCAGTCTCT CTGGAGTAGG ACGAGAAAAC ACTACTTGTA TAAGTACTTT 1445 1450  1455 1460  1465 1470  1475 1480  1485 1490  1495 1500
            *           *           *           *           *           *
     TGTGGAAGTC AGTACGATCA AGTTGTTGAC TGTGATTAGA TCACATCTTA AATTCATTTC
     ACACCTTCAG TCATGCTAGT TCAACAACTG ACACTAATCT AGTGTAGAAT TTAAGTAAAG 1505 1510  1515 1520  1525 1530  1535 1540  1545 1550  1555 1560
            *           *           *           *           *           *
     TAGACTCAAA ACCTGGAGAT GCAGCTACTG GAATGGTGTT TTGTCAGACT TCCAAATCCT
     ATCTGAGTTT TGGACCTCTA CGTCGATGAC CTTACCACAA AACAGTCTGA AGGTTTAGGA 1565 1570  1575 1580  1585 1590  1595 1600  1605 1610  1615 1620
            *           *           *           *           *           *
     GGAAGGACAC AGTGATGAAT GTACTATATC TGAACATAGA AACTCGGGCT TGAGTGAGAA
     CCTTCCTGTG TCACTACTTA CATGATATAG ACTTGTATCT TTGAGCCCGA ACTCACTCTT
```

FIG. 7C

```
         1625 1630   1635 1640   1645 1650   1655 1660   1665 1670   1675 1680
                *            *           *           *           *           *
         GAGCTTGCAC  AGCCAACGAG  ACACATTGCC  TTCTGGAGCT  GGGAGACAAA  GGAGGAATTT
         CTCGAACGTG  TCGGTTGCTC  TGTGTAACGG  AAGACCTCGA  CCCTCTGTTT  CCTCCTTAAA 1685 1690   1695 1700   1705 1710   1715 1720   1725 1730   1735 1740
                *            *           *           *           *           *
         ACTTTCTTCA  CCAAGTGCAA  TAGATTACTG  ATGTGATATT  CTGTTGCTTT  ACAGTTACAG
         TGAAAGAAGT  GGTTCACGTT  ATCTAATGAC  TACACTATAA  GACAACGAAA  TGTCAATGTC 1745 1750   1755 1760   1765 1770   1775 1780   1785 1790   1795 1800
                *            *           *           *           *           *
         TTGATGTTTG  GGGATCGATG  TGCTCAGCCA  AATTTCCTGT  TTGAAATATC  ATGTTAAATT
         AACTACAAAC  CCCTAGCTAC  ACGAGTCGGT  TTAAAGGACA  AACTTTATAG  TACAATTTAA 1805 1810   1815 1820   1825 1830   1835 1840   1845 1850   1855 1860
                *            *           *           *           *           *
         AGAATGAATT  TATCTTTACC  AAAAACCATG  TTGCGTTCAA  AGAGGTGAAC  ATTAAAATAT
         TCTTACTTAA  ATAGAAATGG  TTTTTGGTAC  AACGCAAGTT  TCTCCACTTG  TAATTTTATA 1865 1870   1875 1880   1885 1890   1895 1900   1905 1910   1915 1920
                *            *           *           *           *           *
         AGAGACAGGA  CAGAATGTGT  TCTTTTCTCC  TCTACCAGTC  CTATTTTTCA  ATGGGAAGAC
         TCTCTGTCCT  GTCTTACACA  AGAAAAGAGG  AGATGGTCAG  GATAAAAAGT  TACCCTTCTG 1925 1930   1935 1940   1945 1950   1955 1960   1965 1970   1975 1980
                *            *           *           *           *           *
         TCAGGAGTCT  GCCACTTGTC  AAAGAAGGTG  CTGATCCTAA  GAATTTTTCA  TTCTCAGAAT
         AGTCCTCAGA  CGGTGAACAG  TTTCTTCCAC  GACTAGGATT  CTTAAAAAGT  AAGAGTCTTA 1985 1990   1995 2000   2005 2010   2015 2020   2025 2030   2035 2040
                *            *           *           *           *           *
         TCGGTGTGCT  GCCAACTTGA  TGTTCCACCT  GCCACAAACC  ACCAGGACTG  AAAGAAGAAA
         AGCCACACGA  CGGTTGAACT  ACAAGGTGGA  CGGTGTTTGG  TGGTCCTGAC  TTTCTTCTTT 2045 2050   2055 2060   2065 2070   2075 2080   2085 2090   2095 2100
                *            *           *           *           *           *
         ACAGTACAGA  AGGCAAAGTT  TACAGATGTT  TTTAATTCTA  GTATTTTATC  TGGAACAACT
         TGTCATGTCT  TCCGTTTCAA  ATGTCTACAA  AAATTAAGAT  CATAAAATAG  ACCTTGTTGA 2105 2110   2115 2120   2125 2130   2135 2140   2145 2150   2155 2160
                *            *           *           *           *           *
         TGTAGCAGCT  ATATATTTCC  CCTTGGTCCC  AAGCCTGATA  CTTTAGCCAT  CATAACTCAC
         ACATCGTCGA  TATATAAAGG  GGAACCAGGG  TTCGGACTAT  GAAATCGGTA  GTATTGAGTG 2165 2170   2175 2180   2185 2190   2195 2200   2205 2210   2215 2220
                *            *           *           *           *           *
         TAACAGGGAG  AAGTAGCTAG  TAGCAATGTG  CCTTGATTGA  TTAGATAAAG  ATTTCTAGTA
         ATTGTCCCTC  TTCATCGATC  ATCGTTACAC  GGAACTAACT  AATCTATTTC  TAAAGATCAT 2225 2230   2235 2240   2245 2250   2255 2260   2265 2270   2275 2280
                *            *           *           *           *           *
         GGCAGCAAAA  GACCAAATCT  CAGTTGTTTG  CTTCTTGCCA  TCACTGGTCC  AGGTCTTCAG
         CCGTCGTTTT  CTGGTTTAGA  GTCAACAAAC  GAAGAACGGT  AGTGACCAGG  TCCAGAAGTC 2285 2290   2295 2300   2305 2310   2315 2320   2325 2330   2335 2340
                *            *           *           *           *           *
         TTTCCGAATC  TCTTTCCCTT  CCCCTGTGGT  CTATTGTCGC  TATGTGACTT  GCGCTTAATC
         AAAGGCTTAG  AGAAAGGGAA  GGGGACACCA  GATAACAGCG  ATACACTGAA  CGCGAATTAG 2345 2350   2355 2360   2365 2370   2375 2380   2385 2390   2395 2400
```

FIG. 7D

```
                  *          *          *          *          *          *
        CAATATTTTG CCTTTTTTCT ATATCAAAAA ACCTTTACAG TTAGCAGGGA TGTTCCTTAC
        GTTATAAAAC GGAAAAAAGA TATAGTTTTT TGGAAATGTC AATCGTCCCT ACAAGGAATG 2405 2410  2415 2420  2425 2430  2435 2440  2445 2450  2455 2460
                  *          *          *          *          *          *
        CGAGGATTTT TAACCCCCAA TCTCTCATAA TCGCTAGTGT TTAAAAGGCT AAGAATAGTG
        GCTCCTAAAA ATTGGGGGTT AGAGAGTATT AGCGATCACA AATTTTCCGA TTCTTATCAC 2465 2470  2475 2480  2485 2490  2495 2500  2505 2510  2515 2520
                  *          *          *          *          *          *
        GGGCCCAACC GATGTGGTAG GTGATAAAGA GGCATCTTTT CTAGAGACAC ATTGGACCAG
        CCCGGGTTGG CTACACCATC CACTATTTCT CCGTAGAAAA GATCTCTGTG TAACCTGGTC 2525 2530  2535 2540  2545 2550  2555 2560  2565 2570  2575 2580
                  *          *          *          *          *          *
        ATGAGGATCC GAAACGGCAG CCTTTACGTT CATCACCTGC TAGAACCTCT CGTAGTCCAT
        TACTCCTAGG CTTTGCCGTC GGAAATGCAA GTAGTGGACG ATCTTGGAGA GCATCAGGTA 2585 2590  2595 2600  2605 2610  2615 2620  2625 2630  2635 2640
                  *          *          *          *          *          *
        CACCATTTCT TGGCATTGGA ATTCTACTGG AAAAAAATAC AAAAAGCAAA ACAAAACCCT
        GTGGTAAAGA ACCGTAACCT TAAGATGACC TTTTTTTATG TTTTTCGTTT TGTTTTGGGA 2645 2650  2655 2660  2665 2670  2675 2680  2685 2690  2695 2700
                  *          *          *          *          *          *
        CAGCACTGTT ACAAGAGGCC ATTTAAGTAT CTTGTGCTTC TTCACTTACC CATTAGCCAG
        GTCGTGACAA TGTTCTCCGG TAAATTCATA GAACACGAAG AAGTGAATGG GTAATCGGTC 2705 2710  2715 2720  2725 2730  2735 2740  2745 2750  2755 2760
                  *          *          *          *          *          *
        GTTCTCATTA GGTTTTGCTT GGGCCTCCCT GGCACTGAAC CTTAGGCTTT GTATGACAGT
        CAAGAGTAAT CCAAAACGAA CCCGGAGGGA CCGTGACTTG GAATCCGAAA CATACTGTCA 2765 2770  2775 2780  2785 2790  2795 2800  2805 2810  2815 2820
                  *          *          *          *          *          *
        GAAGCAGCAC TGTGAGTGGT TCAAGCACAC TGGAATATAA AACAGTCATG GCCTGAGATG
        CTTCGTCGTG ACACTCACCA AGTTCGTGTG ACCTTATATT TTGTCAGTAC CGGACTCTAC 2825 2830  2835 2840  2845 2850  2855 2860  2865 2870  2875 2880
                  *          *          *          *          *          *
        CAGGTGATGC CATTACAGAA CCAAATCGTG GCACGTATTG CTGTGTCTCC TCTCAGAGTG
        GTCCACTACG GTAATGTCTT GGTTTAGCAC CGTGCATAAC GACACAGAGG AGAGTCTCAC 2885 2890  2895 2900  2905 2910  2915 2920  2925 2930  2935 2940
                  *          *          *          *          *          *
        ACAGTCATAA ATACTGTCAA ACAATAAAGG GAGAATGGTG CTGTTTAAAG TCACATCCCT
        TGTCAGTATT TATGACAGTT TGTTATTTCC CTCTTACCAC GACAAATTTC AGTGTAGGGA 2945 2950  2955 2960  2965 2970  2975 2980  2985 2990  2995 3000
                  *          *          *          *          *          *
        GTAAATTGCA GAATTCAAAA GTGATTATCT CTTTGATCTA CTTGCCTCAT TTCCCTATCT
        CATTTAACGT CTTAAGTTTT CACTAATAGA GAAACTAGAT GAACGGAGTA AAGGGATAGA 3005 3010  3015 3020  3025 3030  3035 3040  3045 3050  3055 3060
                  *          *          *          *          *          *
        TCTCCCCCAC GGTATCCTAA ACTTTAGACT TCCCACTGTT CTGAAAGGAG ACATTGCTCT
        AGAGGGGGTG CCATAGGATT TGAAATCTGA AGGGTGACAA GACTTTCCTC TGTAACGAGA 3065 3070  3075 3080  3085 3090  3095 3100  3105 3110  3115 3120
                  *          *          *          *          *          *
        ATGTCTGCCT TCGACCACAG CAAGCCATCA TCCTCCATTG CTCCCGGGGA CTCAAGAGGA
```

FIG. 7E

```
TACAGACGGA AGCTGGTGTC GTTCGGTAGT AGGAGGTAAC GAGGGCCCCT GAGTTCTCCT 3125 3130  3135 3140  3145 3150  3155 3160  3165 3170  3175 3180
    *           *          *          *          *          *
ATCTGTTTCT CTGCTGTCAA CTTCCCATCT GGCTCAGCAT AGGGTCACTT TGCCATTATG
TAGACAAAGA GACGACAGTT GAAGGGTAGA CCGAGTCGTA TCCCAGTGAA ACGGTAATAC 3185 3190  3195 3200  3205 3210  3215 3220  3225 3230  3235 3240
    *           *          *          *          *          *
CAAATGGAGA TAAAAGCAAT TCTGGCTGTC CAGGAGCTAA TCTGACCGTT CTATTGTGTG
GTTTACCTCT ATTTTCGTTA AGACCGACAG GTCCTCGATT AGACTGGCAA GATAACACAC 3245 3250  3255 3260  3265 3270  3275 3280  3285 3290  3295 3300
    *           *          *          *          *          *
GATGACCACA TAAGAAGGCA ATTTTAGTGT ATTAATCATA GATTATTATA AACTATAAAC
CTACTGGTGT ATTCTTCCGT TAAAATCACA TAATTAGTAT CTAATAATAT TTGATATTTG 3305 3310  3315 3320  3325 3330  3335 3340  3345 3350  3355 3360
    *           *          *          *          *          *
TTAAGGGCAA GGAGTTTATT ACAATGTATC TTTATTAAAA CAAAAGGGTG TATAGTGTTC
AATTCCCGTT CCTCAAATAA TGTTACATAG AAATAATTTT GTTTTCCCAC ATATCACAAG 3365 3370  3375 3380  3385 3390  3395 3400  3405 3410  3415 3420
    *           *          *          *          *          *
ACAAACTGTG AAAATAGTGT AAGAACTGTA CATTGTGAGC TCTGGTTATT TTTCTCTTGT
TGTTTGACAC TTTTATCACA TTCTTGACAT GTAACACTCG AGACCAATAA AAAGAGAACA 3425 3430  3435 3440  3445 3450  3455 3460  3465 3470  3475 3480
    *           *          *          *          *          *
ACCATAGAAA AATGTATAAA AATTATCAAA AAGCTAATGT GCAGGGATAT TGCCTTATTT
TGGTATCTTT TTACATATTT TTAATAGTTT TTCGATTACA CGTCCCTATA ACGGAATAAA 3485 3490  3495 3500  3505 3510  3515 3520  3525 3530  3535 3540
    *           *          *          *          *          *
GTCTGTAAAA AATGGAGCTC AGTAACATAA CTGCTTCTTG GAGCTTTGGA ATATTTTATC
CAGACATTTT TTACCTCGAG TCATTGTATT GACGAAGAAC CTCGAAACCT TATAAAATAG 3545 3550
    *
CTGTATTCTT GTTT (SEQ ID NO: 7)
GACATAAGAA CAAA
```

FIG. 7F

```
         5        10        15        20        25        30        35        40        45        50
         *                   *                   *                   *                   *
    CTCCCAACA ATG GCG GCT CCG AGC CCG AGC GGC GGC GGC GGC TCC GGG GGC
    GAGGGTTGT TAC CGC CGA GGC TCG GGC TCG CCG CCG CCG CCG AGG CCC CCG
              Met Ala Ala Pro Ser Pro Ser Gly Gly Gly Gly Ser Gly Gly>

55        60        65        70        75        80        85        90        95
         *                   *                   *                   *
    GGC AGC GGC AGC GGC ACC CCC GGC CCC GTA GGG TCC CCG GCG CCA GGC
    CCG TCG CCG TCG CCG TGG GGG CCG GGG CAT CCC AGG GGC CGC GGT CCG
    Gly Ser Gly Ser Gly Thr Pro Gly Pro Val Gly Ser Pro Ala Pro Gly>

100       105       110       115       120       125       130       135       140       145
    *                   *                   *                   *                   *
    CAC CCG GCC GTC AGC AGC ATG CAG GGT AAA CGC AAA GCA CTG AAG TTG
    GTG GGC CGG CAG TCG TCG TAC GTC CCA TTT GCG TTT CGT GAC TTC AAC
    His Pro Ala Val Ser Ser Met Gln Gly Lys Arg Lys Ala Leu Lys Leu>

150       155       160       165       170       175       180       185       190       195
    *                   *                   *                   *                   *
    AAT TTT GCA AAT CCA CCT TTC AAA TCT ACA GCA AGG TTT ACT CTG AAT
    TTA AAA CGT TTA GGT GGA AAG TTT AGA TGT CGT TCC AAA TGA GAC TTA
    Asn Phe Ala Asn Pro Pro Phe Lys Ser Thr Ala Arg Phe Thr Leu Asn>

200       205       210       215       220       225       230       235       240
         *                   *                   *                   *                   *
    CCC AAT CCT ACA GGA GTT CAA AAC CCA CAC ATA GAG AGA CTG AGA ACA
    GGG TTA GGA TGT CCT CAA GTT TTG GGT GTG TAT CTC TCT GAC TCT TGT
    Pro Asn Pro Thr Gly Val Gln Asn Pro His Ile Glu Arg Leu Arg Thr>

245       250       255       260       265       270       275       280       285       290
    *                   *                   *                   *                   *
    CAC AGC ATT GAG TCA TCA GGA AAA CTG AAG ATC TCC CCT GAA CAA CAC
    GTG TCG TAA CTC AGT AGT CCT TTT GAC TTC TAG AGG GGA CTT GTT GTG
    His Ser Ile Glu Ser Ser Gly Lys Leu Lys Ile Ser Pro Glu Gln His>

295       300       305       310       315       320       325       330       335
         *                   *                   *                   *
    TGG GAT TTC ACT GCA GAG GAC TTG AAA GAC CTT GGA GAA ATT GGA CGA
    ACC CTA AAG TGA CGT CTC CTG AAC TTT CTG GAA CCT CTT TAA CCT GCT
    Trp Asp Phe Thr Ala Glu Asp Leu Lys Asp Leu Gly Glu Ile Gly Arg>

340       345       350       355       360       365       370       375       380       385
    *                   *                   *                   *                   *
    GGA GCT TAT GGT TCT GTC AAC AAA ATG GTC CAC AAA CCA AGT GGG CAA
    CCT CGA ATA CCA AGA CAG TTG TTT TAC CAG GTG TTT GGT TCA CCC GTT
    Gly Ala Tyr Gly Ser Val Asn Lys Met Val His Lys Pro Ser Gly Gln>

390       395       400       405       410       415       420       425       430       435
    *                   *                   *                   *                   *
    ATA ATG GCA GTT AAA AGA ATT CGG TCA ACA GTG GAT GAA AAA GAA CAA
    TAT TAC CGT CAA TTT TCT TAA GCC AGT TGT CAC CTA CTT TTT CTT GTT
    Ile Met Ala Val Lys Arg Ile Arg Ser Thr Val Asp Glu Lys Glu Gln>

440       445       450       455       460       465       470       475       480
         *                   *                   *                   *                   *
    AAA CAA CTT CTT ATG GAT TTG GAT GTA GTA ATG CGG AGT AGT GAT TGC
    TTT GTT GAA GAA TAC CTA AAC CTA CAT CAT TAC GCC TCA TCA CTA ACG
    Lys Gln Leu Leu Met Asp Leu Asp Val Val Met Arg Ser Ser Asp Cys>
```

FIG. 8A

```
      485       490       495       500       505       510       515       520       525       530
                 *                   *                   *                   *                   *
      CCA TAC ATT GTT CAG TTT TAT GGT GCA CTC TTC AGA GAG GGT GAC TGT
      GGT ATG TAA CAA GTC AAA ATA CCA CGT GAG AAG TCT CTC CCA CTG ACA
      Pro Tyr Ile Val Gln Phe Tyr Gly Ala Leu Phe Arg Glu Gly Asp Cys>

535       540       545       550       555       560       565       570       575
                     *                   *                   *                   *
      TGG ATC TGT ATG GAA CTC ATG TCT ACC TCG TTT GAT AAG TTT TAC AAA
      ACC TAG ACA TAC CTT GAG TAC AGA TGG AGC AAA CTA TTC AAA ATG TTT
      Trp Ile Cys Met Glu Leu Met Ser Thr Ser Phe Asp Lys Phe Tyr Lys>

580       585       590       595       600       605       610       615       620       625
 *                   *                   *                   *                   *
TAT GTA TAT AGT GTA TTA GAT GAT GTT ATT CCA GAA GAA ATT TTA GGC
ATA CAT ATA TCA CAT AAT CTA CTA CAA TAA GGT CTT CTT TAA AAT CCG
Tyr Val Tyr Ser Val Leu Asp Asp Val Ile Pro Glu Glu Ile Leu Gly>

630       635       640       645       650       655       660       665       670       675
                 *                   *                   *                   *                   *
      AAA ATC ACT TTA GCA ACT GTG AAA GCA CTA AAC CAC TTA AAA GAA AAC
      TTT TAG TGA AAT CGT TGA CAC TTT CGT GAT TTG GTG AAT TTT CTT TTG
      Lys Ile Thr Leu Ala Thr Val Lys Ala Leu Asn His Leu Lys Glu Asn>

680       685       690       695       700       705       710       715       720
                     *                   *                   *                   *
      TTG AAA ATT ATT CAC AGA GAT ATC AAA CCT TCC AAT ATT CTT CTG GAC
      AAC TTT TAA TAA GTG TCT CTA TAG TTT GGA AGG TTA TAA GAA GAC CTG
      Leu Lys Ile Ile His Arg Asp Ile Lys Pro Ser Asn Ile Leu Leu Asp>

725       730       735       740       745       750       755       760       765       770
                 *                   *                   *                   *                   *
      AGA AGT GGA AAT ATT AAG CTC TGT GAC TTC GGC ATC AGT GGA CAG CTT
      TCT TCA CCT TTA TAA TTC GAG ACA CTG AAG CCG TAG TCA CCT GTC GAA
      Arg Ser Gly Asn Ile Lys Leu Cys Asp Phe Gly Ile Ser Gly Gln Leu>

775       780       785       790       795       800       805       810       815
                     *                   *                   *                   *
      GTG GAC TCT ATT GCC AAG ACA AGA GAT GCT GGC TGT AGG CCA TAC ATG
      CAC CTG AGA TAA CGG TTC TGT TCT CTA CGA CCG ACA TCC GGT ATG TAC
      Val Asp Ser Ile Ala Lys Thr Arg Asp Ala Gly Cys Arg Pro Tyr Met>

820       825       830       835       840       845       850       855       860       865
 *                   *                   *                   *                   *
GCA CCT GAA AGA ATA GAC CCA AGC GCA TCA CGA CAA GGA TAT GAT GTC
CGT GGA CTT TCT TAT CTG GGT TCG CGT AGT GCT GTT CCT ATA CTA CAG
Ala Pro Glu Arg Ile Asp Pro Ser Ala Ser Arg Gln Gly Tyr Asp Val>

870       875       880       885       890       895       900       905       910       915
                 *                   *                   *                   *                   *
      CGC TCT GAT GTC TGG AGT TTG GGG ATC ACA TTG TAT GAG TTG GCC ACA
      GCG AGA CTA CAG ACC TCA AAC CCC TAG TGT AAC ATA CTC AAC CGG TGT
      Arg Ser Asp Val Trp Ser Leu Gly Ile Thr Leu Tyr Glu Leu Ala Thr>

920       925       930       935       940       945       950       955       960
                     *                   *                   *                   *
      GGC CGA TTT CCT TAT CCA AAG TGG AAT AGT GTA TTT GAT CAA CTA ACA
      CCG GCT AAA GGA ATA GGT TTC ACC TTA TCA CAT AAA CTA GTT GAT TGT
      Gly Arg Phe Pro Tyr Pro Lys Trp Asn Ser Val Phe Asp Gln Leu Thr>

```
CAA GTC GTG AAA GGA GAT CCT CCG CAG CTG AGT AAT TCT GAG GAA AGG
GTT CAG CAC TTT CCT CTA GGA GGC GTC GAC TCA TTA AGA CTC CTT TCC
Gln Val Val Lys Gly Asp Pro Pro Gln Leu Ser Asn Ser Glu Glu Arg>

1015  1020  1025  1030  1035  1040  1045 1050  1055
                *           *           *          *
GAA TTC TCC CCG AGT TTC ATC AAC TTT GTC AAC TTG TGC CTT ACG AAG
CTT AAG AGG GGC TCA AAG TAG TTG AAA CAG TTG AAC ACG GAA TGC TTC
Glu Phe Ser Pro Ser Phe Ile Asn Phe Val Asn Leu Cys Leu Thr Lys>

1060 1065  1070  1075  1080  1085  1090 1095  1100  1105
  *          *           *           *          *
GAT GAA TCC AAA AGG CCA AAG TAT AAA GAG CTT CTG AAA CAT CCC TTT
CTA CTT AGG TTT TCC GGT TTC ATA TTT CTC GAA GAC TTT GTA GGG AAA
Asp Glu Ser Lys Arg Pro Lys Tyr Lys Glu Leu Leu Lys His Pro Phe>

1110   1115  1120  1125  1130   1135  1140  1145   1150  1155
  *           *            *           *            *
ATT TTG ATG TAT GAA GAA CGT GCC GTT GAG GTC GCA TGC TAT GTT TGT
TAA AAC TAC ATA CTT CTT GCA CGG CAA CTC CAG CGT ACG ATA CAA ACA
Ile Leu Met Tyr Glu Glu Arg Ala Val Glu Val Ala Cys Tyr Val Cys>

1160   1165  1170   1175  1180   1185  1190  1195   1200
         *           *            *            *           *
AAA ATC CTG GAT CAA ATG CCA GCT ACT CCC AGC TCT CCC ATG TAT GTC
TTT TAG GAC CTA GTT TAC GGT CGA TGA GGG TCG AGA GGG TAC ATA CAG
Lys Ile Leu Asp Gln Met Pro Ala Thr Pro Ser Ser Pro Met Tyr Val>

1205  1210  1215 1220  1225 1230  1235 1240  1245 1250  1255 1260
   *           *           *            *           *          *
GAT TGAT ATCGCTGCTA CATCAGACTC TAGAAAAAAG GGCTGAGAGG AAGCAAGACG
CTA ACTA TAGCGACGAT GTAGTCTGAG ATCTTTTTTC CCGACTCTCC TTCGTTCTGC
Asp>   (SEQ ID NO:10)

1265 1270  1275 1280  1285 1290  1295 1300  1305 1310  1315 1320
      *           *           *           *           *          *
    TAAAGAATTT TCATCCCGTA TCACAGTGTT TTTATTGCTC GCCCAGACAC CATGTGCAAT
    ATTTCTTAAA AGTAGGGCAT AGTGTCACAA AAATAACGAG CGGGTCTGTG GTACACGTTA 1325 1330  1335 1340  1345 1350  1355 1360  1365 1370  1375 1380
      *           *           *           *           *          *
    AAGATTGGTG TTCGTTTCCA TCATGTCTGT ATACTCCTGT CACCTAGAAC GTGCATCCTT
    TTCTAACCAC AAGCAAAGGT AGTACAGACA TATGAGGACA GTGGATCTTG CACGTAGGAA 1385 1390  1395 1400  1405 1410  1415 1420  1425 1430  1435 1440
      *           *           *           *           *          *
    GTAATACCTG ATTGATCACA CAGTGTTAGT GCTGGTCAGA GAGACCTCAT CCTGCTCTTT
    CATTATGGAC TAACTAGTGT GTCACAATCA CGACCAGTCT CTCTGGAGTA GGACGAGAAA 1445 1450  1455 1460  1465 1470  1475 1480  1485 1490  1495 1500
      *           *           *           *           *          *
    TGTGATGAAC ATATTCATGA AATGTGGAAG TCAGTACGAT CAAGTTGTTG ACTGTGATTA
    ACACTACTTG TATAAGTACT TTACACCTTC AGTCATGCTA GTTCAACAAC TGACACTAAT 1505 1510  1515 1520  1525 1530  1535 1540  1545 1550  1555 1560
      *           *           *           *           *          *
    GATCACATCT TAAATTCATT TCTAGACTCA AAACCTGGAG ATGCAGCTAC TGGAATGGTG
    CTAGTGTAGA ATTTAAGTAA AGATCTGAGT TTTGGACCTC TACGTCGATG ACCTTACCAC 1565 1570  1575 1580  1585 1590  1595 1600  1605 1610  1615 1620
      *           *           *           *           *          *
    TTTTGTCAGA CTTCCAAATC CTGGAAGGAC ACAGTGATGA ATGTACTATA TCTGAACATA
```

FIG. 8C

```
AAAACAGTCT GAAGGTTTAG GACCTTCCTG TGTCACTACT TACATGATAT AGACTTGTAT 1625 1630  1635 1640  1645 1650  1655 1660  1665 1670  1675 1680
     *          *          *          *          *          *
GAAACTCGGG CTTGAGTGAG AAGAGCTTGC ACAGCCAACG AGACACATTG CCTTCTGGAG
CTTTGAGCCC GAACTCACTC TTCTCGAACG TGTCGGTTGC TCTGTGTAAC GGAAGACCTC 1685 1690  1695 1700  1705 1710  1715 1720  1725 1730  1735 1740
     *          *          *          *          *          *
CTGGGAGACA AAGGAGGAAT TTACTTTCTT CACCAAGTGC AATAGATTAC TGATGTGATA
GACCCTCTGT TTCCTCCTTA AATGAAAGAA GTGGTTCACG TTATCTAATG ACTACACTAT 1745 1750  1755 1760  1765 1770  1775 1780  1785 1790  1795 1800
     *          *          *          *          *          *
TTCTGTTGCT TTACAGTTAC AGTTGATGTT TGGGGATCGA TGTGCTCAGC CAAATTTCCT
AAGACAACGA AATGTCAATG TCAACTACAA ACCCCTAGCT ACACGAGTCG GTTTAAAGGA 1805 1810  1815 1820  1825 1830  1835 1840  1845 1850  1855 1860
     *          *          *          *          *          *
GTTTGAAATA TCATGTTAAA TTAGAATGAA TTTATCTTTA CCAAAAACCA TGTTGCGTTC
CAAACTTTAT AGTACAATTT AATCTTACTT AAATAGAAAT GGTTTTTGGT ACAACGCAAG 1865 1870  1875 1880  1885 1890  1895 1900  1905 1910  1915 1920
     *          *          *          *          *          *
AAAGAGGTGA ACATTAAAAT ATAGAGACAG GACAGAATGT GTTCTTTTCT CCTCTACCAG
TTTCTCCACT TGTAATTTTA TATCTCTGTC CTGTCTTACA CAAGAAAAGA GGAGATGGTC 1925 1930  1935 1940  1945 1950  1955 1960  1965 1970  1975 1980
     *          *          *          *          *          *
TCCTATTTTT CAATGGGAAG ACTCAGGAGT CTGCCACTTG TCAAAGAAGG TGCTGATCCT
AGGATAAAAA GTTACCCTTC TGAGTCCTCA GACGGTGAAC AGTTTCTTCC ACGACTAGGA 1985 1990  1995 2000  2005 2010  2015 2020  2025 2030  2035 2040
     *          *          *          *          *          *
AAGAATTTTT CATTCTCAGA ATTCGGTGTG CTGCCAACTT GATGTTCCAC CTGCCACAAA
TTCTTAAAAA GTAAGAGTCT TAAGCCACAC GACGGTTGAA CTACAAGGTG GACGGTGTTT 2045 2050  2055 2060  2065 2070  2075 2080  2085 2090  2095 2100
     *          *          *          *          *          *
CCACCAGGAC TGAAAGAAGA AAACAGTACA GAAGGCAAAG TTTACAGATG TTTTTAATTC
GGTGGTCCTG ACTTTCTTCT TTTGTCATGT CTTCCGTTTC AAATGTCTAC AAAAATTAAG 2105 2110  2115 2120  2125 2130  2135 2140  2145 2150  2155 2160
     *          *          *          *          *          *
TAGTATTTTA TCTGGAACAA CTTGTAGCAG CTATATATTT CCCCTTGGTC CCAAGCCTGA
ATCATAAAAT AGACCTTGTT GAACATCGTC GATATATAAA GGGGAACCAG GGTTCGGACT 2165 2170  2175 2180  2185 2190  2195 2200  2205 2210  2215 2220
     *          *          *          *          *          *
TACTTTAGCC ATCATAACTC ACTAACAGGG AGAAGTAGCT AGTAGCAATG TGCCTTGATT
ATGAAATCGG TAGTATTGAG TGATTGTCCC TCTTCATCGA TCATCGTTAC ACGGAACTAA 2225 2230  2235 2240  2245 2250  2255 2260  2265 2270  2275 2280
     *          *          *          *          *          *
GATTAGATAA AGATTTCTAG TAGGCAGCAA AAGACCAAAT CTCAGTTGTT TGCTTCTTGC
CTAATCTATT TCTAAAGATC ATCCGTCGTT TTCTGGTTTA GAGTCAACAA ACGAAGAACG 2285 2290  2295 2300  2305 2310  2315 2320  2325 2330  2335 2340
     *          *          *          *          *          *
CATCACTGGT CCAGGTCTTC AGTTTCCGAA TCTCTTTCCC TTCCCCTGTG GTCTATTGTC
GTAGTGACCA GGTCCAGAAG TCAAAGGCTT AGAGAAAGGG AAGGGGACAC CAGATAACAG
```

FIG. 8D

```
         2345 2350  2355 2360  2365 2370  2375 2380  2385 2390  2395 2400
                 *          *          *          *          *          *
         GCTATGTGAC TTGCGCTTAA TCCAATATTT TGCCTTTTTT CTATATCAAA AAACCTTTAC
         CGATACACTG AACGCGAATT AGGTTATAAA ACGGAAAAAA GATATAGTTT TTTGGAAATG 2405 2410  2415 2420  2425 2430  2435 2440  2445 2450  2455 2460
                 *          *          *          *          *          *
         AGTTAGCAGG GATGTTCCTT ACCGAGGATT TTTAACCCCC AATCTCTCAT AATCGCTAGT
         TCAATCGTCC CTACAAGGAA TGGCTCCTAA AAATTGGGGG TTAGAGAGTA TTAGCGATCA 2465 2470  2475 2480  2485 2490  2495 2500  2505 2510  2515 2520
                 *          *          *          *          *          *
         GTTTAAAAGG CTAAGAATAG TGGGGCCCAA CCGATGTGGT AGGTGATAAA GAGGCATCTT
         CAAATTTTCC GATTCTTATC ACCCCGGGTT GGCTACACCA TCCACTATTT CTCCGTAGAA 2525 2530  2535 2540  2545 2550  2555 2560  2565 2570  2575 2580
                 *          *          *          *          *          *
         TTCTAGAGAC ACATTGGACC AGATGAGGAT CCGAAACGGC AGCCTTTACG TTCATCACCT
         AAGATCTCTG TGTAACCTGG TCTACTCCTA GGCTTTGCCG TCGGAAATGC AAGTAGTGGA 2585 2590  2595 2600  2605 2610  2615 2620  2625 2630  2635 2640
                 *          *          *          *          *          *
         GCTAGAACCT CTCGTAGTCC ATCACCATTT CTTGGCATTG GAATTCTACT GGAAAAAAAT
         CGATCTTGGA GAGCATCAGG TAGTGGTAAA GAACCGTAAC CTTAAGATGA CCTTTTTTTA 2645 2650  2655 2660  2665 2670  2675 2680  2685 2690  2695 2700
                 *          *          *          *          *          *
         ACAAAAAGCA AAACAAAACC CTCAGCACTG TTACAAGAGG CCATTTAAGT ATCTTGTGCT
         TGTTTTTCGT TTTGTTTTGG GAGTCGTGAC AATGTTCTCC GGTAAATTCA TAGAACACGA 2705 2710  2715 2720  2725 2730  2735 2740  2745 2750  2755 2760
                 *          *          *          *          *          *
         TCTTCACTTA CCCATTAGCC AGGTTCTCAT TAGGTTTTGC TTGGGCCTCC CTGGCACTGA
         AGAAGTGAAT GGGTAATCGG TCCAAGAGTA ATCCAAAACG AACCCGGAGG GACCGTGACT 2765 2770  2775 2780  2785 2790  2795 2800  2805 2810  2815 2820
                 *          *          *          *          *          *
         ACCTTAGGCT TTGTATGACA GTGAAGCAGC ACTGTGAGTG GTTCAAGCAC ACTGGAATAT
         TGGAATCCGA AACATACTGT CACTTCGTCG TGACACTCAC CAAGTTCGTG TGACCTTATA 2825 2830  2835 2840  2845 2850  2855 2860  2865 2870  2875 2880
                 *          *          *          *          *          *
         AAAACAGTCA TGGCCTGAGA TGCAGGTGAT GCCATTACAG AACCAAATCG TGGCACGTAT
         TTTTGTCAGT ACCGGACTCT ACGTCCACTA CGGTAATGTC TTGGTTTAGC ACCGTGCATA 2885 2890  2895 2900  2905 2910  2915 2920  2925 2930  2935 2940
                 *          *          *          *          *          *
         TGCTGTGTCT CCTCTCAGAG TGACAGTCAT AAATACTGTC AAACAATAAA GGGAGAATGG
         ACGACACAGA GGAGAGTCTC ACTGTCAGTA TTTATGACAG TTTGTTATTT CCCTCTTACC 2945 2950  2955 2960  2965 2970  2975 2980  2985 2990  2995 3000
                 *          *          *          *          *          *
         TGCTGTTTAA AGTCACATCC CTGTAAATTG CAGAATTCAA AAGTGATTAT CTCTTTGATC
         ACGACAAATT TCAGTGTAGG GACATTTAAC GTCTTAAGTT TTCACTAATA GAGAAACTAG 3005 3010  3015 3020  3025 3030  3035 3040  3045 3050  3055 3060
                 *          *          *          *          *          *
         TACTTGCCTC ATTTCCCTAT CTTCTCCCCC ACGGTATCCT AAACTTTAGA CTTCCCACTG
         ATGAACGGAG TAAAGGGATA GAAGAGGGGG TGCCATAGGA TTTGAAATCT GAAGGGTGAC 3065 3070  3075 3080  3085 3090  3095 3100  3105 3110  3115 3120
                 *          *          *          *          *          *
```

FIG. 8E

```
TTCTGAAAGG AGACATTGCT CTATGTCTGC CTTCGACCAC AGCAAGCCAT CATCCTCCAT
AAGACTTTCC TCTGTAACGA GATACAGACG GAAGCTGGTG TCGTTCGGTA GTAGGAGGTA 3125 3130  3135 3140  3145 3150  3155 3160  3165 3170  3175 3180
         *          *          *          *          *          *
TGCTCCCGGG GACTCAAGAG GAATCTGTTT CTCTGCTGTC AACTTCCCAT CTGGCTCAGC
ACGAGGGCCC CTGAGTTCTC CTTAGACAAA GAGACGACAG TTGAAGGGTA GACCGAGTCG 3185 3190  3195 3200  3205 3210  3215 3220  3225 3230  3235 3240
         *          *          *          *          *          *
ATAGGGTCAC TTTGCCATTA TGCAAATGGA GATAAAAGCA ATTCTGGCTG TCCAGGAGCT
TATCCCAGTG AAACGGTAAT ACGTTTACCT CTATTTTCGT TAAGACCGAC AGGTCCTCGA 3245 3250  3255 3260  3265 3270  3275 3280  3285 3290  3295 3300
         *          *          *          *          *          *
AATCTGACCG TTCTATTGTG TGGATGACCA CATAAGAAGG CAATTTTAGT GTATTAATCA
TTAGACTGGC AAGATAACAC ACCTACTGGT GTATTCTTCC GTTAAAATCA CATAATTAGT 3305 3310  3315 3320  3325 3330  3335 3340  3345 3350  3355 3360
         *          *          *          *          *          *
TAGATTATTA TAAACTATAA ACTTAAGGGC AAGGAGTTTA TTACAATGTA TCTTTATTAA
ATCTAATAAT ATTTGATATT TGAATTCCCG TTCCTCAAAT AATGTTACAT AGAAATAATT 3365 3370  3375 3380  3385 3390  3395 3400  3405 3410  3415 3420
         *          *          *          *          *          *
AACAAAAGGG TGTATAGTGT TCACAAACTG TGAAAATAGT GTAAGAACTG TACATTGTGA
TTGTTTTCCC ACATATCACA AGTGTTTGAC ACTTTTATCA CATTCTTGAC ATGTAACACT 3425 3430  3435 3440  3445 3450  3455 3460  3465 3470  3475 3480
         *          *          *          *          *          *
GCTCTGGTTA TTTTTCTCTT GTACCATAGA AAAATGTATA AAAATTATCA AAAAGCTAAT
CGAGACCAAT AAAAAGAGAA CATGGTATCT TTTTACATAT TTTTAATAGT TTTTCGATTA 3485 3490  3495 3500  3505 3510  3515 3520  3525 3530  3535 3540
         *          *          *          *          *          *
GTGCAGGGAT ATTGCCTTAT TTGTCTGTAA AAAATGGAGC TCAGTAACAT AACTGCTTCT
CACGTCCCTA TAACGGAATA AACAGACATT TTTTACCTCG AGTCATTGTA TTGACGAAGA 3545 3550  3555 3560  3565 3570  3575
         *          *          *
TGGAGCTTTG GAATATTTTA TCCTGTATTC TTGTTT      (SEQ ID NO: 9)
ACCTCGAAAC CTTATAAAAT AGGACATAAG AACAAA
```

FIG. 8F

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 2030 base pairs
       (B) TYPE: nucleic acid
       (C) STRANDEDNESS: single
       (D) TOPOLOGY: linear (xi) SEQUENCE DESCRIPTION: SEQ ID NO:1:

```
TGGCTGGCAA TGGCCTTGCT GACCTCGAGC CGGGCCCACG TGGGGACCTT TGGAGCACAG      60

CCTACGATCC TGGTGCAAGG CCGGTGGATG CAGAGGCCAG TCCATATACC ACCCAGGCCT     120

GCGAGGAGCG TGGTCCCCAC CCATCCAGCC CATATGTGCA AGTGCCCTTG ACAGAGAGGC     180

TGGTCATATC CATGGTGACC ATTTATGGGC CACAACAGGT CCCCATCTGC GCAGTGAACC     240

CTGTGCTGAG CACCTTGCAG ACGTGATCTT GCTTCGTCCT GCAGCACTGT GCGGGGCAGG     300

AAAATCCAAG AGGAAGAAGG ATCTACGGAT ATCCTGCATG TCCAAGCCAC CCGCACCCAA     360

CCCCACACCC CCCCGGAACC TGGACTCCCG GACCTTCATC ACCATTGGAG ACAGAAACTT     420

TGAGGTGGAG GCTGATGACT TGGTGACCAT CTCAGAACTG GGCCGTGGAG CCTATGGGGT     480

GGTAGAGAAG GTGCGGCACG CCCAGAGCGG CACCATCATG GCCGTGAAGC GGATCCGGGC     540

CACCGTGAAC TCACAGGAGC AGAAGCGGCT GCTCATGGAC CTGGACATCA ACATGCGCAC     600

GGTCGACTGT TTCTACACTG TCACCTTCTA CGGGGCACTA TTCAGAGAGG GAGACGTGTG     660

GATCTGCATG GAGCTCATGG ACACATCCTT GGACAAGTTC TACCGGAAGG TGCTGGATAA     720

AAACATGACA ATTCCAGAGG ACATCCTTGG GGAGATTGCT GTGTCTATCG TGCGGGCCCT     780

GGAGCATCTG CACAGCAAGC TGTCGGTGAT CCACAGAGAT GTGAAGCCCT CCAATGTCCT     840

TATCAACAAG GAGGGCCATG TGAAGATGTG TGACTTTGGC ATCAGTGGCT ACTTGGTGGA     900

CTCTGTGGCC AAGACGATGG ATGCCGGCTG CAAGCCCTAC ATGGCCCCTG AGAGGATCAA     960

CCCAGAGCTG AACCAGAAGG GCTACAATGT CAAGTCCGAC GTCTGGAGCC TGGGCATCAC    1020

CATGATTGAG ATGGCCATCC TGCGGTTCCC TTACGAGTCC TGGGGGACCC CGTTCCAGCA    1080

GCTGAAGCAG GTGGTGGAGG AGCCGTCCCC CCAGCTCCCA GCCGACCGTT TCTCCCCCGA    1140
```

```
GTTTGTGGAC TTCACTGCTC AGTGCCTGAG GAAGAACCCC GCAGAGCGTA TGAGCTACCT  1200

GGAGCTGATG GAGCACCCCT TCTTCACCTT GCACAAAACC AAGAAGACGG ACATTGCTGC  1260

CTTCGTGAAG AAGATCCTGG GAGAAGACTC ATAGGGGCTG GGCCTCGGAC CCCACTCCGG  1320

CCCTCCAGAG CCCCACAGCC CCATCTGCGG GGGCAGTGCT CACCCACACC ATAAGCTACT  1380

GCCATCCTGG CCCAGGGCAT CTGGGAGGAA CCGAGGGGGC TGCTCCCACC TGGCTCTGTG  1440

GCGAGCCATT TGTCCCAAGT GCCAAAGAAG CAGACCATTG GGGCTCCCAG CCAGGCCCTT  1500

GTCGGCCCCA CCAGTGCCTC TCCCTGCTGC TCCTAGGACC CGTCTCCAGC TGCTGAGATC  1560

CTGGACTGAG GGGGCCTGGA TGCCCCCTGT GGATGCTGCT GCCCCTGCAC AGCAGGCTGC  1620

CAGTGCCTGG GTGGATGGGC CACCGCCTTG CCCAGCCTGG ATGCCATCCA AGTTGTATAT  1680

TTTTTTAATC TCTCGACTGA ATGGACTTTG CACACTTTGG CCCAGGGTGG CCACACCTCT  1740

ATCCCGGCTT TGGTGCGGGG TACACAAGAG GGGATGAGTT GTGTGAATAC CCCAAGACTC  1800

CCATGAGGGA GATGCCATGA GCCGCCCAAG GCCTTCCCCT GGCACTGGCA AACAGGGCCT  1860

CTGCGGAGCA CACTGGCTCA CCCAGTCCTG CCCGCCACCG TTATCGGTGT CATTCACCTT  1920

TCGTGTTTTT TTTAATTTAT CCTCTGTTGA TTTTTTCTTT TGCTTTATGG GTTTGGCTTG  1980

TTTTTCTTGC ATGGTTTGGA GCTGATCGCT TCTCCCCCAC CCCCTAGGGG             2030
```

(2) INFORMATION FOR SEQ ID NO:2:

(i) SEQUENCE CHARACTERISTICS:
        (A) LENGTH: 318 amino acids
        (B) TYPE: amino acid
        (C) STRANDEDNESS: Not Relevant
        (D) TOPOLOGY: linear (xi) SEQUENCE DESCRIPTION: SEQ ID NO:2:

```
Met Ser Lys Pro Pro Ala Pro Asn Pro Thr Pro Pro Arg Asn Leu Asp
  1               5                  10                  15

Ser Arg Thr Phe Ile Thr Ile Gly Asp Arg Met Phe Glu Val Glu Ala
                 20                  25                  30

Asp Asp Leu Val Thr Ile Ser Glu Leu Gly Arg Gly Ala Tyr Gly Val
             35                  40                  45

Val Glu Lys Val Arg His Ala Gln Ser Gly Thr Ile Met Ala Val Lys
 50                  55                  60

Arg Ile Arg Ala Thr Val Asn Ser Gln Glu Gln Lys Arg Leu Leu Met
 65                  70                  75                  80

Asp Leu Asp Ile Asn Met Arg Thr Val Asp Cys Phe Tyr Thr Val Thr
                 85                  90                  95

Phe Tyr Gly Ala Leu Phe Arg Glu Gly Asp Val Trp Ile Cys Met Glu
                100                 105                 110

Leu Met Asp Thr Ser Leu Asp Lys Phe Tyr Arg Lys Val Leu Asp Lys
            115                 120                 125

Asn Met Thr Ile Pro Glu Asp Ile Leu Gly Glu Ile Ala Val Ser Ile
        130                 135                 140

Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
```

```
            195                 200                 205
Pro Glu Leu Asn Gln Lys Gly Tyr Asn Val Lys Ser Asp Val Trp Ser
    210                 215                 220

Leu Gly Ile Thr Met Ile Glu Met Ala Ile Leu Arg Phe Pro Tyr Glu
225                 230                 235                 240

Ser Trp Gly Thr Pro Phe Gln Gln Leu Lys Gln Val Val Glu Pro
                245                 250                 255

Ser Pro Gln Leu Pro Ala Asp Arg Phe Ser Pro Glu Phe Val Asp Phe
            260                 265                 270

Thr Ala Gln Cys Leu Arg Lys Asn Pro Ala Glu Arg Met Ser Tyr Leu
        275                 280                 285

Glu Leu Met Glu His Pro Phe Phe Thr Leu His Lys Thr Lys Lys Thr
    290                 295                 300

Asp Ile Ala Ala Phe Val Lys Lys Ile Leu Gly Glu Asp Ser
305                 310                 315
```

(2) INFORMATION FOR SEQ ID NO:3:

(i) SEQUENCE CHARACTERISTICS:
        (A) LENGTH: 1602 base pairs
        (B) TYPE: nucleic acid
        (C) STRANDEDNESS: single
        (D) TOPOLOGY: linear (xi) SEQUENCE DESCRIPTION: SEQ ID NO:3:

```
TAGCTGCAGC ACAGCCTTCC CTAACGTTGC AACTGGGGGA AAAATCACTT TCCAGTCTGT     60

TTTGCAAGGT GTGCATTTCC ATCTTGATTC CCTGAAAGTC CATCTGCTGC ATCGGTCAAG    120

AGAAACTCCA CTTGCATGAA GATTGCACGC CTGCAGCTTG CATCTTTGTT GCAAAACTAG    180

CTACAGAAGA GAAGCAAGGC AAAGTCTTTT GTGCTCCCCT CCCCCATCAA AGGAAAGGGG    240

AAAATGTCTC AGTCGAAAGG CAAGAAGCGA AACCCTGGCC TTAAAATTCC AAAAGAAGCA    300

TTTGAACAAC CTCAGACCAG TTCCACACCA CCTAGAGATT TAGACTCCAA GGCTTGCATT    360

TCTATTGGAA ATCAGAACTT TGAGGTGAAG GCAGATGACC TGGAGCCTAT AATGGAACTG    420

GGACGAGGTG CGTACGGGGT GGTGGAGAAG ATGCGGCACG TGCCCAGCGG CAGATCATG    480

GCAGTGAAGC GGATCCGAGC CACAGTAAAT AGCCAGGAAC AGAAACGGCT ACTGATGGAT    540

TTGGATATTT CCATGAGGAC GGTGGACTGT CCATTCACTG TCACCTTTTA TGGCGCACTG    600

TTTCGGGAGG TGATGTGTG GATCTGCATG GAGCTCATGG ATACATCACT AGATAAATTC    660

TACAAACAAG TTATTGATAA AGGCCAGACA ATTCCAGAGG ACATCTTAGG GAAAATAGCA    720

GTTTCTATTG TAAAAGCATT AGAACATTTA CATAGTAAGC TGTCTGTCAT TCACAGAGAC    780

GTCAAGCCTT CTAATGTACT CATCAATGCT CTCGGTCAAG TGAAGATGTG CGATTTTGGA    840

ATCAGTGGCT ACTTGGTGGA CTCTGTTGCT AAAACAATTG ATGCAGGTTG CAAACCATAC    900

ATGGCCCCTG AAAGAATAAA CCCAGAGCTC AACCAGAAGG GATACAGTGT GAAGTCTGAC    960

ATTTGGAGTC TGGGCATCAC GATGATTGAG TTGGCCATCC TTCGATTTCC CTATGATTCA   1020

TGGGGAACTC CATTTCAGCA GCTCAAACAG GTGGTAGAGG AGCCATCGCC ACAACTCCCA   1080

GCAGACAAGT TCTCTGCAGA GTTTGTTGAC TTTACCTCAC AGTGCTTAAA GAAGAATTCC   1140

AAAGAACGGC CTACATACCC AGAGCTAATG CAACATCCAT TTTTCACCCT ACATGAATCC   1200

AAAGGAACAG ATGTGGCATC TTTTGTAAAA CTGATTCTTG GAGACTAAAA AGCAGTGGAC   1260

TTAATCGGTT GACCCTACTG TGGATTGGTG GGTTTCGGGG TGAAGCAAGT TCACTACAGC   1320

ATCAATAGAA AGTCATCTTT GAGATAATTT AACCCTGCCT CTCAGAGGGT TTTCTCTCCC   1380
```

```
AATTTTCTTT TTACTCCCCC TCTTAAGGGG GCCTTGGAAT CTATAGTATA GAATGAACTG      1440

TCTAGATGGA TGAATTATGA TAAAGGCTTA GGACTTCAAA AGGTGATTAA ATATTTAATG      1500

ATGTGTCATA TGAGTCCTCA AAAAAAAAAA AAAAAAAAAA AAAAAAAAAA AAAAAAAAAA      1560

AAAAAAAAAA AAAAAAAAAA AAAAAAAAAA AAAAAAAAAA AA                        1602
```

(2) INFORMATION FOR SEQ ID NO:4:

(i) SEQUENCE CHARACTERISTICS:
        (A) LENGTH: 334 amino acids
        (B) TYPE: amino acid
        (C) STRANDEDNESS: Not Relevant
        (D) TOPOLOGY: linear (xi) SEQUENCE DESCRIPTION: SEQ ID NO:4:

```
Met Ser Gln Ser Lys Gly Lys Lys Arg Asn Pro Gly Leu Lys Ile Pro
1               5                   10                  15

Lys Glu Ala Phe Glu Gln Pro Gln Thr Ser Ser Thr Pro Pro Arg Asp
            20                  25                  30

Leu Asp Ser Lys Ala Cys Ile Ser Ile Gly Asn Gln Asn Phe Glu Val
        35                  40                  45

Lys Ala Asp Asp Leu Glu Pro Ile Met Glu Leu Gly Arg Gly Ala Tyr
50                  55                  60

Gly Val Val Glu Lys Met Arg His Val Pro Ser Gly Gln Ile Met Ala
65                  70                  75                  80

Val Lys Arg Ile Arg Ala Thr Val Asn Ser Gln Glu Gln Lys Arg Leu
                85                  90                  95

Leu Met Asp Leu Asp Ile Ser Met Arg Thr Val Asp Cys Pro Phe Thr
            100                 105                 110

Val Thr Phe Tyr Gly Ala Leu Phe Arg Glu Gly Asp Val Trp Ile Cys
        115                 120                 125

Met Glu Leu Met Asp Thr Ser Leu Asp Lys Phe Tyr Lys Gln Val Ile
130                 135                 140

Asp Lys Gly Gln Thr Ile Pro Glu Asp Ile Leu Gly Lys Ile Ala Val
145                 150                 155                 160

Ser Ile Val Lys Ala Leu Glu His Leu His Ser Lys Leu Ser Val Ile
                165                 170                 175

His Arg Asp Val Lys Pro Ser Asn Val Leu Ile Asn Ala Leu Gly Gln
            180                 185                 190

Val Lys Met Cys Asp Phe Gly Ile Ser Gly Tyr Leu Val Asp Ser Val
        195                 200                 205

Ala Lys Thr Ile Asp Ala Gly Cys Lys Pro Tyr Met Ala Pro Glu Arg
210                 215                 220

Ile Asn Pro Glu Leu Asn Gln Lys Gly Tyr Ser Val Lys Ser Asp Ile
225                 230                 235                 240

Trp Ser Leu Gly Ile Thr Met Ile Glu Leu Ala Ile Leu Arg Phe Pro
                245                 250                 255

Tyr Asp Ser Trp Gly Thr Pro Phe Gln Gln Leu Lys Gln Val Val Glu
            260                 265                 270

Glu Pro Ser Pro Gln Leu Pro Ala Asp Lys Phe Ser Ala Glu Phe Val
        275                 280                 285

Asp Phe Thr Ser Gln Cys Leu Lys Lys Asn Ser Lys Glu Arg Pro Thr
290                 295                 300

Tyr Pro Glu Leu Met Gln His Pro Phe Phe Thr Leu His Glu Ser Lys
305                 310                 315                 320
```

Gly Thr Asp Val Ala Ser Phe Val Lys Leu Ile Leu Gly Asp
         325                 330

(2) INFORMATION FOR SEQ ID NO:5:

(i) SEQUENCE CHARACTERISTICS:
        (A) LENGTH: 3497 base pairs
        (B) TYPE: nucleic acid
        (C) STRANDEDNESS: single
        (D) TOPOLOGY: linear (xi) SEQUENCE DESCRIPTION: SEQ ID NO:5:

```
CTAGGGTCCC CGGCGCCAGG CCACCCGGCC GTCAGCAGCA TGCAGGGTAA ACGCAAAGCA      60

CTGAAGTTGA ATTTTGCAAA TCCACCTTTC AAATCTACAG CAAGGTTTAC TCTGAATCCC     120

AATCCTACAG GAGTTCAAAA CCCACACATA GAGAGACTGA GAACACACAG CATTGAGTCA     180

TCAGGAAAAC TGAAGATCTC CCCTGAACAA CACTGGGATT TCACTGCAGA GGACTTGAAA     240

GACCTTGGAG AAATTGGACG AGGAGCTTAT GGTTCTGTCA ACAAAATGGT CCACAAACCA     300

AGTGGGCAAA TAATGGCAGT TAAAAGAATT CGGTCAACAG TGGATGAAAA AGAACAAAAA     360

CAACTTCTTA TGGATTTGGA TGTAGTAATG CGGAGTAGTG ATTGCCCATA CATTGTTCAG     420

TTTTATGGTG CACTCTTCAG AGAGGGTGAC TGTTGGATCT GTATGGAACT CATGTCTACC     480

TCGTTTGATA AGTTTTACAA ATATGTATAT AGTGTATTAG ATGATGTTAT TCCAGAAGAA     540

ATTTTAGGCA AAATCACTTT AGCAACTGTG AAAGCACTAA ACCACTTAAA AGAAAACTTG     600

AAAATTATTC ACAGAGATAT CAAACCTTCC AATATTCTTC TGGACAGAAG TGGAAATATT     660

AAGCTCTGTG ACTTCGGCAT CAGTGGACAG CTTGTGGACT CTATTGCCAA GACAAGAGAT     720

GCTGGCTGTA GGCCATACAT GGCACCTGAA AGAATAGACC CAAGCGCATC ACGACAAGGA     780

TATGATGTCC GCTCTGATGT CTGGAGTTTG GGGATCACAT TGTATGAGTT GGCCACAGGC     840

CGATTTCCTT ATCCAAAGTG GAATAGTGTA TTTGATCAAC TAACACAAGT CGTGAAAGGA     900

GATCCTCCGC AGCTGAGTAA TTCTGAGGAA AGGGAATTCT CCCCGAGTTT CATCAACTTT     960

GTCAACTTGT GCCTTACGAA GGATGAATCC AAAAGGCCAA AGTATAAAGA GCTTCTGAAA    1020

CATCCCTTTA TTTTGATGTA TGAAGAACGT GCCGTTGAGG TCGCATGCTA TGTTTGTAAA    1080

ATCCTGGATC AAATGCCAGC TACTCCCAGC TCTCCCATGT ATGTCGATTG ATATCGTGCT    1140

ACATCAGACT CTAGAAAAAA GGGCTGAGAG GAAGCAAGAC GTAAAGAATT TTCATCCCGT    1200

ATCACAGTGT TTTTATTGCT CGCCCAGACA CCATGTGCAA TAAGATTGGT GTTCGTTTCC    1260

ATCATGTCTG TATACTCCTG TCACCTAGAA CGTGCATCCT TGTAATACCT GATTGATCAC    1320

ACAGTGTTAG TGCTGGTCAG AGAGACCTCA TCCTGCTCTT TTGTGATGAA CATATTCATG    1380

AAATGTGGAA GTCAGTACGA TCAAGTTGTT GACTGTGATT AGATCACATC TTAAATTCAT    1440

TTCTAGACTC AAAACCTGGA GATGCAGCTA CTGGAATGGT GTTTTGTCAG ACTTCCAAAT    1500

CCTGGAAGGA CACAGTGATG AATGTACTAT ATCTGAACAT AGAAACTCGG GCTTGAGTGA    1560

GAAGAGCTTG CACAGCCAAC GAGACACATT GCCTTCTGGA GCTGGGAGAC AAAGGAGGAA    1620

TTTACTTTCT TCACCAAGTG CAATAGATTA CTGATGTGAT ATTCTGTTGC TTTACAGTTA    1680

CAGTTGATGT TTGGGGATCG ATGTGCTCAG CCAAATTTCC TGTTTGAAAT ATCATGTTAA    1740

ATTAGAATGA ATTTATCTTT ACCAAAAACC ATGTTGCGTT CAAAGAGGTG AACATTAAAA    1800

TATAGAGACA GGACAGAATG TGTTCTTTTC TCCTCTACCA GTCCTATTTT TCAATGGGAA    1860

GACTCAGGAG TCTGCCACTT GTCAAAGAAG GTGCTGATCC TAAGAATTTT TCATTCTCAG    1920
```

```
AATTCGGTGT GCTGCCAACT TGATGTTCCA CCTGCCACAA ACCACCAGGA CTGAAAGAAG    1980

AAAACAGTAC AGAAGGCAAA GTTTACAGAT GTTTTTAATT CTAGTATTTT ATCTGGAACA    2040

ACTTGTAGCA GCTATATATT TCCCCTTGGT CCCAAGCCTG ATACTTTAGC CATCATAACT    2100

CACTAACAGG GAGAAGTAGC TAGTAGCAAT GTGCCTTGAT TGATTAGATA AAGATTTCTA    2160

GTAGGCAGCA AAAGACCAAA TCTCAGTTGT TTGCTTCTTG CCATCACTGG TCCAGGTCTT    2220

CAGTTTCCGA ATCTCTTTCC CTTCCCCTGT GGTCTATTGT CGCTATGTGA CTTGCGCTTA    2280

ATCCAATATT TTGCCTTTTT TCTATATCAA AAAACCTTTA CAGTTAGCAG GGATGTTCCT    2340

TACCGAGGAT TTTTAACCCC CAATCTCTCA TAATCGCTAG TGTTTAAAAG CTAAGAATA     2400

GTGGGGCCCA ACCGATGTGG TAGGTGATAA AGAGGCATCT TTTCTAGAGA CACATTGGAC    2460

CAGATGAGGA TCCGAAACGG CAGCCTTTAC GTTCATCACC TGCTAGAACC TCTCGTAGTC    2520

CATCACCATT TCTTGGCATT GGAATTCTAC TGGAAAAAAA TACAAAAAGC AAAACAAAAC    2580

CCTCAGCACT GTTACAAGAG GCCATTTAAG TATCTTGTGC TTCTTCACTT ACCCATTAGC    2640

CAGGTTCTCA TTAGGTTTTG CTTGGGCCTC CCTGGCACTG AACCTTAGGC TTTGTATGAC    2700

AGTGAAGCAG CACTGTGAGT GGTTCAAGCA CACTGGAATA TAAAACAGTC ATGGCCTGAG    2760

ATGCAGGTGA TGCCATTACA GAACCAAATC GTGGCACGTA TTGCTGTGTC TCCTCTCAGA    2820

GTGACAGTCA TAAATACTGT CAAACAATAA AGGGAGAATG GTGCTGTTTA AAGTCACATC    2880

CCTGTAAATT GCAGAATTCA AAAGTGATTA TCTCTTTGAT CTACTTGCCT CATTTCCCTA    2940

TCTTCTCCCC CACGGTATCC TAAACTTTAG ACTTCCCACT GTTCTGAAAG GAGACATTGC    3000

TCTATGTCTG CCTTCGACCA CAGCAAGCCA TCATCCTCCA TTGCTCCCGG GGACTCAAGA    3060

GGAATCTGTT TCTCTGCTGT CAACTTCCCA TCTGGCTCAG CATAGGGTCA CTTTGCCATT    3120

ATGCAAATGG AGATAAAAGC AATTCTGGCT GTCCAGGAGC TAATCTGACC GTTCTATTGT    3180

GTGGATGACC ACATAAGAAG GCAATTTTAG TGTATTAATC ATAGATTATT ATAAACTATA    3240

AACTTAAGGG CAAGGAGTTT ATTACAATGT ATCTTTATTA AAACAAAAGG GTGTATAGTG    3300

TTCACAAACT GTGAAAATAG TGTAAGAACT GTACATTGTG AGCTCTGGTT ATTTTTCTCT    3360

TGTACCATAG AAAAATGTAT AAAAATTATC AAAAAGCTAA TGTGCAGGGA TATTGCCTTA    3420

TTTGTCTGTA AAAAATGGAG CTCAGTAACA TAACTGCTTC TTGGAGCTTT GGAATATTTT    3480

ATCCTGTATT CTTGTTT                                                  3497
```

(2) INFORMATION FOR SEQ ID NO:6:

(i) SEQUENCE CHARACTERISTICS:
        (A) LENGTH: 363 amino acids
        (B) TYPE: amino acid
        (C) STRANDEDNESS: Not Relevant
        (D) TOPOLOGY: linear (xi) SEQUENCE DESCRIPTION: SEQ ID NO:6:

```
Met Gln Gly Lys Arg Lys Ala Leu Lys Leu Asn Phe Ala Asn Pro Pro
1               5                   10                  15

Phe Lys Ser Thr Ala Arg Phe Thr Leu Asn Pro Asn Pro Thr Gly Val
            20                  25                  30

Gln Asn Pro His Ile Glu Arg Leu Arg Thr His Ser Ile Glu Ser Ser
        35                  40                  45

Gly Lys Leu Lys Ile Ser Pro Glu Gln His Trp Asp Phe Thr Ala Glu
    50                  55                  60

Asp Leu Lys Asp Leu Gly Glu Ile Gly Arg Gly Ala Tyr Gly Ser Val
65                  70                  75                  80
```

```
Asn Lys Met Val His Lys Pro Ser Gly Gln Ile Met Ala Val Lys Arg
                85                  90                  95
Ile Arg Ser Thr Val Asp Glu Lys Glu Gln Lys Gln Leu Leu Met Asp
            100                 105                 110
Leu Asp Val Val Met Arg Ser Ser Asp Cys Pro Tyr Ile Val Gln Phe
            115                 120                 125
Tyr Gly Ala Leu Phe Arg Glu Gly Asp Cys Trp Ile Cys Met Glu Leu
            130                 135                 140
Met Ser Thr Ser Phe Asp Lys Phe Tyr Lys Tyr Val Tyr Ser Val Leu
145                 150                 155                 160
Asp Asp Val Ile Pro Glu Glu Ile Leu Gly Lys Ile Thr Leu Ala Thr
                165                 170                 175
Val Lys Ala Leu Asn His Leu Lys Glu Asn Leu Lys Ile Ile His Arg
                180                 185                 190
Asp Ile Lys Pro Ser Asn Ile Leu Leu Asp Arg Ser Gly Asn Ile Lys
            195                 200                 205
Leu Cys Asp Phe Gly Ile Ser Gly Gln Leu Val Asp Ser Ile Ala Lys
            210                 215                 220
Thr Arg Asp Ala Gly Cys Arg Pro Tyr Met Ala Pro Glu Arg Ile Asp
225                 230                 235                 240
Pro Ser Ala Ser Arg Gln Gly Tyr Asp Val Arg Ser Asp Val Trp Ser
                245                 250                 255
Leu Gly Ile Thr Leu Tyr Glu Leu Ala Thr Gly Arg Phe Pro Tyr Pro
                260                 265                 270
Lys Trp Asn Ser Val Phe Asp Gln Leu Thr Gln Val Val Lys Gly Asp
            275                 280                 285
Pro Pro Gln Leu Ser Asn Ser Glu Glu Arg Glu Phe Ser Pro Ser Phe
290                 295                 300
Ile Asn Phe Val Asn Leu Cys Leu Thr Lys Asp Glu Ser Lys Arg Pro
305                 310                 315                 320
Lys Tyr Lys Glu Leu Leu Lys His Pro Phe Ile Leu Met Tyr Glu Glu
                325                 330                 335
Arg Ala Val Glu Val Ala Cys Tyr Val Cys Lys Ile Leu Asp Gln Met
                340                 345                 350
Pro Ala Thr Pro Ser Ser Pro Met Tyr Val Asp
                355                 360

(2) INFORMATION FOR SEQ ID NO:7:

(i) SEQUENCE CHARACTERISTICS:
        (A) LENGTH: 3553 base pairs
        (B) TYPE: nucleic acid
        (C) STRANDEDNESS: single
        (D) TOPOLOGY: linear (xi) SEQUENCE DESCRIPTION: SEQ ID NO:7:

CAACAATGGC GGCTCCGAGC CCGAGCGGTG GCGGCGGCAG CGGCACCCCC GGCCCCGTAG      60

GGTCCCCGGC GCCAGGCCAC CCGGCCGTCA GCAGCATGCA GGGTAAACGC AAAGCACTGA     120

AGTTGAATTT TGCAAATCCA CCTTTCAAAT CTACAGCAAG GTTTACTCTG AATCCCAATC     180

CTACAGGAGT TCAAAACCCA CACATAGAGA GACTGAGAAC ACACAGCATT GAGTCATCAG     240

GAAAACTGAA GATCTCCCCT GAACAACACT GGGATTTCAC TGCAGAGGAC TTGAAAGACC     300

TTGGAGAAAT TGGACGAGGA GCTTATGGTT CTGTCAACAA AATGGTCCAC AAACCAAGTG     360

GGCAAATAAT GGCAGTTAAA AGAATTCGGT CAACAGTGGA TGAAAAGAA CAAAAACAAC      420
```

```
TTCTTATGGA TTTGGATGTA GTAATGCGGA GTAGTGATTG CCCATACATT GTTCAGTTTT      480

ATGGTGCACT CTTCAGAGAG GGTGACTGTT GGATCTGTAT GGAACTCATG TCTACCTCGT      540

TTGATAAGTT TTACAAATAT GTATATAGTG TATTAGATGA TGTTATTCCA GAAGAAATTT      600

TAGGCAAAAT CACTTTAGCA ACTGTGAAAG CACTAAACCA CTTAAAAGAA AACTTGAAAA      660

TTATTCACAG AGATATCAAA CCTTCCAATA TTCTTCTGGA CAGAAGTGGA AATATTAAGC      720

TCTGTGACTT CGGCATCAGT GGACAGCTTG TGGACTCTAT TGCCAAGACA AGAGATGCTG      780

GCTGTAGGCC ATACATGGCA CCTGAAAGAA TAGACCCAAG CGCATCACGA CAAGGATATG      840

ATGTCCGCTC TGATGTCTGG AGTTTGGGGA TCACATTGTA TGAGTTGGCC ACAGGCCGAT      900

TTCCTTATCC AAAGTGGAAT AGTGTATTTG ATCAACTAAC ACAAGTCGTG AAAGGAGATC      960

CTCCGCAGCT GAGTAATTCT GAGGAAAGGG AATTCTCCCC GAGTTTCATC AACTTTGTCA     1020

ACTTGTGCCT TACGAAGGAT GAATCCAAAA GGCCAAAGTA TAAAGAGCTT CTGAAACATC     1080

CCTTTATTTT GATGTATGAA GAACGTGCCG TTGAGGTCGC ATGCTATGTT TGTAAAATCC     1140

TGGATCAAAT GCCAGCTACT CCCAGCTCTC CCATGTATGT CGATTGATAT CGTGCTACAT     1200

CAGACTCTAG AAAAAAGGGC TGAGAGGAAG CAAGACGTAA AGAATTTTCA TCCCGTATCA     1260

CAGTGTTTTT ATTGCTCGCC CAGACACCAT GTGCAATAAG ATTGGTGTTC GTTTCCATCA     1320

TGTCTGTATA CTCCTGTCAC CTAGAACGTG CATCCTTGTA ATACCTGATT GATCACACAG     1380

TGTTAGTGCT GGTCAGAGAG ACCTCATCCT GCTCTTTTGT GATGAACATA TTCATGAAAT     1440

GTGGAAGTCA GTACGATCAA GTTGTTGACT GTGATTAGAT CACATCTTAA ATTCATTTCT     1500

AGACTCAAAA CCTGGAGATG CAGCTACTGG AATGGTGTTT TGTCAGACTT CCAAATCCTG     1560

GAAGGACACA GTGATGAATG TACTATATCT GAACATAGAA ACTCGGGCTT GAGTGAGAAG     1620

AGCTTGCACA GCCAACGAGA CACATTGCCT TCTGGAGCTG GGAGACAAAG GAGGAATTTA     1680

CTTTCTTCAC CAAGTGCAAT AGATTACTGA TGTGATATTC TGTTGCTTTA CAGTTACAGT     1740

TGATGTTTGG GGATCGATGT GCTCAGCCAA ATTTCCTGTT TGAAATATCA TGTTAAATTA     1800

GAATGAATTT ATCTTTACCA AAAACCATGT TGCGTTCAAA GAGGTGAACA TTAAAATATA     1860

GAGACAGGAC AGAATGTGTT CTTTTCTCCT CTACCAGTCC TATTTTTCAA TGGGAAGACT     1920

CAGGAGTCTG CCACTTGTCA AGAAGGTGC TGATCCTAAG AATTTTTCAT TCTCAGAATT      1980

CGGTGTGCTG CCAACTTGAT GTTCCACCTG CCACAAACCA CCAGGACTGA AGAAGAAAA     2040

CAGTACAGAA GGCAAAGTTT ACAGATGTTT TTAATTCTAG TATTTTATCT GGAACAACTT     2100

GTAGCAGCTA TATATTTCCC CTTGGTCCCA AGCCTGATAC TTTAGCCATC ATAACTCACT     2160

AACAGGGAGA AGTAGCTAGT AGCAATGTGC CTTGATTGAT TAGATAAAGA TTTCTAGTAG     2220

GCAGCAAAAG ACCAAATCTC AGTTGTTTGC TTCTTGCCAT CACTGGTCCA GGTCTTCAGT     2280

TTCCGAATCT CTTTCCCTTC CCCTGTGGTC TATTGTCGCT ATGTGACTTG CGCTTAATCC     2340

AATATTTTGC CTTTTTTCTA TATCAAAAAA CCTTTACAGT TAGCAGGGAT GTTCCTTACC     2400

GAGGATTTTT AACCCCCAAT CTCTCATAAT CGCTAGTGTT TAAAAGGCTA AGAATAGTGG     2460

GGCCCAACCG ATGTGGTAGG TGATAAAGAG GCATCTTTTC TAGAGACACA TTGGACCAGA     2520

TGAGGATCCG AAACGGCAGC CTTTACGTTC ATCACCTGCT AGAACCTCTC GTAGTCCATC     2580

ACCATTTCTT GGCATTGGAA TTCTACTGGA AAAAAATACA AAAAGCAAAA CAAACCCTC      2640

AGCACTGTTA CAAGAGGCCA TTTAAGTATC TTGTGCTTCT TCACTTACCC ATTAGCCAGG     2700

TTCTCATTAG GTTTTGCTTG GGCCTCCCTG GCACTGAACC TTAGGCTTTG TATGACAGTG     2760
```

```
                                                    -continued
AAGCAGCACT GTGAGTGGTT CAAGCACACT GGAATATAAA ACAGTCATGG CCTGAGATGC   2820

AGGTGATGCC ATTACAGAAC CAAATCGTGG CACGTATTGC TGTGTCTCCT CTCAGAGTGA   2880

CAGTCATAAA TACTGTCAAA CAATAAAGGG AGAATGGTGC TGTTTAAAGT CACATCCCTG   2940

TAAATTGCAG AATTCAAAAG TGATTATCTC TTTGATCTAC TTGCCTCATT TCCCTATCTT   3000

CTCCCCCACG GTATCCTAAA CTTTAGACTT CCCACTGTTC TGAAAGGAGA CATTGCTCTA   3060

TGTCTGCCTT CGACCACAGC AAGCCATCAT CCTCCATTGC TCCCGGGGAC TCAAGAGGAA   3120

TCTGTTTCTC TGCTGTCAAC TTCCCATCTG GCTCAGCATA GGGTCACTTT GCCATTATGC   3180

AAATGGAGAT AAAAGCAATT CTGGCTGTCC AGGAGCTAAT CTGACCGTTC TATTGTGTGG   3240

ATGACCACAT AAGAAGGCAA TTTTAGTGTA TTAATCATAG ATTATTATAA ACTATAAACT   3300

TAAGGGCAAG GAGTTTATTA CAATGTATCT TTATTAAAAC AAAAGGGTGT ATAGTGTTCA   3360

CAAACTGTGA AAATAGTGTA AGAACTGTAC ATTGTGAGCT CTGGTTATTT TTCTCTTGTA   3420

CCATAGAAAA ATGTATAAAA ATTATCAAAA AGCTAATGTG CAGGGATATT GCCTTATTTG   3480

TCTGTAAAAA ATGGAGCTCA GTAACATAAC TGCTTCTTGG AGCTTTGGAA TATTTTATCC   3540

TGTATTCTTG TTT                                                    3553
```

(2) INFORMATION FOR SEQ ID NO:8:

(i) SEQUENCE CHARACTERISTICS:
        (A) LENGTH: 393 amino acids
        (B) TYPE: amino acid
        (C) STRANDEDNESS: Not Relevant
        (D) TOPOLOGY: linear (xi) SEQUENCE DESCRIPTION: SEQ ID NO:8:

```
Met Ala Ala Pro Ser Pro Ser Gly Gly Gly Ser Gly Thr Pro Gly
1               5                   10                  15

Pro Val Gly Ser Pro Ala Pro Gly His Pro Ala Val Ser Ser Met Gln
            20                  25                  30

Gly Lys Arg Lys Ala Leu Lys Leu Asn Phe Ala Asn Pro Pro Phe Lys
        35                  40                  45

Ser Thr Ala Arg Phe Thr Leu Asn Pro Asn Pro Thr Gly Val Gln Asn
    50                  55                  60

Pro His Ile Glu Arg Leu Arg Thr His Ser Ile Glu Ser Ser Gly Lys
65                  70                  75                  80

Leu Lys Ile Ser Pro Glu Gln His Trp Asp Phe Thr Ala Glu Asp Leu
                85                  90                  95

Lys Asp Leu Gly Glu Ile Gly Arg Gly Ala Tyr Gly Ser Val Asn Lys
            100                 105                 110

Met Val His Lys Pro Ser Gly Gln Ile Met Ala Val Lys Arg Ile Arg
        115                 120                 125

Ser Thr Val Asp Glu Lys Glu Gln Lys Gln Leu Leu Met Asp Leu Asp
    130                 135                 140

Val Val Met Arg Ser Ser Asp Cys Pro Tyr Ile Val Gln Phe Tyr Gly
145                 150                 155                 160

Ala Leu Phe Arg Glu Gly Asp Cys Trp Ile Cys Met Glu Leu Met Ser
                165                 170                 175

Thr Ser Phe Asp Lys Phe Tyr Lys Tyr Val Tyr Ser Val Leu Asp Asp
            180                 185                 190

Val Ile Pro Glu Glu Ile Leu Gly Lys Ile Thr Leu Ala Thr Val Lys
        195                 200                 205

Ala Leu Met His Leu Lys Glu Asn Leu Lys Ile Ile His Arg Asp Ile
```

```
         210                 215                 220
Lys Pro Ser Asn Ile Leu Leu Asp Arg Ser Gly Met Ile Lys Leu Cys
225                 230                 235                 240

Asp Phe Gly Ile Ser Gly Gln Leu Val Asp Ser Ile Ala Lys Thr Arg
                245                 250                 255

Asp Ala Gly Cys Arg Pro Tyr Met Ala Pro Glu Arg Ile Asp Phe Ser
                260                 265                 270

Ala Ser Arg Gln Gly Tyr Asp Val Arg Ser Asp Val Trp Ser Leu Gly
                275                 280                 285

Ile Thr Leu Tyr Glu Leu Ala Thr Gly Arg Phe Pro Tyr Pro Lys Trp
290                 295                 300

Asn Ser Val Phe Asp Gln Leu Thr Gln Val Val Lys Gly Asp Pro Pro
305                 310                 315                 320

Gln Leu Ser Asn Ser Glu Glu Arg Glu Phe Ser Pro Ser Phe Ile Asn
                325                 330                 335

Phe Val Asn Leu Cys Leu Thr Lys Asp Glu Ser Lys Arg Pro Lys Tyr
                340                 345                 350

Lys Glu Leu Leu Lys His Pro Phe Ile Leu Met Tyr Glu Glu Arg Ala
                355                 360                 365

Val Glu Val Ala Cys Tyr Val Cys Lys Ile Leu Asp Gln Met Pro Ala
                370                 375                 380

Thr Pro Ser Ser Pro Met Tyr Val Asp
385                 390
```

(2) INFORMATION FOR SEQ ID NO:9:

(i) SEQUENCE CHARACTERISTICS:
        (A) LENGTH: 3576 base pairs
        (B) TYPE: nucleic acid
        (C) STRANDEDNESS: single
        (D) TOPOLOGY: linear (xi) SEQUENCE DESCRIPTION: SEQ ID NO:9:

```
CTCCCAACAA TGGCGGCTCC GAGCCCGAGC GGCGGCGGCG GCTCCGGGGG CGGCAGCGGC      60

AGCGGCACCC CCGGCCCCGT AGGGTCCCCG GCGCCAGGCC ACCCGGCCGT CAGCAGCATG     120

CAGGGTAAAC GCAAAGCACT GAAGTTGAAT TTTGCAAATC CACCTTTCAA ATCTACAGCA     180

AGGTTTACTC TGAATCCCAA TCCTACAGGA GTTCAAAACC CACACATAGA GAGACTGAGA     240

ACACACAGCA TTGAGTCATC AGGAAAACTG AAGATCTCCC CTGAACAACA CTGGGATTTC     300

ACTGCAGAGG ACTTGAAAGA CCTTGGAGAA ATTGGACGAG GAGCTTATGG TTCTGTCAAC     360

AAAATGGTCC ACAAACCAAG TGGGCAAATA ATGGCAGTTA AAAGAATTCG GTCAACAGTG     420

GATGAAAAAG AACAAAAACA ACTTCTTATG GATTTGGATG TAGTAATGCG AGTAGTGAT      480

TGCCCATACA TTGTTCAGTT TTATGGTGCA CTCTTCAGAG AGGGTGACTG TTGGATCTGT     540

ATGGAACTCA TGTCTACCTC GTTTGATAAG TTTTACAAAT ATGTATATAG TGTATTAGAT     600

GATGTTATTC CAGAAGAAAT TTTAGGCAAA ATCACTTTAG CAACTGTGAA AGCACTAAAC     660

CACTTAAAAG AAAACTTGAA AATTATTCAC AGAGATATCA AACCTTCCAA TATTCTTCTG     720

GACAGAAGTG GAAATATTAA GCTCTGTGAC TTCGGCATCA GTGGACAGCT TGTGGACTCT     780

ATTGCCAAGA CAAGAGATGC TGGCTGTAGG CCATACATGG CACCTGAAAG AATAGACCCA     840

AGCGCATCAC GACAAGGATA TGATGTCCGC TCTGATGTCT GGAGTTTGGG GATCACATTG     900

TATGAGTTGG CCACAGGCCG ATTTCCTTAT CCAAAGTGGA ATAGTGTATT TGATCAACTA     960

ACACAAGTCG TGAAAGGAGA TCCTCCGCAG CTGAGTAATT CTGAGGAAAG GGAATTCTCC    1020
```

```
CCGAGTTTCA TCAACTTTGT CAACTTGTGC CTTACGAAGG ATGAATCCAA AAGGCCAAAG    1080

TATAAAGAGC TTCTGAAACA TCCCTTTATT TTGATGTATG AAGAACGTGC CGTTGAGGTC    1140

GCATGCTATG TTTGTAAAAT CCTGGATCAA ATGCCAGCTA CTCCCAGCTC TCCCATGTAT    1200

GTCGATTGAT ATCGCTGCTA CATCAGACTC TAGAAAAAAG GGCTGAGAGG AAGCAAGACG    1260

TAAAGAATTT TCATCCCGTA TCACAGTGTT TTTATTGCTC GCCCAGACAC CATGTGCAAT    1320

AAGATTGGTG TTCGTTTCCA TCATGTCTGT ATACTCCTGT CACCTAGAAC GTGCATCCTT    1380

GTAATACCTG ATTGATCACA CAGTGTTAGT GCTGGTCAGA GAGACCTCAT CCTGCTCTTT    1440

TGTGATGAAC ATATTCATGA AATGTGGAAG TCAGTACGAT CAAGTTGTTG ACTGTGATTA    1500

GATCACATCT TAAATTCATT TCTAGACTCA AAACCTGGAG ATGCAGCTAC TGGAATGGTG    1560

TTTTGTCAGA CTTCCAAATC CTGGAAGGAC ACAGTGATGA ATGTACTATA TCTGAACATA    1620

GAAACTCGGG CTTGAGTGAG AAGAGCTTGC ACAGCCAACG AGACACATTG CCTTCTGGAG    1680

CTGGGAGACA AAGGAGGAAT TTACTTTCTT CACCAAGTGC AATAGATTAC TGATGTGATA    1740

TTCTGTTGCT TTACAGTTAC AGTTGATGTT TGGGGATCGA TGTGCTCAGC CAAATTTCCT    1800

GTTTGAAATA TCATGTTAAA TTAGAATGAA TTTATCTTTA CCAAAAACCA TGTTGCGTTC    1860

AAAGAGGTGA ACATTAAAAT ATAGAGACAG GACAGAATGT GTTCTTTTCT CCTCTACCAG    1920

TCCTATTTTT CAATGGGAAG ACTCAGGAGT CTGCCACTTG TCAAAGAAGG TGCTGATCCT    1980

AAGAATTTTT CATTCTCAGA ATTCGGTGTG CTGCCAACTT GATGTTCCAC CTGCCACAAA    2040

CCACCAGGAC TGAAAGAAGA AAACAGTACA GAAGGCAAAG TTTACAGATG TTTTTAATTC    2100

TAGTATTTTA TCTGGAACAA CTTGTAGCAG CTATATATTT CCCCTTGGTC CCAAGCCTGA    2160

TACTTTAGCC ATCATAACTC ACTAACAGGG AGAAGTAGCT AGTAGCAATG TGCCTTGATT    2220

GATTAGATAA AGATTTCTAG TAGGCAGCAA AAGACCAAAT CTCAGTTGTT TGCTTCTTGC    2280

CATCACTGGT CCAGGTCTTC AGTTTCCGAA TCTCTTTCCC TTCCCTGTG GTCTATTGTC     2340

GCTATGTGAC TTGCGCTTAA TCCAATATTT TGCCTTTTTT CTATATCAAA AAACCTTTAC    2400

AGTTAGCAGG GATGTTCCTT ACCGAGGATT TTTAACCCCC AATCTCTCAT AATCGCTAGT    2460

GTTTAAAAGG CTAAGAATAG TGGGGCCCAA CCGATGTGGT AGGTGATAAA GAGGCATCTT    2520

TTCTAGAGAC ACATTGGACC AGATGAGGAT CCGAAACGGC AGCCTTTACG TTCATCACCT    2580

GCTAGAACCT CTCGTAGTCC ATACCATTTT CTTGGCATTG GAATTCTACT GGAAAAAAAT    2640

ACAAAAAGCA AAACAAAACC CTCAGCACTG TTACAAGAGG CCATTTAAGT ATCTTGTGCT    2700

TCTTCACTTA CCCATTAGCC AGGTTCTCAT TAGGTTTTGC TTGGGCCTCC CTGGCACTGA    2760

ACCTTAGGCT TTGTATGACA GTGAAGCAGC ACTGTGAGTG GTTCAAGCAC ACTGGAATAT    2820

AAAACAGTCA TGGCCTGAGA TGCAGGTGAT GCCATTACAG AACCAAATCG TGGCACGTAT    2880

TGCTGTGTCT CCTCTCAGAG TGACAGTCAT AAATACTGTC AAACAATAAA GGGAGAATGG    2940

TGCTGTTTAA AGTCACATCC CTGTAAATTG CAGAATTCAA AAGTGATTAT CTCTTTGATC    3000

TACTTGCCTC ATTTCCCTAT CTTCTCCCCC ACGGTATCCT AAACTTTAGA CTTCCCACTG    3060

TTCTGAAAGG AGACATTGCT CTATGTCTGC CTTCGACCAC AGCAAGCCAT CATCCTCCAT    3120

TGCTCCCGGG GACTCAAGAG GAATCTGTTT CTCTGCTGTC AACTTCCCAT CTGGCTCAGC    3180

ATAGGGTCAC TTTGCCATTA TGCAAATGGA GATAAAAGCA ATTCTGGCTG TCCAGGAGCT    3240

AATCTGACCG TTCTATTGTG TGGATGACCA CATAAGAAGG CAATTTTAGT GTATTAATCA    3300

TAGATTATTA TAAACTATAA ACTTAAGGGC AAGGAGTTTA TTACAATGTA TCTTTATTAA    3360
```

-continued

```
AACAAAAGGG TGTATAGTGT TCACAAACTG TGAAAATAGT GTAAGAACTG TACATTGTGA   3420

GCTCTGGTTA TTTTTCTCTT GTACCATAGA AAAATGTATA AAAATTATCA AAAAGCTAAT   3480

GTGCAGGGAT ATTGCCTTAT TTGTCTGTAA AAAATGGAGC TCAGTAACAT AACTGCTTCT   3540

TGGAGCTTTG GAATATTTTA TCCTGTATTC TTGTTT                             3576
```

(2) INFORMATION FOR SEQ ID NO:10:

(i) SEQUENCE CHARACTERISTICS:
        (A) LENGTH: 399 amino acids
        (B) TYPE: amino acid
        (C) STRANDEDNESS: Not Relevant
        (D) TOPOLOGY: linear (xi) SEQUENCE DESCRIPTION: SEQ ID NO:10:

```
Met Ala Ala Pro Ser Pro Ser Gly Gly Gly Ser Gly Gly Gly Ser
1               5                   10                  15

Gly Ser Gly Thr Pro Gly Pro Val Gly Ser Pro Ala Pro Gly His Pro
            20                  25                  30

Ala Val Ser Ser Met Gln Gly Lys Arg Lys Ala Leu Lys Leu Asn Phe
        35                  40                  45

Ala Asn Pro Pro Phe Lys Ser Thr Ala Arg Phe Thr Leu Asn Pro Asn
    50                  55                  60

Pro Thr Gly Val Gln Asn Pro His Ile Glu Arg Leu Arg Thr His Ser
65                  70                  75                  80

Ile Glu Ser Ser Gly Lys Leu Lys Ile Ser Pro Glu Gln His Trp Asp
                85                  90                  95

Phe Thr Ala Glu Asp Leu Lys Asp Leu Gly Glu Ile Gly Arg Gly Ala
            100                 105                 110

Tyr Gly Ser Val Asn Lys Met Val His Lys Pro Ser Gly Gln Ile Met
        115                 120                 125

Ala Val Lys Arg Ile Arg Ser Thr Val Asp Glu Lys Glu Gln Lys Gln
    130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
            180                 185                 190

Tyr Ser Val Leu Asp Asp Val Ile Pro Glu Glu Ile Leu Gly Lys Ile
        195                 200                 205

Thr Leu Ala Thr Val Lys Ala Leu Asn His Leu Lys Glu Asn Leu Lys
    210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
            260                 265                 270

Glu Arg Ile Asp Pro Ser Ala Ser Arg Gln Gly Tyr Asp Val Arg Ser
        275                 280                 285

Asp Val Trp Ser Leu Gly Ile Thr Leu Tyr Glu Leu Ala Thr Gly Arg
    290                 295                 300

Phe Pro Tyr Pro Lys Trp Asn Ser Val Phe Asp Gln Leu Thr Gln Val
305                 310                 315                 320
```

-continued

Val Lys Gly Asp Pro Pro Gln Leu Ser Asn Ser Glu Arg Glu Phe
              325                 330                 335

Ser Pro Ser Phe Ile Asn Phe Val Asn Leu Cys Leu Thr Lys Asp Glu
              340                 345                 350

Ser Lys Arg Pro Lys Tyr Lys Glu Leu Leu Lys His Pro Phe Ile Leu
              355                 360                 365

Met Tyr Glu Glu Arg Ala Val Glu Val Ala Cys Tyr Val Cys Lys Ile
370                 375                 380

Leu Asp Gln Met Pro Ala Thr Pro Ser Pro Met Tyr Val Asp
385                 390                 395

(2) INFORMATION FOR SEQ ID NO:11:

(i) SEQUENCE CHARACTERISTICS:
        (A) LENGTH: 393 amino acids
        (B) TYPE: amino acid
        (C) STRANDEDNESS: Not Relevant
        (D) TOPOLOGY: linear (xi) SEQUENCE DESCRIPTION: SEQ ID NO:11:

Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
              20                  25                  30

Leu Gln Lys Lys Leu Glu Glu Leu Glu Leu Asp Glu Gln Gln Arg Lys
              35                  40                  45

Arg Leu Glu Ala Phe Leu Thr Gln Lys Gln Lys Val Gly Glu Leu Lys
50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
              85                  90                  95

Lys Leu Ile His Leu Glu Ile Lys Pro Ala Ile Arg Asn Gln Ile Ile
              100                 105                 110

Arg Glu Leu Gln Val Leu His Glu Cys Asn Ser Pro Tyr Ile Val Gly
              115                 120                 125

Phe Tyr Gly Ala Phe Tyr Ser Asp Gly Glu Ile Ser Ile Cys Met Glu
130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
              165                 170                 175

Leu Thr Tyr Leu Arg Glu Lys His Lys Ile Met His Arg Asp Val Lys
              180                 185                 190

Pro Ser Asn Ile Leu Val Asn Ser Arg Gly Glu Ile Lys Leu Cys Asp
              195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
              245                 250                 255

Ala Val Gly Arg Tyr Pro Ile Pro Pro Pro Asp Ala Lys Glu Leu Glu
              260                 265                 270

Leu Met Phe Gly Cys Gln Val Glu Gly Asp Ala Ala Glu Thr Pro Pro
              275                 280                 285

```
Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390
```

(2) INFORMATION FOR SEQ ID NO:12:

(i) SEQUENCE CHARACTERISTICS:
        (A) LENGTH: 400 amino acids
        (B) TYPE: amino acid
        (C) STRANDEDNESS: Not Relevant
        (D) TOPOLOGY: linear (xi) SEQUENCE DESCRIPTION: SEQ ID NO:12:

```
Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Ser Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
        130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
                180                 185                 190

Arg Asp Val Lys Pro Ser Asn Ile Leu Val Asn Ser Arg Gly Glu Ile
            195                 200                 205

Lys Leu Cys Asp Phe Gly Val Ser Gly Gln Leu Ile Asp Ser Met Ala
        210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
```

```
                     245                 250                 255
Leu Val Glu Leu Ala Val Gly Arg Tyr Pro Ile Pro Pro Asp Ala
            260                 265                 270
Lys Glu Leu Glu Ala Ile Phe Gly Arg Pro Val Val Asp Gly Glu
            275                 280                 285
Gly Glu Pro His Ser Ile Ser Pro Arg Pro Arg Pro Gly Arg Pro
            290                 295                 300
Val Ser Gly His Gly Met Asp Ser Arg Pro Ala Met Ala Ile Phe Glu
305                 310                 315                 320
Leu Leu Asp Tyr Ile Val Asn Glu Pro Pro Lys Leu Pro Asn Gly
                325                 330                 335
Val Phe Thr Pro Asp Phe Gln Glu Phe Val Asn Lys Cys Leu Ile Lys
            340                 345                 350
Asn Pro Ala Glu Arg Ala Asp Leu Lys Met Leu Thr Asn His Thr Phe
            355                 360                 365
Ile Lys Arg Ser Glu Val Glu Glu Val Asp Phe Ala Gly Trp Leu Cys
            370                 375                 380
Lys Thr Leu Arg Leu Asn Gln Pro Gly Thr Pro Thr Arg Thr Ala Val
385                 390                 395                 400

(2) INFORMATION FOR SEQ ID NO:13:

(i) SEQUENCE CHARACTERISTICS:
        (A) LENGTH: 668 amino acids
        (B) TYPE: amino acid
        (C) STRANDEDNESS: Not Relevant
        (D) TOPOLOGY: linear (xi) SEQUENCE DESCRIPTION: SEQ ID NO:13:

Met Glu Asp Lys Phe Ala Asn Leu Ser Leu His Glu Lys Thr Gly Lys
1               5                   10                  15
Ser Ser Ile Gln Leu Asn Glu Gln Thr Gly Ser Asp Asn Gly Ser Ala
            20                  25                  30
Val Lys Arg Thr Ser Ser Thr Ser Ser His Tyr Asn Asn Ile Asn Ala
            35                  40                  45
Asp Leu His Ala Arg Val Lys Ala Phe Gln Glu Gln Arg Ala Leu Lys
        50                  55                  60
Arg Ser Ala Ser Val Gly Ser Asn Gln Ser Glu Gln Asp Lys Gly Ser
65                  70                  75                  80
Ser Gln Ser Pro Lys His Ile Gln Gln Ile Val Asn Lys Pro Leu Pro
                85                  90                  95
Pro Leu Pro Val Ala Gly Ser Ser Lys Val Ser Gln Arg Met Ser Ser
            100                 105                 110
Gln Val Val Gln Ala Ser Ser Lys Ser Thr Leu Lys Asn Val Leu Asp
            115                 120                 125
Asn Gln Glu Thr Gln Asn Ile Thr Asp Val Asn Ile Asn Ile Asp Thr
        130                 135                 140
Thr Lys Ile Thr Ala Thr Thr Ile Gly Val Asn Ile Gly Leu Pro Ala
145                 150                 155                 160
Thr Asp Ile Thr Pro Ser Val Ser Asn Thr Ala Ser Ala Thr His Lys
                165                 170                 175
Ala Gln Leu Leu Asn Pro Asn Arg Arg Ala Pro Arg Arg Pro Leu Ser
            180                 185                 190
Thr Gln His Pro Thr Arg Pro Asn Val Ala Pro His Lys Ala Pro Ala
            195                 200                 205
```

```
Ile Ile Asn Thr Pro Lys Gln Ser Leu Ser Ala Arg Arg Gly Leu Lys
    210                 215                 220

Leu Pro Pro Gly Gly Met Ser Leu Lys Met Pro Thr Lys Thr Ala Gln
225                 230                 235                 240

Gln Pro Gln Gln Phe Ala Pro Ser Pro Ser Asn Lys Lys His Ile Glu
                245                 250                 255

Thr Leu Ser Asn Ser Lys Val Val Glu Gly Lys Arg Ser Asn Pro Gly
            260                 265                 270

Ser Leu Ile Asn Gly Val Gln Ser Thr Ser Thr Ser Ser Thr Glu
        275                 280                 285

Gly Pro His Asp Thr Val Gly Thr Thr Pro Arg Thr Gly Asn Ser Asn
    290                 295                 300

Asn Ser Ser Asn Ser Gly Ser Ser Gly Gly Gly Leu Phe Ala Asn
305                 310                 315                 320

Phe Ser Lys Tyr Val Asp Ile Lys Ser Gly Ser Leu Asn Phe Ala Gly
                325                 330                 335

Lys Leu Ser Leu Ser Ser Lys Gly Ile Asp Phe Ser Asn Gly Ser Ser
            340                 345                 350

Ser Arg Ile Thr Leu Asp Glu Leu Glu Phe Leu Asp Glu Leu Gly His
        355                 360                 365

Gly Asn Tyr Gly Asn Val Ser Lys Val Leu His Lys Pro Thr Asn Val
    370                 375                 380

Ile Met Ala Thr Lys Glu Val Arg Leu Glu Leu Asp Glu Ala Lys Phe
385                 390                 395                 400

Arg Gln Ile Leu Met Glu Leu Glu Val Leu His Lys Cys Asn Ser Pro
                405                 410                 415

Tyr Ile Val Asp Phe Tyr Gly Ala Phe Phe Ile Glu Gly Ala Val Tyr
            420                 425                 430

Met Cys Met Glu Tyr Met Asp Gly Gly Ser Leu Asp Lys Ile Tyr Asp
        435                 440                 445

Glu Ser Ser Glu Ile Gly Gly Ile Asp Glu Pro Gln Leu Ala Phe Ile
450                 455                 460

Ala Asn Ala Val Ile His Gly Leu Lys Glu Leu Lys Glu Gln His Asn
465                 470                 475                 480

Ile Ile His Arg Asp Val Lys Pro Thr Asn Ile Leu Cys Ser Ala Asn
                485                 490                 495

Gln Gly Thr Val Lys Leu Cys Asp Phe Gly Val Ser Gly Asn Leu Val
            500                 505                 510

Ala Ser Leu Ala Lys Thr Asn Ile Gly Cys Gln Ser Tyr Met Ala Pro
        515                 520                 525

Glu Arg Ile Lys Ser Leu Asn Pro Asp Arg Ala Thr Tyr Thr Val Gln
    530                 535                 540

Ser Asp Ile Trp Ser Leu Gly Leu Ser Ile Leu Glu Met Ala Leu Gly
545                 550                 555                 560

Arg Tyr Pro Tyr Pro Pro Glu Thr Tyr Asp Asn Ile Phe Ser Gln Leu
                565                 570                 575

Ser Ala Ile Val Asp Gly Pro Pro Arg Leu Pro Ser Asp Lys Phe
            580                 585                 590

Ser Ser Asp Ala Gln Asp Phe Val Ser Leu Cys Leu Gln Lys Ile Pro
        595                 600                 605

Glu Arg Arg Pro Thr Tyr Ala Ala Leu Thr Glu His Pro Trp Leu Val
    610                 615                 620

Lys Tyr Arg Asn Gln Asp Val His Met Ser Glu Tyr Ile Thr Glu Arg
```

```
625                 630                 635                 640
Leu Glu Arg Arg Asn Lys Ile Leu Arg Glu Arg Gly Glu Asn Gly Leu
                645                 650                 655
Ser Lys Asn Val Pro Ala Leu His Met Gly Gly Leu
            660                 665
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

TTYTAYGGNG CNTTYTTYAT HGA                          23

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

ATBCTYTCNG GNGCCATKTA                             20

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:16:

ASTYRYSASA SASASYS                               17

CYTOKINE-, STRESS-, AND ONCOPROTEIN-ACTIVATED HUMAN PROTEIN KINASE KINASES

CROSS-REFERENCE TO RELATED APPLICATION

This application is a continuation of Ser. No. 08/530,950 filed Sep. 19, 1995 now U.S. Pat. No. 5,736,381, which is a continuation-in-part of pending application Ser. No. 08/446,083, filed May 19, 1995, now U.S. Pat. No. 5,804,427 which application is incorporated herein by reference and to which application we claim priority under 35 USC §120.

STATEMENT AS TO FEDERALLY SPONSORED RESEARCH

This invention was made in part with National Cancer Institute research grant CA 58396. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, NPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein E1a (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-κB (Du et al. (1993) Cell 74:887) and c-Jun (Benbrook and Jones (1990) Oncogene 5:295).

SUMMARY OF THE INVENTION

We have identified and isolated a new group of human mitogen-activated protein kinase kinases (MKKs). The MKK isoforms described herein, MKK3 (including MKK6) and MKK4 (including MKK4-α, β and -γ) have serine, threonine, and tyrosine kinase activity, and specifically phosphorylate the human MAP kinase p38 at $Thr^{180}$ and $Tyr^{182}$. The MKK4 isoforms also phosphorylate the human MAP kinases JNK (including JNK1 and JNK2) at $Thr^{183}$ and $Tyr^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2. The invention further includes MKK6 having the amino acid sequence of SEQ ID NO:4 and having serine, threonine, and tyrosine kinase activity that specifically phosphorylates human p38 MAP kinase.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:6. MKK4 isoform MKK4-β has the amino acid sequence of SEQ ID NO:8. MKK4 isoform MKK4-γ has the amino acid sequence of SEQ ID NO:10.

As used herein, the term "mitogen-activating protein kinase kinasell or "MKK" means a protein kinase which possesses the characteristic activity of phosphorylating and activating a human mitogen-activating protein kinase. Examples of MKKs include MKK3 and MKK6, which specifically phosphorylate and activate p38 MAP kinase at $Thr^{180}$ and $Tyr^{182}$, and MKK4 isoforms which specifically phosphorylate and activate p38 MAP kinase at $Thr^{180}$ and $Tyr^{182}$, and JNK at $Thr^{183}$ and $Tyr^{185}$.

The invention includes the specific p38 MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure human MKK polypeptide is at least 75%, more preferably at least 90%, and most preferably at least 99%, by weight, human MKK polypeptide. A substantially pure human MKK can be obtained, for example, by extraction from a natural source; by expression of a recombinant nucleic acid encoding a human MKK polypeptide, or by chemically synthesizing the protein. Purity can be measured by any appropriate method, e.g., column chromatography, polyacrylamide gel electrophoresis, or HPLC analysis.

In one aspect, the invention features isolated and purified polynucleotides which encode the MKKs of the invention. In one embodiment, the polynucleotide is the nucleotide sequence of SEQ ID NO:1. In other embodiments, the polynucleotide is the nucleotide sequence of SEQ ID NO:3, SEQ ID NO:5, SEQ ID NO:7, or SEQ ID NO:9, respectively.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified (Sambrook et al. (1989) in *Molecular Cloning*, 2d ed.; Cold Spring Harbor Laboratory Press, Cold Spring Harbor, N.Y., hereby specifically incorporated by reference).

The isolated and purified polynucleotide sequences of the invention also include sequences complementary to the polynucleotide encoding MKK (antisense sequences). Antisense nucleic acids are DNA or RNA molecules that are complementary to at least a portion of a specific mRNA molecule (Weintraub (1990) Scientific American 262:40). The invention includes all antisense polynucleotides capable of inhibiting production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-Sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for a inactivating a specific mRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which consist of pooled monoclonal antibodies with different epitopic specificities, as well as distinct monoclonal antibody preparations. Monoclonal antibodies are made from antigen-containing fragments of the MKK polypeptide by methods known in the art (See, for example, Kohler et al. (1975) Nature 256:495).

The term "antibody" as used herein includes intact molecules as well as fragments thereof, such as Fa, F(ab')$_2$, and Fv, which are capable of binding the epitopic determinant. Antibodies that bind MKK polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes both JNK1 and JNK2. The term "MKK substrate" as used herein include MKK substrates, as well as MKK substrate substrates, e.g., p38, JNK, ATF2, and c-Jun.

In one embodiment, activation of the MKK signal transduction pathway is determined by measuring activation of the MKK signal transduction pathway substrates p38, JNK isoforms, ATF2, or c-jun. MKK activity is measured by the rate of substrate phosphorylation as determined by quantitation of the rate of [$^{32}$P] incorporation. The specificity of MKK substrate phosphorylation can be tested by measuring p38 and JNK activation, or by employing mutated p38 and JNK molecules that lack the sites of MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1–109, or a portion thereof). ATF2 is incubated with a test sample in which MKK activity is to be measured and [γ-$^{32}$P]ATP, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

In another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Polyadenylated [poly (A)+] mRNA is isolated from a test sample. The mRNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful to screen reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$P]-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$P]-ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects. The invention is particularly useful for screening reagents that inhibit MKK activity. Such reagents are useful for the treatment or prevention of MKk-mediated disorders, for example, inflammation and oxidative damage.

The invention further features a method of treating a MKK-mediated disorder by administering to a subject in need thereof an effective dose of a therapeutic reagent that inhibits the activity of MKK.

By the term "MKK-mediated disorder" is meant a pathological condition resulting, at least in part, from excessive activation of an MKK signal transduction pathway. The MKK signal transduction pathways are activated by several factors, including inflammation and stress. MKK-mediated disorders include, for example, ischemic heart disease, burns due to heat or radiation (UV, X-ray, γ, β, etc.), kidney failure, liver damage due to oxidative stress or alcohol, respiratory distress syndrome, septic shock, rheumatoid arthritis, autoimmune disorders, and other types of inflammatory diseases.

As used herein, the term "therapeutic reagent" means any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of MKK inhibit cell growth or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by underexpression of the MKK polypeptide. In addition, portions of DNA encoding an MKK polypeptide can be introduced into cells that underexpress an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the method of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTIONS

The drawings will first be described.

Drawings

FIG. 1 is a comparison of the amino acid sequences of MKK3 (SEQ ID NO:2), MKK4-α (SEQ ID NO:6), the human MAP kinase kinases MEK1 (SEQ ID NO:11) and MEK2 (SEQ ID NO:12), and the yeast HOG1 MAP kinase kinase PBS2 (SEQ ID NO:13). MKK3 and MKK4 sequences were compared with the PILE-UP program (version 7.2; Wisconsin Genetics Computer Group). The protein sequences are presented in single letter code [A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr]. The PBS2 sequence is truncated at both the NH2— (<) and COOH— (>) termini. Gaps introduced into the sequences to optimize the alignment are illustrated by a dash. Identical residues are indicated by a period. The sites of activating phosphorylation in MEK are indicated by asterisks.

FIG. 2 is a dendrogram showing the relation between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the *Saccharomyces cerevisiae* (sc) MAP kinase kinases PBS2, MKK1, and STE7; and the *Saccharomyces pombe* (sp) MAP kinase kinases WIS1 and BYR1 are presented.

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and JNK subgroups of MAP kinase.

FIG. 4 is a representation of the nucleic acid (SEQ ID NO:1) and amino acid sequences (SEQ ID NO:2) for MKK3.

FIG. 5 is a representation of the nucleic acid (SEQ ID NO:3) and amino acid sequences (SEQ ID NO:4) for MKK6.

FIG. 6 is a representation of the nucleic acid (SEQ ID NO:5) and amino acid sequences (SEQ ID NO:6) for MKK4α.

FIG. 7 is a representation of the nucleic acid (SEQ ID NO:7) and amino acid sequences (SEQ ID NO:8) for MKK4β.

FIG. 8 is a representation of the nucleic acid (SEQ ID NO:9) and amino acid sequences (SEQ ID NO:10) for MKK4γ.

Human Mitogen-Activated Protein Kinase Kinases

Figure 2:
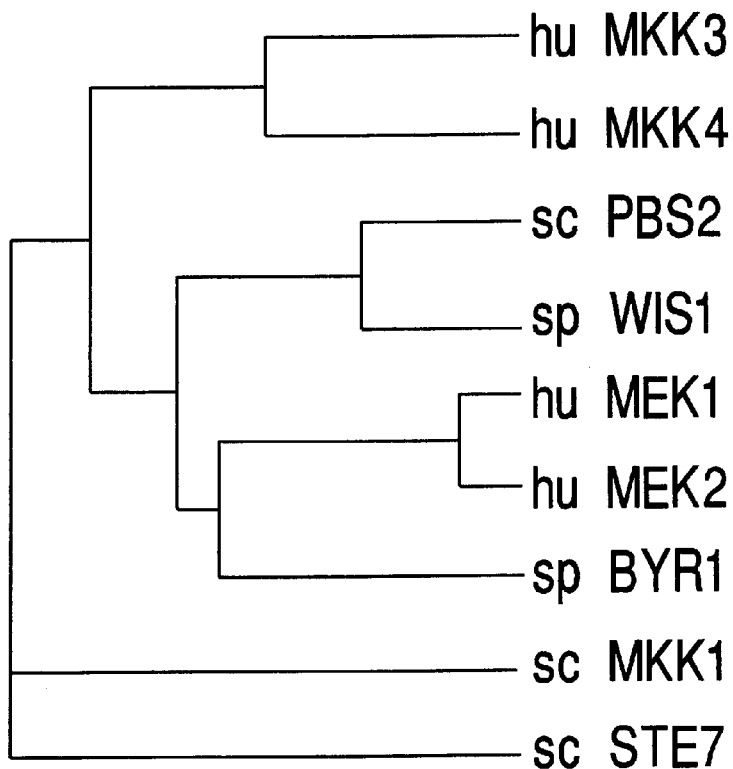

The human MAP kinase kinases MKK3 and MKK4 (MKK3/4) described herein mediate the transduction of specific signals from the cell surface to the nucleus along specific pathways. These signal transduction pathways are initiated by factors such as cytokines, UV radiation, osmotic shock, and oxidative stress. Activation of MKK3/4 results in activation of the MAP kinases p38 (MKK3/4) and JNK (MKK4). p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and Green (1993) Science 262:395), transforming growth factor-b2 (Kim et al. (1992) supra), interferon-β (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The isolation of human MKKs is described in Example 1 and in Dérijard et al. (1995) Science 267:682–685, hereby specifically incorporated by reference. Distinctive regions of the yeast PBS2 sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the $NH_2$-terminal, identified as α, β, and γ. The amino acid sequences of MKK3 (SEQ ID NO:2), MKK4-α (SEQ ID NO:6), MKK4-β (SEQ ID NO:8), and MKK4-γ (SEQ ID NO:10) are shown in FIG. 1. The nucleic acid and amino acid sequences of MKK3 (FIG. 5), MKK6 (FIG. 6), MKK4α (FIG. 7), MKK4β (FIG. 8), and MKK4γ (FIG. 9) are also provided. MKK6 was isolated from a human skeletal muscle library by cross-hybridization with MKK3. Except for differences at the N-terminus, MKK6 is highly homologous to MKK3. Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites $Thr^{180}$ and $Tyr^{182}$ with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with $[\gamma\text{-}^{32}P]ATP$, and JNK1, p38, or ERK2 was found to phosphorylate both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with $[\gamma\text{-}^{32}p]ATP$ and ATF2.

The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive $NH_2$-terminal domain deletion GST-ATF2 fusion proteins were generated, and phosphorylation by JNK1 isolated from UV-irradiated cells was examined. The results showed that JNK1 requires the presence of ATF2 residues 1–60 for phosphorylation of the $NH_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with $[\gamma^{-32}p]$ ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 9). Phosphoamino acid analysis of the full-length ATF2 molecule (residues 1–505) demonstrated that JNK phosphorylated both Thr and Ser residues. The major sites of Thr and Ser phosphorylation were located in the $NH_2$ and COOH terminal domains, respectively. The $NH_2$-terminal sites of phosphorylation were identified as $Thr^{69}$ and $Thr^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type ($Thr^{69, 71}$) and phosphorylation-defective ($Ala^{69, 71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of $Thr^{69}$ and $Thr^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at $Thr^{69}$ and/or $Thr^{71}$ of ATF2 significantly decreased the transcriptional activity of ATF2 relative to the wild-type molecule, indicating the physiological relevance of phosphorylation at these sites for activity.

The binding of JNK1 to the $NH_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating $Thr^{183}$ and $Tyr^{185}$ phosphorylation with Ala and Phe, respectively ($Ala^{183}$, $Phe^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the $NH_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on $Thr^{69}$ and $Thr^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MBP (Erickson et al. (1990) J. Biol. Chem. 265:19728), EGF-R (Northwood et al. (1991) J. Biol. Chem. 266:15266), cytoplasmic phospholipase $A_2$ ($cPLA_2$) (Lin et al. (1993) Cell 72:269), c-Myc (Alvarez et al. (1991) J. Biol. Chem. 266:15277), IκB, c-Jun, and wild-type ($Thr^{69, 71}$) or mutated ($Ala^{69, 71}$) ATF2. p38 phosphorylated MBP and EGF-R, and to a lesser extent IκB, but not the other ERK substrates, demonstrating that the substrate specificity of p38 differs from both the ERK and JNK groups of MAP kinases. Wild-type ATF2, but not mutated ATF2 ($Ala^{69, 71}$), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing Thr$^{69}$ and Thr$^{71}$ with Ala (Ala$^{69,\ 71}$). It was found that p38 did not phosphorylate mutated ATF2, which demonstrates that p38 phosphorylates ATF2 within the NH$_2$-terminal activation domain on Thr$^{69}$ and Thr$^{71}$.

A comparison of the binding of JNK and p38 to ATF2 was conducted by incubating extracts of cells expressing JNK1 or p38 with epitope alone (GST) or GST-ATF2 (residues 1–109 containing the activation domain) (Example 16). Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-1, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type (Thr$^{180}$, Tyr$^{182}$) or mutant p38 (Ala$^{180}$, Phe$^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoaminoacid analysis of p38 isolated from [$\gamma$-$^{32}$P]phosphate-labeled cells. This analysis also demonstrated that UV radiation caused increased Thr phosphorylation of p38. Significantly, the increased phosphorylation on Thr$^{180}$ and Tyr$^{182}$ was blocked by the Ala$^{180}$/Phe$^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to. inhibit p38 activity. The inhibitory effect of MKP1 was greater than PAC1. In contrast, cells transfected with a catalytically inactive mutant phosphatase (mutant PAC1 CyS$^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type (Thr$^{183}$, Tyr$^{185}$) or mutated (Ala$^{183}$, Phe$^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

Figure 3:
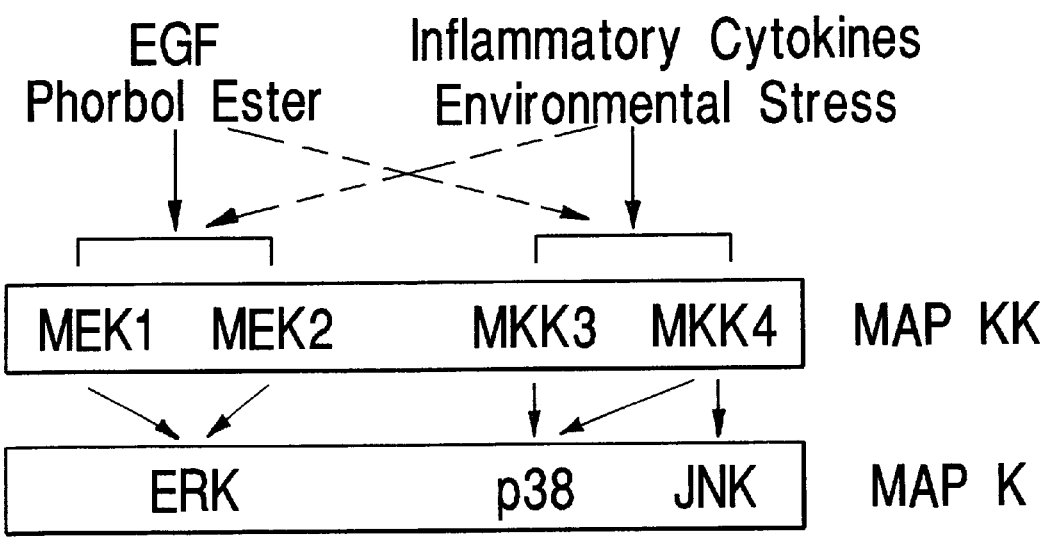

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3 and MKK4) are distinct.

MKK isoforms are useful for screening reagents which modulate MKK activity. Described in the Use section following the examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

The following examples are meant to illustrate, not limit, the invention.

EXAMPLE 1

MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:14) and ATBCTYTCNGGNGCCATKTA (SEQ ID NO:15) were designed based on the sequence of PBS2 (Brewster et al. (1993) Science 259:1760; Maeda et al. (1994) Nature 369:242). The primers were used in a PCR reaction with human brain mRNA as template. Two sequences that encoded fragments of PBS2-related protein kinases were identified. Full-length human cDNA clones were isolated by screening of a human fetal brain library (Dérijard et al. (1994) supra). The cDNA clones were examined by sequencing with an Applied iosystems model 373A machine. The largest clones obtained for MKK3 (2030 base pairs (bp)) and MKK4 (3576 bp) contained the entire coding region of these protein kinases.

The primary structures of MKK3 (SEQ ID NO:2) and MKK4α (SEQ ID NO:6) are shown in FIG. 1. An in-frame termination codon is located in the 5' untranslated region of the MKK3 cDNA, but not in the 5' region of the MKK4 cDNA. The MKK4 protein sequence presented starts at the second in-frame initiation codon.

These sequences were compared to those of the human MAP kinase kinases MEK1 (SEQ ID NO:11) and MEK2 (SEQ ID NO:12) (Zheng and Guan (1993) J. Biol. Chem 268:11435) and of the yeast MAP kinase kinase PBS2 (SEQ ID NO:13) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4α, 52%/73%; and PBS2, 40%/59%). The identity and similarity of the kinases with human MKK4α were calculated to be as follows (percent of identity to percent of similarity): MEK1, 44%/63%; MEK2, 45%/61%; MKK3, 52%/73%; and PBS2, 44%/58%.

The cDNA sequences of MKK3 and MKK4γ have been deposited in GenBank with accession numbers L36719 and L36870, respectively. The MKK4γ cDNA sequence contains both the cDNA sequences of MKK4α and MKK4β, which are generated in vivo from alternate splicing sites. One of ordinary skill in the art can readily determine the amino acid sequences of MKK3 and MKK4 isoforms from the deposited cDNA sequences.

EXAMPLE 2
Expression of MKK3 and MKK4 mRNA in Adult Human Tissue

Northern blot analysis was performed with polyadenylated [poly(A)$^+$] mRNA (2 μg) isolated from human heart, brain, placenta, lung, liver, muscle, kidney, and pancreas tissues. The mRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

The relation between members of the human and yeast MAP kinase kinase group is presented as a dendrogram (FIG. 2). MKK3/4 form a unique subgroup of human MAP kinase kinases.

EXAMPLE 3
In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) suDra). The plasmid pCMV-Flag-p38 MAP kinase was prepared with the expression vector pCMV5 (Andersson et al. (1989) J. Biol. Chem. 264:8222) and the p38 MAP kinase cDNA. The expression vectors for MKK3 and MKK4 were prepared by subcloning of the cDNAs into the polylinker of pcDNA3 (Invitrogen). The Flag epitope (Asp-Tyr-Lys-Asp-Asp-Asp-Lys (SEQ ID NO:16); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM β-glycerophosphate, 25 mM $MgCl_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 μg of substrate proteins and 50 μM [γ-$^{32}$P]ATP (10 Ci/mmol) in a final volume of 25 μl. The reactions were terminated after 30 minutes at 25° C. by addition of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace $Thr^{180}$ and $Tyr^{182}$ of p38, with Ala and Phe, respectively. The sequence of all plasmids was confirmed by automated sequencing on an Applied Biosystems model 373A machine. GST-MKK3 was incubated with [γ-$^{32}$P]ATP and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

EXAMPLE 4
In Vitro Phosphorylation and Activation of JNK and p38 MAP Kinase by MKK4

Protein kinase assays were conducted as described in Example 3. Recombinant GST-MKK4 was incubated with [γ-$^{32}$P]ATP and buffer, GST-JNK1, GST-p38 MAP kinase, or GST-ERK2. JNK1 and p38 were phosphorylated, as was MKK4 incubated with JNK1 and p38.

GST-MKK4 was incubated with [γ-$^{32}$P]ATP and buffer, wild-type JNK1 ($Thr^{183}$ $Tyr^{185}$), or mutated GST-JNK1 ($Ala^{183}$, $Phe^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

EXAMPLE 5
Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%) (Gibco-BRL). The cells were transfected with the lipofectamine reagent according to the manufacturer's recommendations (Gibco-BRL) and treated with UV radiation or EGF as described (Dérijard et al. (1994) supra).

The cells were exposed in the absence and presence of UV-C (40 J/m$^2$). The cells were solubilized with lysis buffer (20 mM tris, pH 7.4, 1% Triton X-100, 10% glycerol, 137 mM NaCl, 2 mM EDTA, 25 mM β-glycerophosphate, 1 mM Na orthovanadate, 1 mM phenylmethylsulfonyl fluoride, and leupeptin (10 μg/ml)) and centrifuged at 100,000×g for 15 minutes at 4° C. MKK3 was isolated by immunoprecipitation. The epitope-tagged protein kinases were incubated for 1 hour at 4° C. with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

EXAMPLE 6
Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4α. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunecomplex with [γ-$^{32}$P]ATP and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and UV-irradiated groups. MKK3 and MKK4 phosphorylation of ATF2 was similar to that seen with p38 MAP kinase isolated from UV-irradiated cells.

EXAMPLE 7
Phosphorylation of ATF2 by JNK1 and JNK2

COS-1 cells were maintained in Dulbecco's modified Eagle's medium supplemented with bovine serum albumin (5%) (Gibco-BRL). Metabolic labeling with $^{32}$P was performed by incubation of cells for 3 hours in phosphate-free modified Eagle's medium (Flow Laboratories Inc.) supplemented with [$^{32}$P]orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-BRL). After 48 hours of incubation, some cultures were exposed to 40 J/m$^2$ UV radiation and incubated for 1 hour at 37° C.

Cells were lysed in 20 mM Tris, pH 7.5, 25 mM β-glycerophosphate, 10% glycerol, 1% Triton X-100, 0.5% (w/v) deoxycholate, 0.1% (w/v) SDS, 0.137 M NaCl, 2 mM pyrophosphate, 1 mM orthovanadate, 2 mM EDTA, 10 μg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues 1–505) in the gel, and incubation with [γ-$^{32}$P]ATP (Dérijard et al. (1994) supra). The incorporation of [$^{32}$P]phosphate was visualized by autoradiography and quantitated with a Phosphorimager and ImageQuant soft-ware (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

EXAMPLE 8
Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine. The GST-ATF2 proteins were purified as described (Smith and Johnson (1988) Gene 67:31), resolved by SDS-PAGE and stained with Coomassie blue. GST-ATF2 fusion proteins contained residues 1–505, 1–349, 350–505, 1–109, 20–109, 40–109, and 60–109.

The phosphorylation of GST-ATF2 fusion proteins by JNK1 isolated from UV-irradiated cells was examined in an immunocomplex kinase assay. Immunecomplex kinase assays were performed with Flag epitope-tagged JNK1 and the monoclonal antibody M2 (IBI-Kodak) as described by Dérijard et al. (1994) supra). Immunecomplex protein kinase assays were also performed with a rabbit antiserum prepared with recombinant JNK1 as an antigen. The cells were solubilized with 20 mM Tris, pH 7.5, 10% glycerol, 1% Triton X-100, 0.137 M NaCl, 25 mM β-glycerophosphate, 2 mM EDTA, 1 mM orthovanadate, 2 mM pyrophosphate, 10 μg/ml leupeptin, and 1 mM PMSF. JNK1 was immunoprecipitated with protein G-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM MgCl$_2$, 25 mM β-glycerophosphate, 100 μM Na orthovanadate, 2 mM dithiothreitol). The kinase assays were performed at 25° C. for 10 minutes with 1 μg of substrate, 20 μM adenosine triphosphate and 10 μCi of [γ-$^{32}$P]ATP in 30 μl of kinase buffer. The reactions were terminated with Laemmli sample buffer and the products were resolved by SDS-PAGE (10% gel). JNK1 phosphorylates GST-ATF2 fusion proteins containing residues 1–505, 1–349, 1–109, 20–109, and 40–109, but not 60–109. These results indicate that the presence of ATF2 residues 1–60 are required for phosphorylation by JNK.

The binding of immobilized GST-ATF2 fusion proteins was examined in a solid-phase kinase assay as described by Hibi et al. (1993) Genes Dev. 7:2135, herein specifically incorporated by reference. JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of [γ-$^{32}$P]ATP. JNK1 bound GST-ATF2 fusion proteins containing residues 1–505, 1–349, 1–109, 20–109, and 40–109, indicating that the presence of residues 20–60 were required for binding of JNK1 to ATF2.

EXAMPLE 9
Phosyhorylation of the NH$_2$-terminal Activation Domain of ATF2 on Thr$^{69}$ and Thr$^{71}$ by JNK1

The effect of UV radiation on the properties of wild-type (Thr$^{69, 71}$) and phosphorylation-defective (Ala$^{69, 71}$) ATF2 molecules was examined. Mock-transfected and JNK1-transfected COS cells were treated without and with 40 J/m$^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an NH$_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem. 266:15277). The horizontal dimension of the peptide maps was electrophoresis and the vertical dimension was chromatography. The NH$_2$-terminal sites of phosphorylation were identified as Thr$^{69}$ and Thr$^{71}$ by phosphopeptide mapping and mutational analysis. Site-directed mutagenesis was performed as described above, replacing Thr$^{69}$ and Thr$^{71}$ with Ala. Phosphorylation of mutated ATF2 was not observed.

EXAMPLE 10
Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 J/m$^2$), IL-1α (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

EXAMPLE 11
Increased ATF2 Phosphorylation After Activation of JNK

COS-1 cells were transfected without (control) and with an ATF2 expression vector (ATF2), as described above (Hai et al. (1989) supra). The effect of exposure of the cells to 40 J/m$^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type (Thr$^{69, 71}$) ATF2 and mutated (Ala$^{69, 71}$) ATF2 was examined in cells labeled with [$^{32}$]P, treated without and with 40 J/m$^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phosphoamino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1 cells. A map was also prepared with a sample composed of equal amounts of in vivo and in vitro phosphorylated ATF2 (Mix). Mutation of ATF2 at Thr$^{69}$ and Thr$^{71}$ resulted in the loss of two tryptic phosphopeptides in maps of ATF2 isolated from UV-irradiated cells. These phosphopeptides correspond to mono- and bis-phosphorylated peptides containing Thr$^{69}$ and Thr$^{71}$. Both of these phosphopeptides were found in maps of ATF2 phosphorylated by JNK1 in vitro.

EXAMPLE 12
Inhibition of ATF2-Stimulated Gene Expression by Mutation of the Phosphorylation Sites Thr$^{69}$ and Thr$^{71}$ A fusion protein consisting of ATF2 and the GAL4 DNA binding domain was expressed in CHO cells as described above. The activity of the GAL4-ATF2 fusion protein was measured in co-transfection assays with the reporter plasmid pG5E1bLuc (Seth et al. (1992) J. Biol. Chem. 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results,shown in Table 1, demonstrate the importance of phosphorylation at Thr$^{69}$ and Thr$^{71}$ for transcriptional activity.

TABLE 1

INHIBITION OF ATF-2 STIMULATED GENE EXPRESSION BY MUTATION OF THE PHOSPHORYLATION SITES THR$^{69, 71}$

| PROTEIN | | LUCIFERASE ACTIVITY (Light Units/OD) |
|---|---|---|
| GAL4 | | 45 |
| GAL4-ATF2 | (wild type) | 320,000 |
| GAL4-ATF2 | (Ala$^{69}$) | 24,000 |
| GAL4-ATF2 | (Ala$^{71}$) | 22,000 |
| GAL4-ATF2 | (Ala$^{69,71}$) | 29,000 |
| GAL4-ATF2 | (Glu$^{69}$) | 27,000 |

EXAMPLE 13
Effect of Dominant-Negative JNK1 Mutant on ATF2 Function

The luciferase reporter plasmid system was used to determine the effect of point mutations at the ATF2 phosphorylation sites Thr$^{69}$ and Thr$^7$ in serum-treated CHO cells transfected with wild-type (Thr$^{183}$ Tyr$^{185}$) or mutant (Ala$^{183}$, Phe$^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

EXAMPLE 14
Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1–505), as described above. Cells were transfected with wild-type (Thr[69, 71]) or mutated (Ala[69, 71]) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on Thr[69] and Thr[71]) plus either Rb or E1A for maximal transcriptional activity.

EXAMPLE 15
Substrate Specificity of p38 MAP Kinase

Substrate phosphorylation by p38 MAP kinase was examined by incubation of bacterially-expressed p38 MAP kinase with IκB, cMyc, EGF-R, cytoplasmic phospholipase $A_2$ (cPLA$_2$), c-Jun, and mutated ATF2 (Thr[69, 71]) and ATP [γ-$^{32}$P] (Raingeaud et al. (1995) J. Biol. Chem 270:7420, herein specifically incorporated by reference). GST-IκB was provided by Dr D. Baltimore (Massachusetts Institute of Technology). GST-cMyc (Alvarez et al. (1991) J. Biol. Chem. 266:15277), GST-EGF-R (residues 647–688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by PhosphorImager (Molecular Dynamics Inc.) analysis. The relative phosphorylation of ATF2, MBP, EGF-R, and IκB was 1.0, 0.23, 0.04, and 0.001, respectively.

EXAMPLE 16
Binding of of p38 MAP Kinase to ATF2

Cell extracts expressing epitope-tagged JNK1 and p38 MAP kinase were incubated with a GST fusion protein containing the activation domain of ATF2 (residues 1–109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). Immunocomplexes were detected using enhanced chemiluminescence (Amersham International PLC). Control experiments were performed using immobilized GST.

EXAMPLE 17
p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38 MAP kinase and JNK1 activity were measured in immunecomplex protein kinase assays using ATP[γ-$^{32}$P] and ATF2 as substrates. TNFα and IL-1α were from Genzyme Corp. Lipolysaccharide (LPS) was isolated from lyophilized *Salmonella minesota* Re595 bacteria as described (Mathison et a. (1988) J. Clin. Invest. 81:1925). Phorbol myristate acetate was from Sigma. EGF was purified from mouse salivary glands (Davis (1988) J. Biol. Chem. 263:9462). Kinase assays were performed using immunoprecipitates of p38 and JNK. The immunocomplexes were washed twice with kinase buffer (described above), and the assays initiated by the addition of 1 μg of ATF2 and 50 μM [γ-$^{32}$P]ATP (10 Ci/mmol) in a final volume of 25 μl. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/m$^2$ UV-C, 300 mM sorbitol, 10 ng/ml interleukin-1, and 10 ng/ml TNFα strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

|  | Relative Protein Kinase Activity | |
| --- | --- | --- |
|  | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/m$^2$) | 7.4 | 17.1 |

EXAMPLE 18
D38 MAP Kinase Activation by Dual Phosphorylation on Tyr and Thr

COS-1 cells expressing wild-type (Thr[180], Tyr[182]) or mutated (Ala[180], Phe[182]) p38 MAP kinase were treated without and with UV-C (40 J/m$^2$). The cells were harvested 30 minutes following exposure with or without UV radiation. Control experiments were performed using mock-transfected cells. The level of expression of epitope-tagged p38 MAP kinase and the state of Tyr phosphorylation of p38 MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P]phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [γ-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

EXAMPLE 19
MAP Kinase Phosphatase Inhibits p38 MAP Kinase Activation

The cells were treated without and with 40 J/m² UW-C. Control experiments were performed using mock-transfected cells (control) and cells transfected with the catalytically inactive mutated phosphatase mPAC1 ($Cys^{257}$/Ser) and human MKP1. The activity of p38 MAP kinase was measured with an immunecomplex protein kinase assay employing [$\gamma$-$^{32}$P]ATP and GST-ATF2 as substrates. The expression of PAC1 or MKP1 was found to inhibit p38 phosphorylation, demonstrating that p38 can be regulated by the dual specificity phosphatases PAC1 and MKP1.

EXAMPLE 20
Subcellular Distribution of p38 MAP Kinase

Epitope-tagged p38 MAP kinase was expressed in COS cells. The cells were treated without or with 40 J/m² UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry. Coverslips (22 mm×22 mm No. 1; Gold Seal Cover Glass; Becton-Dickinson) were pre-treated by boiling in 0.1 N HCl for 10 minutes, rinsed in distilled water, autoclaved and coated with 0.01% poly-L-lysine (Sigma; St. Louis Mo.). The coverslips were placed at the bottom of 35 mm multiwell tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). 24 hours post-transfection, the cells were rinsed once and incubated at 37° C. for 30 minutes in 25 mM Hepes, pH 7.4, 137 mM NaCl, 6 mM KCl, 1 mM $MgCl_2$, 1 mM $CaCl_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 22° C. The cells were permeabilized with 0.25% Triton X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% Triton X-100) for 5 minutes. The primary antibody (M2 anti-FLAG monoclonal antibody, Eastman-Kodak Co., New Haven, Conn.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, Md.) was applied at a 1:250 dilution for 1 hour at 22° C. in a humidified environment. The cells were then washed three times in DWB and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60× Planapo objective (numerical aperture=1.4) on a Zeiss IM-35 microscope equipped for epifluorescence as previously described (Carrington et al. (1990) in: Non-invasive Techniques in Cell Biology (Fosbett & Grinstein, eds.), Wiley-Liss, NY; pp. 53–72; Fay et al. (1989) J. Microsci. 153:133–149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125 μm intervals of a 0.3 μm diameter fluorescently labeled latex bead (Molecular Probes Inc.). The image restoration algorithm used is based upon the theory of ill-posed problems and obtains quantitative dye density values within the cell that are substantially more accurate than those in an un-processed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

EXAMPLE 21
Activation of the MKK Signal Transduction Pathway by Osmotic Shock CHO cells were co-transfected with the plasmid pCMV-Flag-Jnk1 and pRSV-Neo (Dérijard et al. (1994) supra). A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% Triton X-100, 2 mM EDTA, 137 mM NaCl, 25 mM β-glycerophosphate, 1 mM orthovanadate, 2 mM pyrophosphate, 10% glycerol, 1 mM phenylmethylsulfonyl fluoride, 10 μg/ml leupeptin) and a soluble extract was obtained by centrifugation at 100,000 g for 30 minutes at 4° C. The epitope-tagged JNK1 was isolated by immunoprecipitation with the monoclonal antibody M2 (Immunex Corp.). The immunoprecipitates were washed extensively with lysis buffer. Immunecomplex kinase assays were done in 25 μl of 25 mM Hepes, pH 7.4, 25 mM $MgCl_2$, 25 mM β-glycerophosphate, 2 mM dithiothreitol, 100 μM orthovanadate, and 50 μM ATP [$\gamma$-$^{32}$] (10 Ci/mmole) with 2.5 μg of bacterially expressed c-Jun (residues 1–79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed at all concentrations of sorbitol exposure.

The time course of JNK1 protein kinase activation was measured in cells incubated in medium supplemented with 300 mM sorbitol as described above. Increased JNK1 activity was observed within 5 minutes of exposure to sorbitol, with maximum activity occurring after 15–30 minutes.

Mutation of JNK1 at the phosphorylation sites $Thr^{183}$ and $Tyr^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Use

The MKK polypeptides and polynucleotides of the invention are useful for identifying reagents which modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, the kinase assay is tested with a range of reagent concentrations, e.g., 1.0 nM to 100 mM, a MKK substrate, and a radioactive marker such as [$\gamma$-$^{32}$P]ATP. Appropriate substrate molecules include p38, JNK1, JNK2, or ATF2. The incorporation of [$^{32}$]P into the substrate is determined, and the results obtained with the test reagent compared to control values. Of particular interest are reagents that result in inhibition of [$^{32}$]P of about 80% or more.

Assays that test the effect of a reagent on MKK synthesis can also be used to identify compounds that inhibit MKK signal transduction pathways. The effect of the test reagent on MKK expression is measured by, for example, Western blot analysis with an antibody specific for MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, *Remington's Pharmaceutical Sciences.* 18th ed., Gennaro, ed., Mack Publishing Company, Easton, Pa., 1990).

The invention provides methods for both acute and prophylactic treatment of stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent which inhibits MKK function or activity is administered to control inflammatory responses by inhibiting the secretion of inflammatory cytokines, including TNF and IL-1.

Stress-related proliferative disorders can also be treated by the method of the invention by administering a atherapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to ecrease protein kinase activity. Dominant-negative forms can be created by mutations within the catalytic domain of the protein kinases, as described above.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When a MKK-mediated disorder is associated with under-expression of MKK, or expression of a mutant MKK polypeptide, a sense polynucleotide sequence (the DNA coding strand) or MKK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A substantially pure human mitogen-activated protein kinase kinase (MKK) polypeptide having serine, theonine, and tyrosine kinase activity, and phosphorylating human mitogen-activated protein (MAP) kinase p38comprising the amino acid sequence of SEQ ID NO:2.

2. A substantially pure human mitogen-activated protein kinase kinase (MKK) polypeptide having serine, theonine, and tyrosine kinase activity, and phosphorylating human mitogen-activated protein (MAP) kinase p38 comprising the amino acid sequence of SEQ ID NO:4.

3. A substantially pure human mitogen-activated protein kinase kinase (MKK) polypeptide having serine, threonine, and tyrosine kinase activity, and phosphorylating human mitogen-activated protein (MAP) kinase p38, further characterized in that the polypeptide phosphorylates human mitogen-activated protein (MAP) kinase JNK comprising the amino acid sequence of SEQ ID NO:6.

4. A substantially pure human mitogen-activated protein kinase kinase (MKK) polypeptide having serine, threonine, and tyrosine kinase activity, and phosphorylating human mitogen-activated protein (MAP) kinase p38, further characterized in that the polypeptide phosphorylates human mitogen-activated protein (MAP) kinase JNK comprising the amino acid sequence of SEQ ID NO:8.

5. A substantially pure human mitogen-activated protein kinase kinase (MKK) polypeptide having serine, threonine, and tyrosine kinase activity, and phosphorylating human mitogen-activated protein (MAP) kinase p38, further characterized in that the polypeptide phosphorylates human mitogen-activated protein (MAP) kinase JNK comprising the amino acid sequence of SEQ ID NO:10.

6. A purified antibody which binds specifically to a polypeptide of claim 1.

7. A purified antibody which binds specifically to a polypeptide of claim 2.

8. A purified antibody which binds specifically to a polypeptide of claim 3.

9. A purified antibody which binds specifically to a polypeptide of claim 4.

10. A purified antibody which binds specifically to a polypeptide of claim 5.

* * * * *